(12) United States Patent
Dominguez-Villar et al.

(10) Patent No.: US 10,308,938 B2
(45) Date of Patent: Jun. 4, 2019

(54) COMPOSITIONS AND METHODS TO ACTIVATE OR INHIBIT TOLL-LIKE RECEPTOR SIGNALING

(71) Applicant: YALE UNIVERSITY, New Haven, CT (US)

(72) Inventors: Margarita Dominguez-Villar, New Haven, CT (US); David A. Hafler, New Haven, CT (US)

(73) Assignee: Yale University, Philadelphia, PA (US)

( * ) Notice: Subject to any disclaimer, the term of this patent is extended or adjusted under 35 U.S.C. 154(b) by 0 days.

(21) Appl. No.: 15/319,132

(22) PCT Filed: Jun. 18, 2015

(86) PCT No.: PCT/US2015/036478
§ 371 (c)(1),
(2) Date: Dec. 15, 2016

(87) PCT Pub. No.: WO2015/195947
PCT Pub. Date: Dec. 23, 2015

(65) Prior Publication Data
US 2017/0130228 A1    May 11, 2017

Related U.S. Application Data

(60) Provisional application No. 62/014,901, filed on Jun. 20, 2014.

(51) Int. Cl.
*A61K 39/21* (2006.01)
*C12N 15/113* (2010.01)
(Continued)

(52) U.S. Cl.
CPC ........ *C12N 15/1132* (2013.01); *A61K 31/437* (2013.01); *A61K 31/4745* (2013.01);
(Continued)

(58) Field of Classification Search
None
See application file for complete search history.

(56) References Cited

U.S. PATENT DOCUMENTS

2011/0118235 A1* 5/2011 Howbert ............ A61K 31/4025
514/213.01

FOREIGN PATENT DOCUMENTS

| WO | 2010080509 A1 | 7/2010 | |
| WO | WO 2010/080509 | * 7/2010 | ............ A61K 31/70 |
| WO | 2012061129 A1 | 5/2012 | |

OTHER PUBLICATIONS

International Search Report and Written Opinion for PCT International Application No. PCT/US2015/036478 dated Sep. 30, 2015.
(Continued)

*Primary Examiner* — Janet L Andres
*Assistant Examiner* — Stuart W Snyder
(74) *Attorney, Agent, or Firm* — Saul Ewing Arnstein & Lehr LLP; Kathryn Doyle

(57) ABSTRACT

The present invention includes compositions and methods of inhibiting or activating TLR7 signaling. In one aspect, a composition includes an inhibitor of TLR7 signaling is described, where the inhibitor of TLR7 signaling is a TLR7 inhibitory oligonucleotide, a TLR7 antibody, or a TLR7 antagonist. In another aspect, a composition and method are described for preventing and treating viral infection of a T cell in a subject. Methods for decreasing T cell proliferation by administering a composition with a TLR7 ligand or agonist or inducing T cell anergy in a subject by stimulating T cells with a TLR7 ligand or agonist are also described.

7 Claims, 60 Drawing Sheets
Specification includes a Sequence Listing.

(51) Int. Cl.
  *A61K 31/4745* (2006.01)
  *C07K 16/28* (2006.01)
  *A61K 31/437* (2006.01)
  *A61K 31/708* (2006.01)
  *A61K 31/7088* (2006.01)
  *A61K 39/395* (2006.01)
  *G01N 33/569* (2006.01)
  *A61K 39/00* (2006.01)

(52) U.S. Cl.
  CPC ........ *A61K 31/708* (2013.01); *A61K 31/7088* (2013.01); *A61K 39/39541* (2013.01); *C07K 16/28* (2013.01); *C07K 16/2809* (2013.01); *C07K 16/2827* (2013.01); *C07K 16/2896* (2013.01); *G01N 33/56972* (2013.01); *A61K 2039/505* (2013.01); *C12N 2310/14* (2013.01); *C12N 2320/31* (2013.01)

(56) References Cited

OTHER PUBLICATIONS

Cherfils-Vicini, et al., "Triggering of TLR7 and TLR8 expressed by human lung cancer cells induces cell survival and chemoresistance", The Journal of Clinical Investigation 120(4), Apr. 2010, 1285-1297.

Kim, et al., "Analysis of cellular and behavioral responses to imiquimod reveals a unique itch pathway in transient receptor potential vanilloid 1 (TRPV1)-expressing neurons", PNAS 108(8), Feb. 2011, 3371-3376.

Lukacs, et al., "Respiratory Virus-Induced TLR7 Activation Controls IL-17 -Associated Increased Mucus via IL-23 Regulation", The Journal of Immunology 185, Jul. 2010, 2231-2239.

Xiong, et al., "Topical Imiquimod has Therapeutic and Immunomodulatory Effects Against Intracranial Tumors", Journal of Immunotherapy 34(3), Apr. 2011, 264-269.

\* cited by examiner

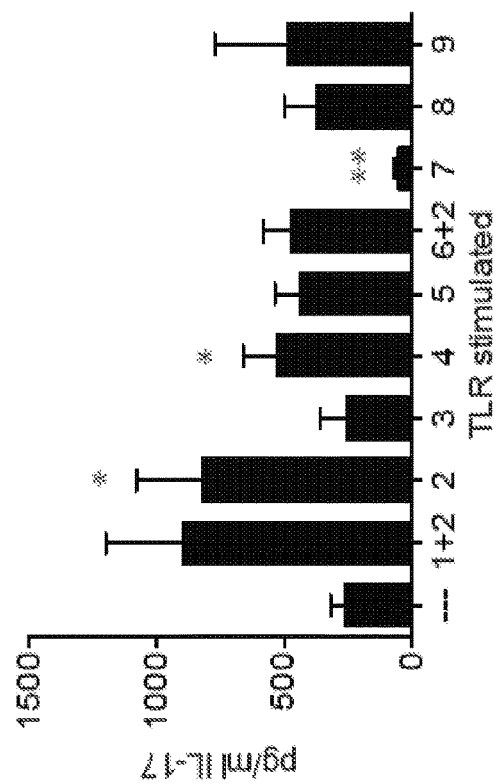
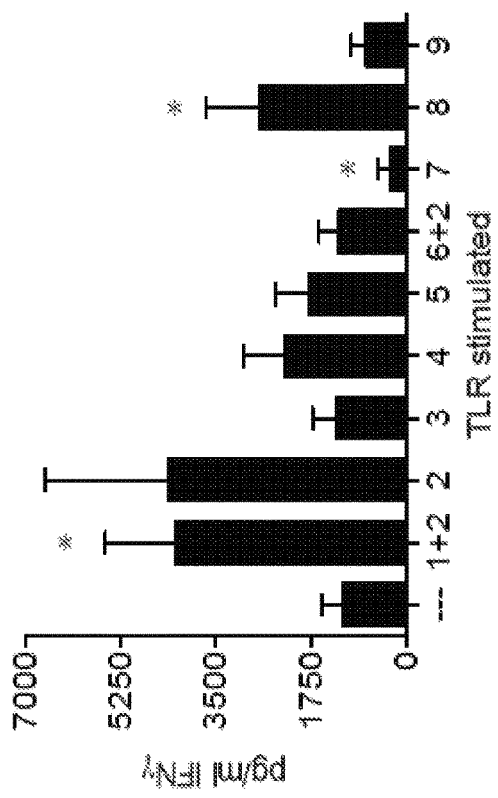
Figure 3A
Figure 3B

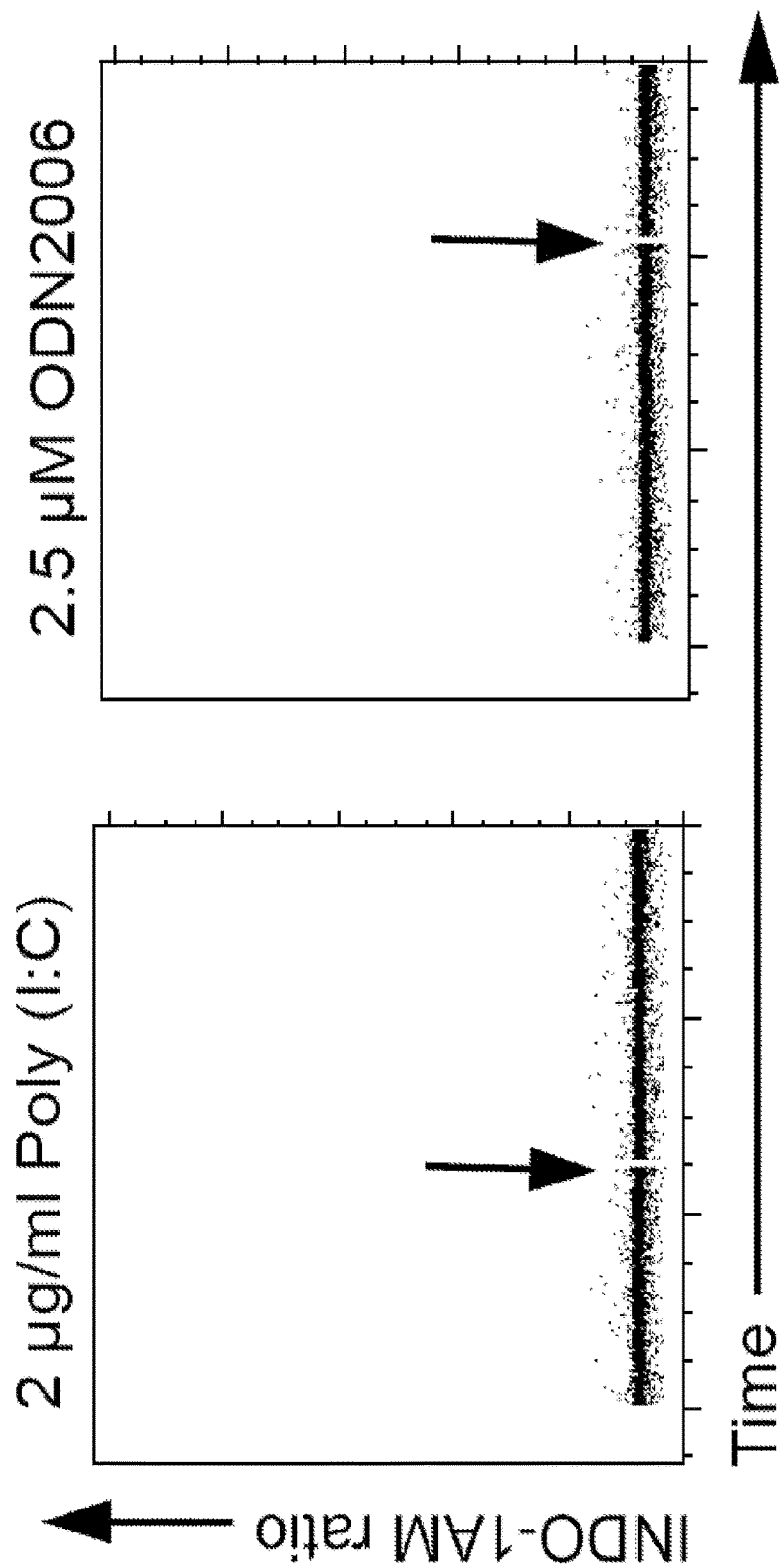

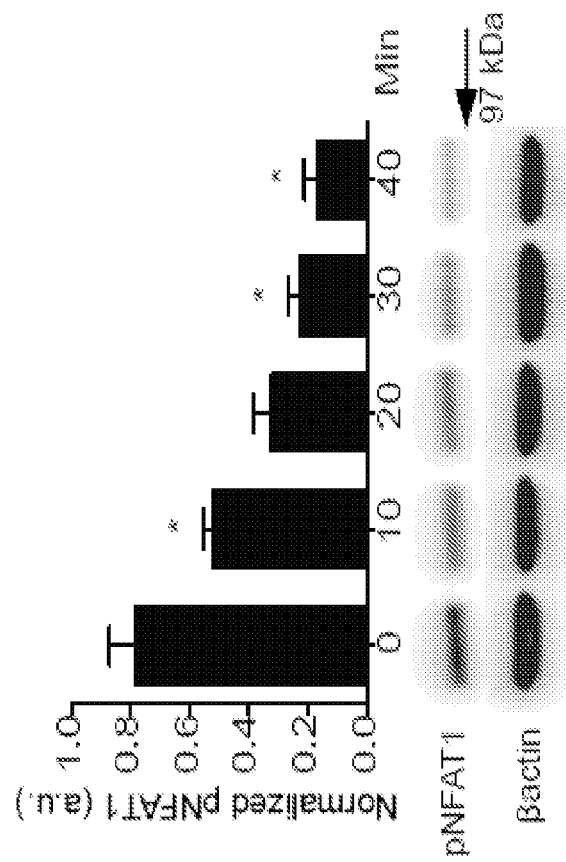
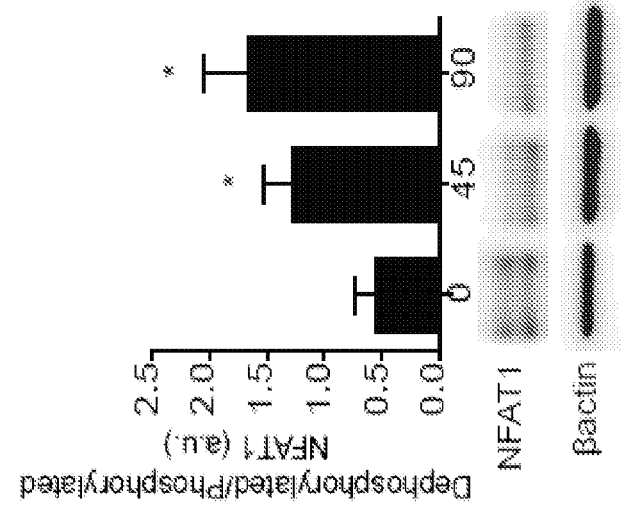
Figure 25A
Figure 25B

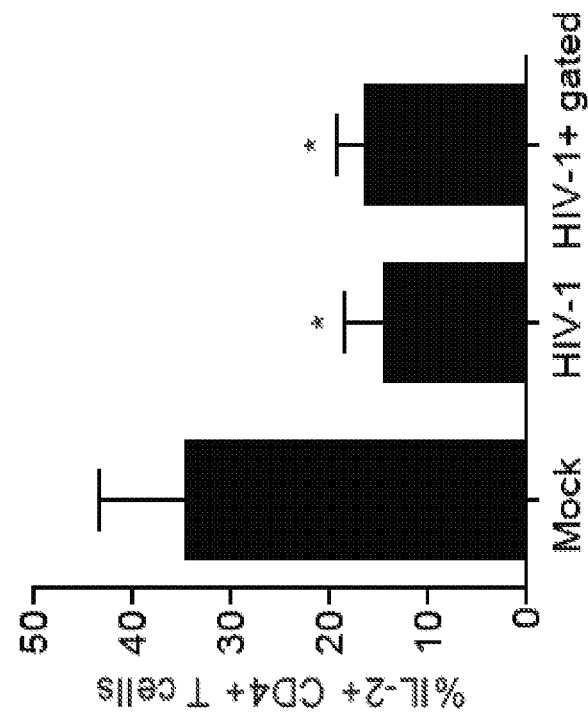
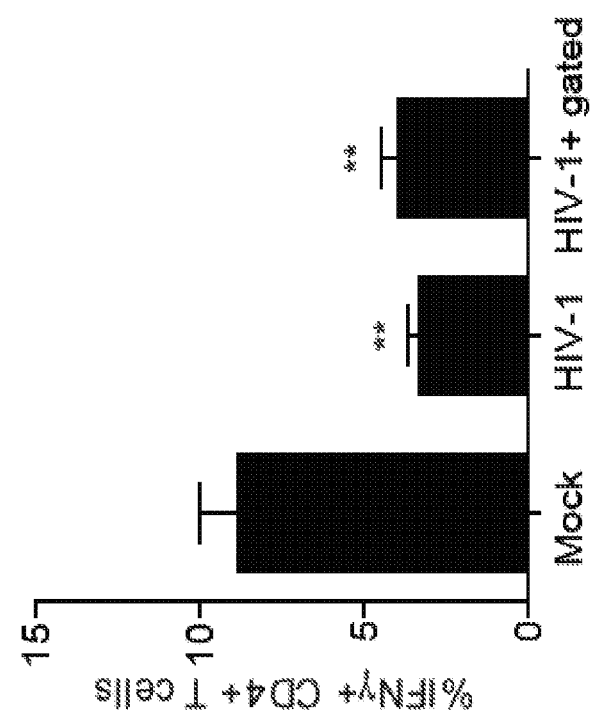

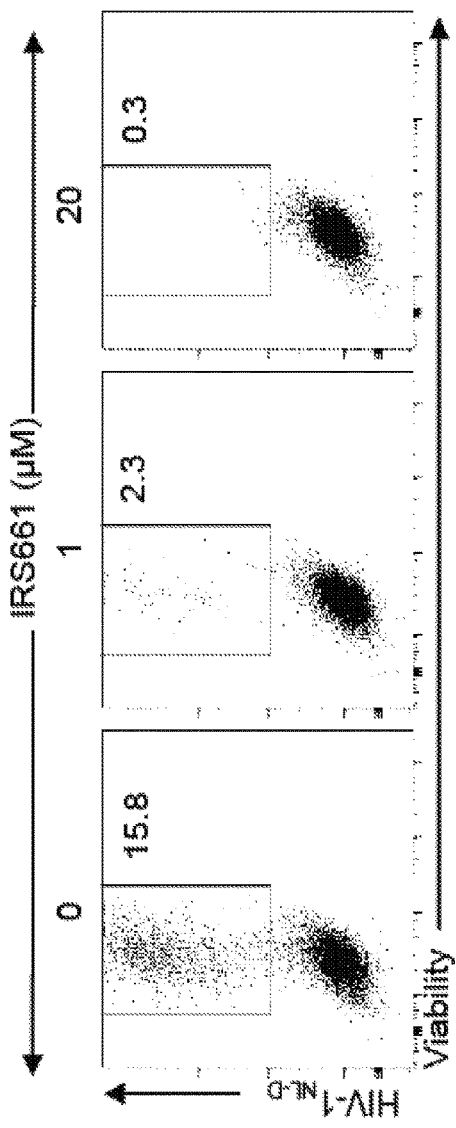
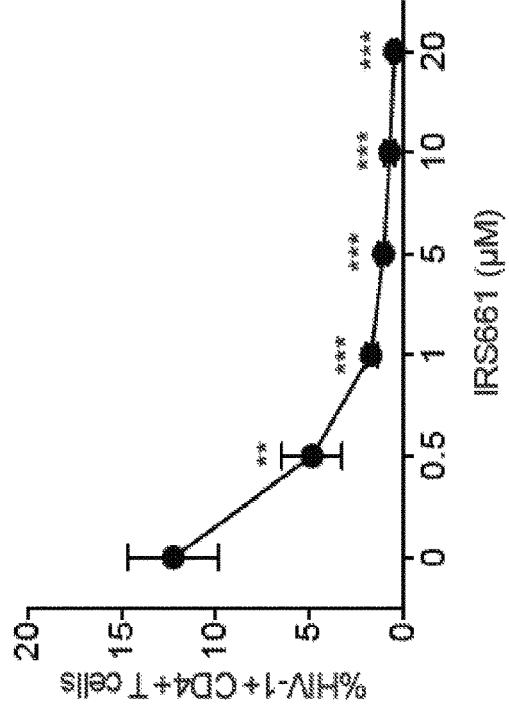
Figure 37A
Figure 37B

COMPOSITIONS AND METHODS TO ACTIVATE OR INHIBIT TOLL-LIKE RECEPTOR SIGNALING

CROSS-REFERENCE TO RELATED APPLICATION

This application is a 35 U.S.C. § 371 national phase application from, and claims priority to, International Application No. PCT/US2015/036478, filed Jun. 18, 2015,and published under PCT Article 21(2) in English, which claims priority to U.S. Provisional Application No. 62/014,901, filed Jun. 20, 2014, all of which applications are incorporated herein by reference in their entireties.

BACKGROUND OF THE INVENTION

Toll-like receptors (TLR) represent the major pathway by which microorganisms interact with host cells of the innate immune system. They are a family of highly conserved class of pattern recognition receptors that recognize distinct pathogen-associated molecular patterns that are conserved in specific classes of microorganisms. Human TLR family consists of at least 10 members that can be classified into two different groups based on their cellular location. Intracellular TLR (TLR3, 7, 8 and 9) recognize nucleic acids; TLR7 and TLR8 recognize single-stranded RNA, while TLR3 and TLR9 are receptors for double-stranded RNA and DNA, respectively. In contrast, cell surface TLR (TLR1, 2, 4 and 5) recognize different components of bacteria. The expression and signaling pathways triggered by stimulating the TLR have been primarily described in antigen presenting cells (APC) that generally lead to activation of APC with inflammatory and antiviral cytokine secretion. Although predominantly studied in APC, several reports have described the expression of TLR on lymphocytes, and specifically on $CD4^+$ T cells. As with APC, these studies indicate that TLR engagement acts as a positive costimulatory signal that increases the secretion of pro-inflammatory cytokines, proliferation and cell survival.

The innate immune system, induced by TLR signaling, is known to play a critical role in response to viral invasion. Chronic infectious viral diseases are characterized by the inability of the host immune system to mount a strong, long-lasting response against the infectious agent. In some RNA virus infections, such as hepatitis C (HCV), human immunodeficiency virus 1 (HIV-1) and human T-lymphotropic virus 1 (HTLV-1) infections, it has been shown that $CD4^+$ T helper cell- and $CD8^+$ cytotoxic T-cell-mediated immune responses determine the outcome of the infection, with chronic infections correlating with late, transient, weak or narrowly focused $CD4^+$ and $CD8^+$ T cell responses. Several studies have demonstrated that there is impairment with activation and/or function of T cells in HIV-1 infection. Specifically, $CD4^+$ T cells from chronically HIV-1-infected patients display an anergic phenotype with defects in proliferation and IL-2 and IFNγ secretion Multiple anti-viral drugs have been approved by the Food and Drug Administration to treat viral infections. These treatments focus on suppressing viral activity, but do not focus on mounting an immune response against the virus to eliminate it from the body. A need exists in the art for improved treatments and methods to improve host responses to viral infections, especially in the case of chronic viral infection.

SUMMARY OF THE INVENTION

As described below, the present invention includes compositions and methods of inhibiting or activating TLR7 signaling.

In one aspect, the invention includes a method of preventing a viral infection of a T cell in a subject in need thereof comprising administering a composition comprising an inhibitor of TLR7 signaling to the subject, wherein viral infection of the T cell is prevented following administration of the composition.

In another aspect, the invention includes a method of treating a viral infection in a subject in need thereof comprising administering a composition comprising an inhibitor of TLR7 signaling to the subject, wherein the viral infection is reduced in the subject following administration of the TLR7 inhibitor.

In various embodiments of the above aspects or any other aspect of the invention delineated herein, the inhibitor of TLR7 signaling is selected from the group consisting of a TLR7 inhibitory oligonucleotide, a TLR7 antibody, and a TLR7 antagonist. In one embodiment, the TLR7 inhibitory oligonucleotide comprises a modification selected from the group consisting of a 2'-uridine modification, a 2'deoxy-7-deazaguanosine modification, an arabinoguanosine modification, and any combination thereof. In another embodiment, the inhibitor of TLR7 signaling is capable of decreasing expression of TLR7.

In another embodiment, the subject is exposed to a virus prior to or after administration of the composition. In yet another embodiment, the composition is capable of preventing a viral infection of a CD4+ T cell. In these embodiments, the viral infection may be selected from the group consisting of a hepatitis B virus (HBV), a hepatitis C virus (HCV), human T-lymphotropic virus (HTLV) and a human immunodeficiency virus (HIV) infection.

In another embodiment, administering the inhibitor of TLR7 signaling further comprises administering a recombinant expression vector comprising the inhibitor of TLR7 signaling. In yet another embodiment, administering the composition increases secretion of at least one selected from the group consisting of IL-2, IFNγ and IL-17. In still another embodiment, the method includes activating a co-stimulatory molecule on a T cell, such as administering a CD3 antibody, an ICOS antibody, or a CD28 antibody.

In another aspect, the invention includes a method of decreasing T cell proliferation in a subject in need thereof comprising administering a composition comprising a TLR7 ligand or agonist to the subject, wherein the proliferation of T cells is reduced in the subject following administration of the composition.

In yet another aspect, the invention includes a method of inducing T cell anergy in a subject in need thereof comprising stimulating T cells with a TLR7 ligand or agonist.

In various embodiments of the above aspects or any other aspect of the invention delineated herein, the TLR7 ligand or agonist is selected from the group consisting of R848, imiquimod, gardiquimod, loxoribine, CL264, and combinations thereof.

In another embodiment, the composition induces an increase in intracellular calcium concentration. In yet another embodiment, the composition inhibits both CD4+ and CD8+ T cell proliferation.

In yet another embodiment, administering the composition decreases secretion of at least one selected from the group consisting of IL-2, IFNγ and IL-17.

In still another embodiment, the subject has an autoimmune disease.

BRIEF DESCRIPTION OF THE DRAWINGS

The following detailed description of embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A shows a bar graph of IFNγ ELISA measurements after 3 days of stimulation ($*P<0.05$, $**P<0.005$).

FIG. 3B shows a bar graph of IL-2 ELISA measurements after 3 days of stimulation ($*P<0.05$, $**P<0.005$).

FIG. 24A is a histogram showing the calcium flux as measured by INDO-1AM ratio over time on CD4$^+$ T cells stimulated with Poly(I:C) (TLR3 ligand). Representative example of five independent experiments performed.

FIG. 24B is a histogram showing the calcium flux as measured by INDO-1AM ratio over time on CD4$^+$ T cells stimulated with ODN2006 (TLR9 ligand). Representative example of five independent experiments performed.

FIG. 25A shows the dephosphorylated/phosphorylated NFAT1 ratio at 0, 45 and 90 minutes after IMQ treatment as measured by Western blot with an anti-NFAT1 antibody.

FIG. 25B shows the normalized phosphoNFAT intensity at 0, 10, 20, 30 and 40 minutes after stimulation with IMQ.

FIG. 30A shows anergy-related gene expression, Kmd6b, analyzed on resting NFAT1 or non-target-transduced cells after IMQ treatment for 2 hours, by TaqMan real-time PCR. (n=3). Statistical analysis represents mean±s.e.m. of three independent experiments, *p<0.05, p<0.005, *p<0.0005.

FIG. 30B shows anergy-related gene expression, Ikzf1, analyzed on resting NFAT1 or non-target-transduced cells after IMQ treatment for 2 hours, by TaqMan real-time PCR. (n=3). Statistical analysis represents mean±s.e.m. of three independent experiments, *p<0.05, p<0.005, *p<0.0005.

FIG. 30C shows anergy-related gene expression, Grg4, analyzed on resting NFAT1 or non-target-transduced cells after IMQ treatment for 2 hours, by TaqMan real-time PCR. (n=3). Statistical analysis represents mean±s.e.m. of three independent experiments, *p<0.05, p<0.005, *p<0.0005.

FIG. 30D shows anergy-related gene expression, Rab10, analyzed on resting NFAT1 or non-target-transduced cells after IMQ treatment for 2 hours, by TaqMan real-time PCR. (n=3). Statistical analysis represents mean±s.e.m. of three independent experiments, *p<0.05, p<0.005, *p<0.0005.

FIG. 34A shows a statistical analysis of IFNγ (n=3). (*P<0.05, **P<0.005).

FIG. 34B shows a statistical analysis of IL-2 (n=3). (*P<0.05, **P<0.005).

FIG. 37A is a panel of histograms showing a representative example of the frequency of viable HIV-1$_{NL-D}$+CD4+ T cells stimulated in the presence of various doses of IRS661 for two days and infected with HIV-1$_{NL-D}$ at day 7 after infection.

FIG. 37B is a statistical analysis of the frequency of HIV-1$_{NL-D}$+CD4+ T cells incubated with different doses of IRS661 (n=3).

DETAILED DESCRIPTION OF THE INVENTION

Definitions

Figure 1:
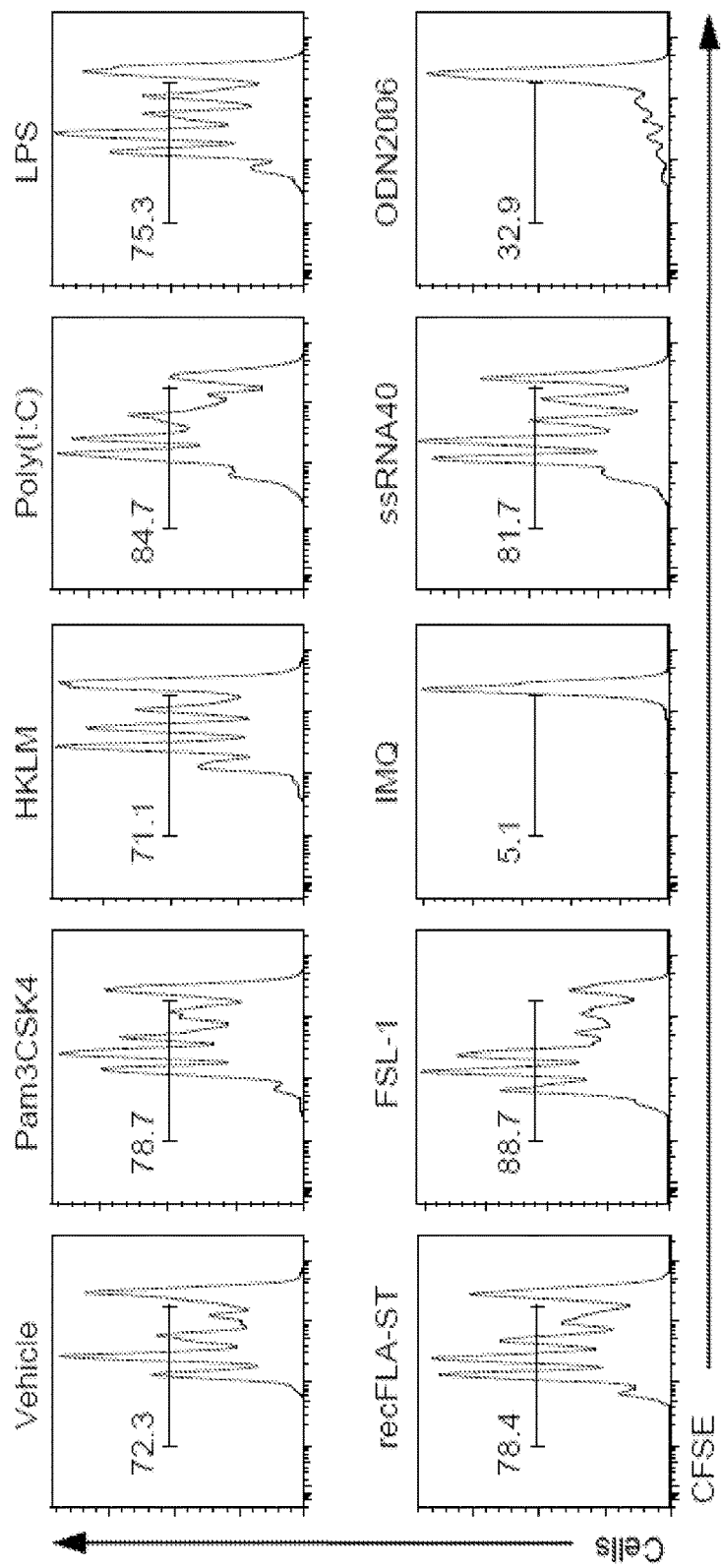
FIG. 1 is a panel of histograms showing the frequency of viable proliferating $CD4^+$ T cells (numbers in histograms).

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

By "activator of a co-stimulatory molecule" is meant the interaction of a co-stimulatory molecule expressed on the surface of the T cell and a ligand, such as CD80, CD86, of the co-stimulatory molecule. The ligand may be presented on antigen presenting cells, or the ligand may be present in other forms to activate the co-stimulatory molecule. Examples of co-stimulatory molecules include, but are not limited to, CD3, ICOS, and CD28. Activation of co-stimulatory molecules can induce T cell proliferation, differentiation and survival. Without proper antigen and co-stimulatory molecule activation of T cells, T cell anergy, T cell deletion or the development of immune tolerance may result.

By "autoimmune disease" is meant disorder or condition characterized by abnormal immune responses of the body against substances and tissues normally present in the body. The autoimmune disease may be restricted to certain organs or involve particular tissues in different locations of the body. The autoimmune disease may be characterized by an imbalance in regulatory T cells (e.g. excessive proliferation) and/or autoreactive T cells with specificity to autoantigens. Examples of autoimmune diseases include, but are not limited to, Addison's disease, celiac disease, Graves disease, multiple sclerosis, myasthenia gravis, arthritis, Sjogren's syndrome, systemic lupus erythematosus, and type I diabetes.

By "inhibitor of TLR7 signaling" is meant a molecule that decreases or prevents TLR7 signaling. The inhibitor of TLR7 signaling can disrupt TLR7 ligand binding, bind the TLR7 ligand or TLR7 binding site, possibly with higher association efficiency than the TLR7 ligand, and/or prevent effective ligand binding to decreases or prevents TLR7 activation or downstream signaling. Inhibitors of TLR7 signaling include, but are not limited to, small molecule TLR7 inhibitors, TLR7 antagonists, neutralizing antibodies, and inhibitory oligonucleotides.

By "neutralizing antibody" is meant an antibody that prevents TLR7 activation through ligand binding. For example, the neutralizing antibody may bind to the TLR7 ligand binding site, thereby preventing activation of TLR7 and signaling.

By "shRNA" is meant sequences of RNA that make a tight hairpin that can be used to silence target gene expression via RNA interference (RNAi). Expression of the shRNA in cells can be obtained by delivery of plasmids or viral or bacterial vectors. Examples of shRNA include, but are not limited to, IRS 661, IRS 954, and IRS 967.

By "TLR7" or "Toll-like receptor 7" is meant a protein that is a member of the Toll-like receptor (TLR) family which plays a fundamental role in pathogen recognition and activation of innate immunity. An exemplary TLR7 sequence includes human TLR7 found at GenBank Accession No. NM_016562 and NP_057646, or a fragment thereof, and the mouse TLR7 sequence found at NM_133211 or NP_573474, or a fragment thereof.

A "TLR7 inhibitory oligonucleotide" refers to a nucleic acid molecule, typically RNA, that inhibits gene expression, for example by causing the destruction of specific mRNA molecules. Examples of TLR7 inhibitory oligonucleotides include small ribonucleic acid (RNA) molecules, such as microRNA (miRNA), small hairpin RNA or short hairpin RNA (shRNA) (sequences of RNA that make a tight hairpin) and small interfering RNA (siRNA).

A "TLR7 antibody" refers to a monoclonal or polyclonal antibody specific for TLR7. Examples of TLR7 antibodies include, but are not limited to, 1G8, 2C9, 2F6, 2F8, 3G6, 4G6, V-20, 4F4, 533707, and H-114.

By "TLR7 antagonist" is meant a molecule that does not provoke a TLR7 biological response. The TLR7 antagonist can prevent or decrease ligand- or agonist-mediated TLR7 responses. The TLR7 antagonist may have affinity for TLR7 and bind the receptor where binding disrupts the interaction of other ligands, thereby inhibiting the TLR7 activation. Other TLR7 antagonists may have affinity for TLR7 ligands or agonists and compete with the receptor to bind the ligands or agonists, thereby preventing or reducing the ability of a ligand or agonist to bind the receptor. Typically, these TLR7 antagonists have a greater affinity or a lower dissociation constant for the TLR7 ligands or agonists than the receptor.

By "TLR7 ligand or agonist" is meant a molecule that binds to TLR7 and triggers activation of the receptor. TLR7 ligand or agonist often mimics the action of a naturally occurring TLR7 ligand. Examples of TLR7 ligands or agonists include, but are not limited to, R848, imiquimod, gardiquimod, loxoribine, and CL264.

"T cell anergy" refers to a T cell that is functionally inactivated following an antigen encounter, but remains alive for an extended period of time in a hyporesponsive state.

By "viral infection" is meant the invasion of a host cell, such as a human cell, by a viral particle or virus. Non-limiting examples of viruses include, but are not limited to, hepatitis B virus (HBV), hepatitis C virus (HCV), human T-lymphotropic virus (HTLV) and human immunodeficiency virus (HIV).

A "vector" is a composition of matter that comprises the inhibitor of TLR7 signaling and that may be used to deliver the inhibitor of TLR7 signaling to the interior of a cell. Vector refers to any plasmid containing the inhibitor of TLR7 signaling that is capable of moving foreign sequences into the genomes of a target organism or cell.

"Expression vector" or "recombinant expression vector" refers to a vector comprising the inhibitor of TLR7 signaling with expression control sequences operatively linked to the inhibitor of TLR7 signaling to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount required to reduce or improve at least one symptom of a disease relative to an untreated patient. The effective amount of an active compound(s) used for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "reference" is meant a standard or control. A "reference" is a defined standard or control used as a basis for comparison.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Description

It has been discovered that engagement of TLR7 by a RNA virus induces anergy in T cells. An intracellular calcium flux occurs resulting in activation of NFAT-dependent anergic gene expression programs. The invention includes compositions that inhibit TLR7 signaling, thereby preventing viral induced anergy of T cells via TLR7. Alternatively, promoting TLR7 signaling induces anergy that may be useful for treating excessive proliferation of T cells or autoreactive T cells. Thus, the invention includes compositions that promote TLR7 signaling, thereby decreasing proliferation or inducing anergy in autoreactive T cells.

Compositions

Compositions that Inhibit TLR7 Signaling

In one aspect, the invention includes a composition that prevents viral infection of a T cell in a subject in need thereof. The composition includes an inhibitor of TLR7 signaling and a pharmaceutically acceptable carrier.

In one embodiment, the inhibitor of TLR7 signaling is capable of reducing expression of TLR7. In another embodiment, the inhibitor of TLR7 signaling is capable of preventing viral infection of a T cell. In yet another embodiment, the composition is capable of preventing viral infection of a CD4+ T cell.

The invention includes, in one aspect, compositions that comprise an inhibitor of TLR7 signaling, where the TLR7 inhibitor is at least a TLR7 inhibitory oligonucleotide, a TLR7 antibody and a TLR7 antagonist. In another embodiment, the inhibitor of TLR7 signaling is a TLR7 inhibitory oligonucleotide, such as shRNA and siRNA. Examples of TLR7 shRNAs include, but are not limited to, IRS 661 (SEQ ID NO:1, 5'-TGCTTGCAAGCTTGCAAGCA-3'), IRS 954 (SEQ ID NO:2, 5'-TGCTCCTGGAGGGGTTGT-3'), IRS 957 (SEQ ID NO:3, 5'-TGCTTGACATCCTGGAGGGGT-TGT-3'), IRS 967 (SEQ ID NO:4, 5'-TGCTTGACAGCTT-GACAGCATCCTGGAGGGGTTGT-3'), IRS 986 (SEQ ID NO:5, 5'-GCTCCTGGAGGGGTTGT-3'), IRS 987 (SEQ ID NO:6, 5'-CTCCTGGAGGGGTTGT-3'), IRS 988 (SEQ ID NO:7, 5'-AAATCCTGGAGGGGTTGT-3'), and combinations thereof. Nucleotide modifications can also convert an oligonucleotide into aTLR7 inhibitory molecule. Such modifications may include 2'-uridine modification, a 2'deoxy-7-deazaguanosine modification, an arabinoguanosine modification, and any combination thereof.

In another embodiment, the inhibitor of TLR7 signaling is a TLR7 antibody, such as a neutralizing antibody. While any TLR7 antibody may be used that is known in the art and useful for the compositions and methods described herein, some examples include, 1G8, 2C9, 2F6, 2F8, 3G6, 4G6, V-20, 4F4, 533707, and H-114.

In another embodiment, the inhibitor of TLR7 signaling is a TLR7 antagonist, such as a dual-iODN, IMO-3100, DV056, DV1179, chloroquine, hydroxychloroquine, quinacrine, and any combination thereof. The TLR7 antagonist can decrease ligand- or agonist-mediated TLR7 response or activation by directly preventing or decreasing ligand- or agonist-mediated TLR7 response or activation. In one embodiment, the TLR7 antagonist binds TLR7. This direct binding to the receptor can prevent or disrupt potential interactions of other ligands or agonists, thereby inhibiting TLR7 activation. In another embodiment, the TLR7 antagonist has affinity for TLR7 ligands or agonists. This causes a direct competition between the TLR7 antagonist and the receptor to bind the ligands or agonists, thereby preventing or reducing the ability of a ligand or agonist to bind the receptor. The invention therefore includes TLR7 antagonists that have a greater affinity or a lower dissociation constant for the TLR7 ligands or agonists than the receptor.

Compositions that Induce TLR7 Signaling

Compositions that induce T cell anergy are also included in the invention. Certain diseases, such as autoimmune diseases, are characterized by excessive proliferation of T cells or autoreactive T cells. Treatments that decrease proliferation or induce anergic states in autoreactive T cells are therefore included in the invention. In one aspect, the invention includes a composition that induces T cell anergy comprising a TLR7 ligand or agonist. In another aspect, the invention includes a composition that is capable of decreasing secretion of cytokines or growth factors, such as IL-2, IFNγ and IL-17.

In one embodiment, the TLR7 ligand or agonist activates TLR7. Examples of TLR7 ligands or agonists include R848, imiquimod, gardiquimod, loxoribine, CL264, and combinations thereof.

In order to fully activate a T cell, the T cell necessarily interacts with an antigen-specific signal and an antigen nonspecific signal, such as co-stimulatory molecule. In situations where T cells receive one signal and not the other, the T cells may become either anergic or may be eliminated through T cell deletion. In another embodiment, the invention therefore also includes a composition that activates a co-stimulatory molecule. In one aspect, the activator of the co-stimulatory molecule activates at least one co-stimulatory molecule, such as CD3, ICOS, and CD28. In another aspect, the activator of the co-stimulatory molecule includes a CD3 antibody, an ICOS antibody, and a CD28 antibody.

Methods

Methods for Inhibiting TLR7 Signaling

The present invention also includes a method for preventing or treating a viral infection of a T cell by inhibiting TLR7 signaling in a subject in need thereof. As described herein, inhibition of the TLR7 pathway prevents T cell anergy that may result from infection with a virus. Administering a composition that includes a TLR7 ligand or agonist, such as TLR7 inhibitory oligonucleotide, anti-TLR7 antibody or a TLR7 antagonist to the subject provides a means for preventing or treating a viral infection.

In one aspect, the invention includes a method for preventing a viral infection of a T cell in a subject in need thereof. The method comprises administering a composition comprising an inhibitor of TLR7 signaling to the subject, wherein viral infection of the T cell is prevented following administration of the composition. In another aspect, the invention includes a method of treating a viral infection in a subject in need thereof where the method comprises administering a composition comprising an inhibitor of TLR7 signaling to the subject, wherein the viral infection is reduced in the subject following administration of the TLR7 inhibitor.

In one embodiment, the method includes administering a recombinant expression vector comprising the inhibitor of TLR7 signaling. The recombinant expression vector expressed the inhibitor of TLR7 signaling in T cells, so as to prevent T cell anergy. Optionally, the recombinant expression vector includes expression control sequences that are operatively linked to the inhibitor of TLR7 signaling. These sequences facilitate inducible expression of the inhibitor of TLR7 signaling.

In another embodiment, the composition is capable of preventing viral infection of a CD4+ T cell. In instances when the composition is administered to the subject prior to exposure to the virus, the composition prevents viral infection of the T cell. In instances when the composition is administered to the subject after exposure to the virus, the composition may treat or decrease viral infection of a T cell. In these and other embodiments, the virus may be hepatitis B virus (HBV), hepatitis C virus (HCV), human T-lymphotropic virus (HTLV) or a human immunodeficiency virus (HIV).

Methods for Inducing TLR7 Signaling

Alternatively, the invention includes a method for decreasing T cell proliferation in a subject in need thereof. The method comprises administering a composition comprising a TLR7 ligand or agonist, such as R848, imiquimod, gardiquimod, loxoribine, CL264, or combinations thereof, to the subject, wherein the proliferation of T cells is reduced in the subject following administration of the composition. In one embodiment, the method further includes activating co-stimulatory molecules on the T cell, where such activating is accomplished by administering a CD3 antibody, an ICOS antibody, or a CD28 antibody. In another embodiment, administering the composition induces an increase in intracellular calcium concentrations in the T cell. In yet another embodiment, administering the composition inhibits both CD4+ and CD8+ T cell proliferation in the subject.

In another aspect, the invention includes a method for inducing T cell anergy in a subject in need thereof, where the method comprises stimulating T cells by administering to the subject a TLR7 ligand or agonist, such as R848, imiquimod, gardiquimod, loxoribine, CL264, or combinations thereof. In one embodiment, administering the composition induces an increase in intracellular calcium concentrations in the T cell. The increase in intracellular calcium results in activation of NFAT-dependent anergic gene expression programs, thereby inducing T cell anergy.

The methods and composition disclosed herein are also useful as a treatment for autoimmune disease in a subject where the autoimmune disease is characterized by autoreactive T cells or a disorder/condition/disease characterized by excessive T cell proliferation.

Pharmaceutical Compositions

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

The toll like receptors (TLRs) play a central role in the pattern recognition of microbial structures sensing infectious agents leading to the rapid activation of innate cells such as dendritic cells and macrophages directing the adaptive T cell response. While TLRs are expressed on myeloid derived cell populations, it is well recognized that they can be expressed on $CD4^+$ T cells though their function in adaptive immune responses is not established. Described herein is evidence that engagement of TLR7 by single stranded RNA viruses induced totally anergy in $CD4^+$ T cells by inducing an intracellular calcium flux with activation of NFAT-dependent anergic gene expression program. Moreover, RNAi knockdown of the TLR7 gene markedly decreased the capacity of HIV-1 to infect $CD4^+$ T cells in vitro while restoring T cell responsiveness in HIV-1-infected cells. Finally, induction of TLR7 signaling led to increased HIV-1 infectivity in $CD4^+$ T cells. These data establish a novel role for TLRs in regulating adaptive immune responses and suggest new methods for the treatment of HIV and other RNA viruses.

The Materials and Methods used in the performance of the experiments disclosed herein are now described.

Cell culture reagents and antibodies. Cells were cultured in RPMI 1640 media supplemented with 2 nM L-glutamine, 5 mM HEPES, and 100 U/μg/ml penicillin/streptomycin (Biowhittaker, Walkersville, Md.), 0.5 mM sodium pyruvate, 0.05 mM nonessential amino acids (Life Technologies, Rockville, Md.), and 5% human AB serum (Gemini Bio-Products, Woodland, Calif.). The antibodies used for stimulation were anti-human CD3 (clone UCHT1 and clone Hit3a) and anti-human CD28 (clone 28.2) (BD Biosciences, San Jose, Calif.) at 1 µg/ml. IL-2 was obtained through the AIDS Research and Reference Reagent Program, Division of AIDS, National Institute of Allergy and Infectious Diseases (NIAID), National Institutes of Health (NIH), and was used at 10 U/ml at the initiation of cultures. All TLR ligands (EndoFit™, <0.001 EU/µg) were purchased from Invivogen and resuspended in endotoxin-free water as per manufacturer recommendations. The concentrations of each TLR ligand used, unless otherwise noted, are summarized in Table 1. Phorbol 12-myristate 13-acetate (PMA) and Ionomycin were purchased from Sigma-Aldrich. IRS661 (SEQ ID NO:1) TLR-specific inhibitory sequence was synthesized by Sigma-Aldrich on a phosphorothioate backbone.

TABLE 1

TLR ligand concentrations

| Reagent | TLR | Concentration |
|---|---|---|
| Pam3CSK4 | TLR1/TLR2 | 0.5 µg/ml |
| Heat-killed *Lysteria Monocytogenes* (HKLM) | TLR2 | 5 × 10$^7$ cells/ml |
| Poly (I:C) (High molecular weight) | TLR3 | 10 µg/ml |
| Ultrapure lipopolysaccharide from *E. coli* K12 strain (LPS-EK) | TLR4 | 10 µg/ml |
| Recombinant Flagellin from *Salmonella typhimurium* (recFLA-ST) | TLR5 | 0.2 µg/ml |
| Synthetic diacylated lipoprotein (FSL-1) | TLR6/TLR2 | 0.2 µg/ml |
| Imiquimod (IMQ) | TLR7 | 0.1-10 µg/ml |
| Gardiquimod (GDQ) | TLR7 | 5 µg/ml |
| Loxoribine (Loxo) | TLR7 | 1 mM |
| CL264 | TLR7 | 20 µg/ml |
| ssRNA40/LyoVec | TLR8 | 0.5 µg/ml |
| ODN2006 | TLR9 | 2.5 µM |

Study subjects. Peripheral blood was drawn from healthy individuals after informed consent and approval by the Institutional Review Board at Yale University.

Cell isolation and FACS sorting of T cell populations. Peripheral blood mononuclear cells (PBMC) were isolated from healthy donors by Ficoll Hypaque gradient centrifugation. Total CD4$^+$ T cells were isolated by negative selection using CD4$^+$ T cell isolation kit (StemCell Technologies, Vancouver, BC) and stained for fluorescence-activated cell sorting (FACS) with the following antibodies: anti-CD45RO (clone UCHL1), CD45RA (clone H1100), CD25 (clone M-A251) (all from BD Biosciences) and CD127 (clone eBioRDR5) from eBioscience (San Diego, Calif.). The Treg (CD4$^+$CD25$^{hi}$CD127$^{low/neg}$) memory T cell (CD4$^+$CD45RA$^-$CD45RO$^+$CD25$^{low/neg+}$) and naïve T cell (CD4$^+$CD45RA$^+$CD45RO$^-$CD25$^{low/neg}$) populations were sorted on a FACS Aria (BD Biosciences). Unless specified, CD4$^+$ T cells used in the experiments were Treg-depleted CD4$^+$ T cells and they were sorted as CD4$^+$CD25$^{pos/low}$CD127$^+$. The purity of the sorted CD4$^+$ T cell population was >98% as assessed by CD3 and CD4 staining after sort. CD14$^+$ cells were isolated by positive selection using EasySep™ Human CD14 Positive Selection Kit (StemCell Technologies).

Cell activation and intracellular staining. T populations were stimulated with 1 µg/ml anti-CD3, 1 µg/ml anti-CD28 and 10 U/ml IL-2 in the presence or absence of TLR ligands. At day 4, cells were stimulated with 50 ng/ml phorbol-12-myristate-13-acetate (PMA) and 250 ng/ml ionomycin for 4 hours in the presence of GolgiStop (BD Biosciences) and intracellular staining of cytokines (IFNγ, IL-10, IL-17, IL-4, IL-2) and Foxp3 was performed with Foxp3 staining buffers (eBioscience) per manufacturer's recommendations and the following antibodies: IFNγ (clone 4S.B3) and IL-17 (clone BL168) from Biolegend (San Diego, Calif.), IL-10 (clone JES3-19F1), IFNγ (clone B27) and IL-4 (clone 3010.211), from BD Biosciences and Foxp3 (clone PCH101) from eBioscience. For both extracellular and intracellular stainings, LIVE/DEAD reagent (Molecular Probes) was used to exclude dead cells before surface staining. CD14$^+$ monocytes were culture with different TLR ligands for 24 hours and cell surface staining was performed as described above with an initial FcR blocking step (FcR blocking reagent, human, Miltenyi Biotech). Samples were run on a BD Fortessa instrument and analyzed with FlowJo (TreeStar).

Enzyme-linked immunosorbent assay. ELISA measurement of IFNγ, IL-2, IL-17, IL-4 and IL-10 from stimulated CD4$^+$ T cell culture supernatants and TNFα, IL-1β and IL-6 from CD14$^+$ cultures was performed according to manufacturer's recommendations. IL-2, IL-17 and IL-10 antibody pairs were obtained from R&D, anti-IFNγ monoclonal antibody (MAb) (clone 2G1) and human IFNγ MAb biotin-labeled were from Thermo Scientific, (Rockford, Ill.) and IL-10, IL-6, TNFα and IL-1β antibody pairs were obtained from BD Biosciences.

Quantification of mRNA expression levels by RT-PCR. RNA was isolated using QIAGEN RNeasy Micro Plus Kit (QIAGEN, Valencia, Calif.), following manufacturer's guidelines and converted to cDNA by reverse transcription (RT) with random hexamers and Multiscribe RT (TQMN, Reverse Transcription Reagents; Applied Biosystems, Foster City, Calif.). For mRNA gene expression assays, probes were purchased from Applied Biosystems (Table 2) and the reactions were set up following manufacturer's guidelines and run on a StepOne Real-Time PCR System (Applied Biosystems). Values are represented as the difference in Ct values normalized to β2-microglobulin for each sample as per the following formula: Relative RNA expression=$(2^{-dCt}) \times 1000$.

TABLE 2

TaqMan probes used in this work.

| Probe | Catalog number |
|---|---|
| Il17A | Hs00936345_m1 |
| Il4 | Hs00929862_m1 |
| Ifnγ | Hs00989291_m1 |
| Il10 | Hs00961622_m1 |
| Foxp3 | Hs01085834_m1 |
| Tbet | Hs00203436_m1 |
| Rorc2 | Hs01076112_m1 |
| Gata3 | Hs00231122_m1 |
| Il2 | Hs00914135_m1 |
| Tlr7 | Hs00152971_m1 |
| Tlr8 | Hs00152972_m1 |
| Casp3 | Hs00991554_m1 |
| Cd98 | Hs00374243_m1 |
| Fasl | Hs00181225_m1 |
| Grg4 | Hs00419101_m1 |
| Ikzf1 | Hs00958474_m1 |
| Kmd6b | Hs00996325_g1 |
| Ldha | Hs00855332_g1 |
| Rab10 | Hs00211643_m1 |
| Rgs2 | Hs01009070_g1 |
| Socs2 | Hs00919620_m1 |
| Tnfrsf9 | Hs00155512_m1 |
| Traf5 | Hs00182979_m1 |
| β2m | 4326319E |

Western blotting. Total protein extracts were isolated with M-PER protein extraction kit (Thermo Scientific) and quantified with a BCA kit (Thermo Scientific). 20 µg of protein extract were loaded per lane, separated on a 10% SDS-PAGE gel and transferred to a nitrocellulose membrane.

anti-NFAT1 and anti-β-actin were obtained from Cell Signaling Technology. Anti-pNFAT1 (Ser213/217/229) antibody was obtained from Santa Cruz Biotechnology (Dallas, Tex.). Primary antibodies were detected by secondary anti-rabbit-HRP-conjugated (Cell Signaling Technology) and images were obtained in a CCD camera instrument. Bands were quantified with QuantityOne software.

Intracellular calcium measurements. Ex vivo isolated CD4$^+$ T cells were labeled with 5 μM INDO-1AM for one hour at 37° C. in PBS, 1 mM Ca$^{2+}$. Cells were washed to remove traces of INDO-1AM, resuspended in buffer at 10$^6$ cells/ml and incubated for 30 minutes at 37° C. before analysis. When necessary, IRS661 was added at the indicated concentration during the 30 minute incubation. For acquisition, the sample was acquired for approximately 3 minutes to obtain basal levels of calcium and subsequently IMQ or other reagents were added at the indicated concentrations. Samples were acquired for a minimum of 10 minutes on a BD Fortessa instrument and analysed with FlowJo software.

Gene silencing by lentiviral transduction. Lentiviral particles encoding shRNAs were obtained from Sigma-Aldrich (NFAT1 clone TRCN0000016144, TLR7 clones 3 and 4 TRCN0000056973 and TRCN0000056974, respectively). 5×10$^4$ CD4$^+$ T cells per well were stimulated with plate-bound anti-CD3 (1 μg/ml) and soluble anti-CD28 (1 μg/ml) for 12 h before transduction. Cells were then transduced with viral particles containing a vector expressing the indicated specific shRNA (NFAT1 or TLR7) or a non-target shRNA as a control at a multiplicity of infection of 4. All constructions contained the coding sequence for GFP. After 5 days in culture, transduced cells were sorted based on GFP expression and the efficiency of gene silencing was determined by TaqMan real-time PCR and protein staining.

Preparation of HIV-1 virus stocks. HIV-1 proviral DsRed-tagged DNA pNL-D (derived from the prototype HIV-1 proviral DNA pNL432) was kindly provided by Dr. Yasuko Tsunetsugu-Yokota. 293T cells were used to prepare viral stocks following published protocols with minor modifications. In brief, 293T cells were plated at 0.5×10$^6$/well in 12-well plates and transfected with 2 μg pNL-D using Lipofectamine 2000 (Invitrogen) for 48 hours. Culture supernatant was treated with benzonase (1U/ml) for 30 minutes at 37 C, cleared by filtration and titrated on 293T cells. Stocks were stored at −80 C.

HIV-1 in vitro infection. CD4$^+$ T cells were stimulated with anti-CD3 (1 μg/ml) and anti-CD28 (1 μg/ml) for 48 hours and subsequently infected with HIV-1 at a MOI of 0.001 (concentration within the physiological range). Viability and cytokine secretion was measured every 48 hours for a total of 11 days after infection.

For HIV-1 infection on TLR7-deficient cells, CD4$^+$ T cells were stimulated as above and transduced with the corresponding lentiviral particles. 48 hours after transduction, the cells were infected with HIV-1$_{NL-D}$ at a MOI of 0.001. Viability and frequency of HIV-1-infected cells were measured at different time points by LIVE/DEAD cell dye staining and fixation with 1% PFA (to avoid DsRed signal loss). For intracellular staining after infection, the cells were restimulated with PMA and Ionomycin in the presence of GolgiStop for 4 hours and the staining was performed as recommended by Grupillo et al.

Apoptosis staining. CD4$^+$ T cells were stimulated with anti-CD3 (1 μg/ml) and anti-CD28 (1 μg/ml) for 48 hours and subsequently infected with HIV-1$_{NL-D}$ at a MOI of 0.001. Annexin V and 7-AAD were used to stain for early (Annexin V$^+$7-AAD$^-$) and late (7-AAD$^+$) apoptosis every 24 hours for a total of 11 days.

Statistics. Statistical analysis was performed using GraphPad Prism (GraphPad Software). A standard paired two-tailed t test was used for statistical analysis and a one-way ANOVA with a Tukey's post-test for more than two group comparison, with p values of 0.05 or less considered significant. Data were presented if not indicated elsewhere as mean±s.e.m. (*P<0.05, P<0.005, *P<0.0005).

Mouse experiments. MISTRG mice (Nature Biotechnology 2014; 32; 364-372) were infected with HIV-1 (50 ng p24) at day 0 in the presence of 20 μM IRS661 or control sequence (at either day 0 or day 14). Serum was obtained at different time points and RNA was isolated by Direct-zol RNA MiniPrep kit (Zymo Research). Viral load was measured by Gag amplification by Real Time PCR The Results of the experiments disclosed herein are now described.

While examining the costimulatory role of TLR on CD4$^+$ T cells, it was unexpectedly discovered that entry of CD4$^+$ cells into cell cycle with T cell receptor cross-linking and anti-CD28 was blocked by TLR7 engagement. Specifically, CD4$^+$ T cells were stimulated with anti-CD3 and anti-CD28 in the presence of different TLR agonists followed by analysis of proliferation and cytokine secretion. FIG. 1 shows the effects in CFSE-labeled CD4$^+$ T cells with different TLR ligands when costimulated with anti-CD3 and anti-CD28.

Figure 2:
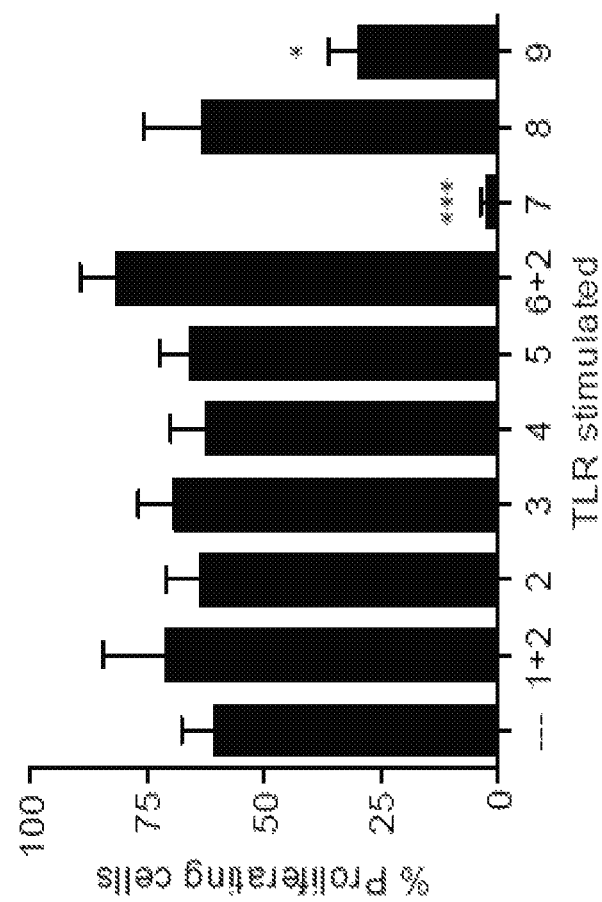
FIG. 2 is a bar graph showing the statistical analysis of the frequency of proliferating $CD4^+$ T cells in 5 experiments ($*P<0.05$, $***P<0.0005$).
Figure 4:
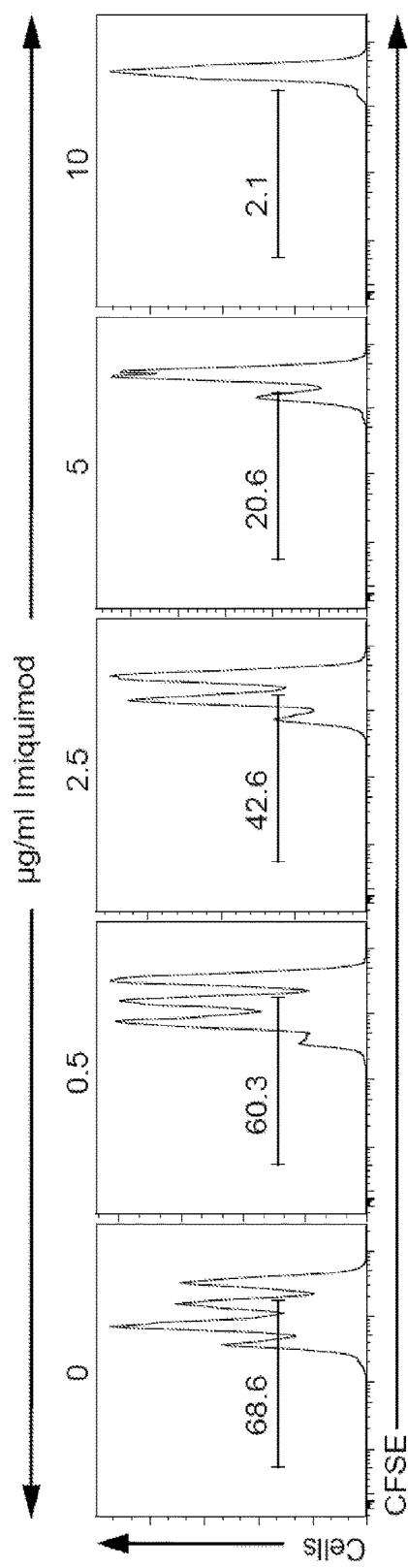
FIG. 4 is a panel of histograms showing CFSE-labeled $CD4^+$ T cell proliferation after 3 days of stimulation. Numbers in histograms represent the frequency of viable proliferating $CD4^+$ T cells.
Figure 5:
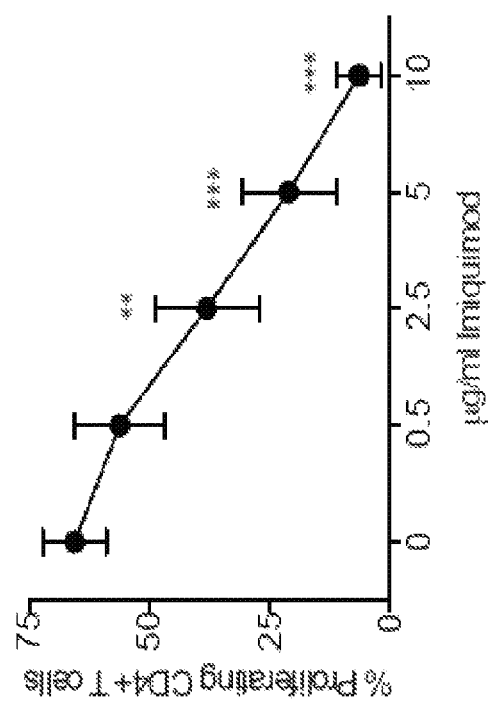
FIG. 5 is a line graph showing the frequency of viable proliferating $CD4^+$ T cells stimulated in the presence of different doses of Imiquimod.
Figure 6:
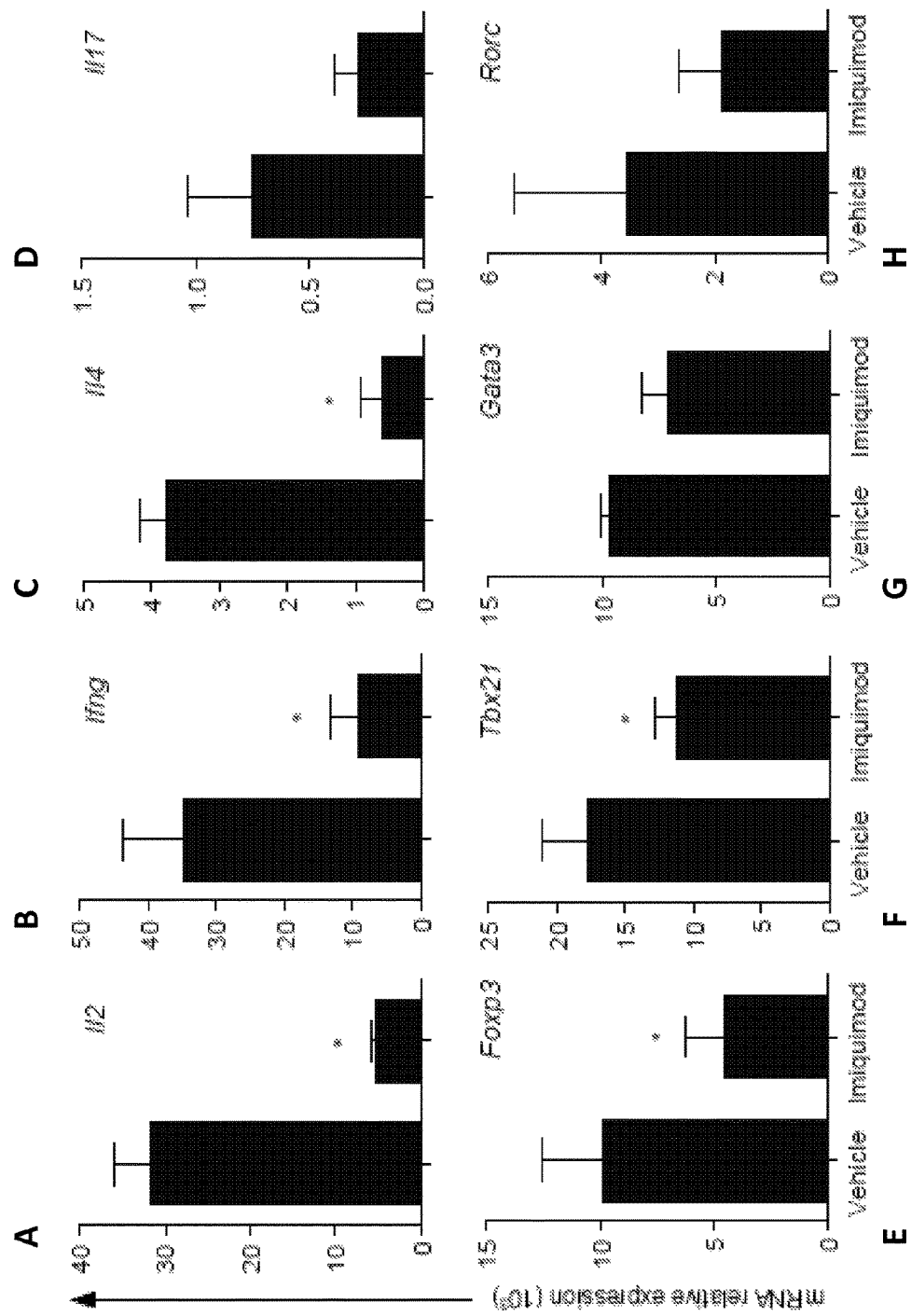
FIG. 6A is a bar graph showing IL-2 RNA gene expression in $CD4^+$ T cells stimulated with anti-CD3 and anti-CD28 in the presence of IMQ or vehicle as control. RNA was isolated after 12 hours and subjected to gene expression analysis by TaqMan real-time PCR. n=3 independent experiments performed. ($*P<0.05$).
FIG. 6B is a bar graph showing IFNγ RNA gene expression in $CD4^+$ T cells stimulated with anti-CD3 and anti-CD28 in the presence of IMQ or vehicle as control ($*P<0.05$).
FIG. 6C is a bar graph showing IL-4 RNA gene expression in $CD4^+$ T cells stimulated with anti-CD3 and anti-CD28 in the presence of IMQ or vehicle as control ($*P<0.05$).
FIG. 6D is a bar graph showing IL-17 RNA gene expression in $CD4^+$ T cells stimulated with anti-CD3 and anti-CD28 in the presence of IMQ or vehicle as control ($*P<0.05$).
FIG. 6E is a bar graph showing FOXP3 RNA gene expression in $CD4^+$ T cells stimulated with anti-CD3 and anti-CD28 in the presence of IMQ or vehicle as control ($*P<0.05$).
FIG. 6F is a bar graph showing TBX21 RNA gene expression in $CD4^+$ T cells stimulated with anti-CD3 and anti-CD28 in the presence of IMQ or vehicle as control ($*P<0.05$).
FIG. 6G is a bar graph showing GATA3 RNA gene expression in $CD4^+$ T cells stimulated with anti-CD3 and anti-CD28 in the presence of IMQ or vehicle as control ($*P<0.05$).
FIG. 6H is a bar graph showing RORC RNA gene expression in $CD4^+$ T cells stimulated with anti-CD3 and anti-CD28 in the presence of IMQ or vehicle as control ($*P<0.05$).
Figure 7A:
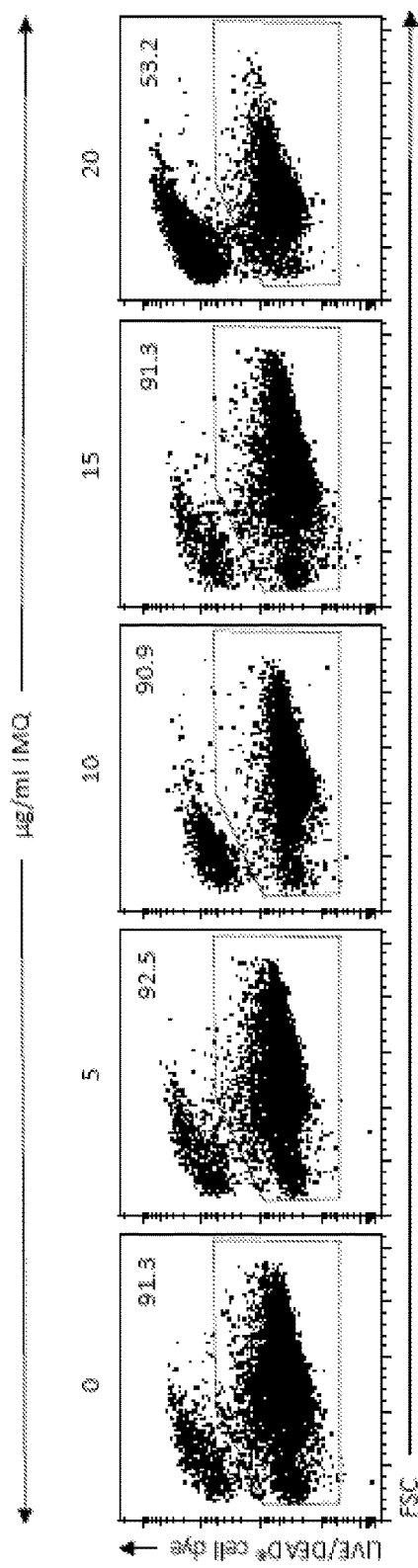
FIG. 7A is a panel of histograms showing cell viability of $CD4^+$ T cells stimulated with anti-CD3 and anti-CD28 in the presence of different doses of IMQ for 4 days.
Figure 7B:
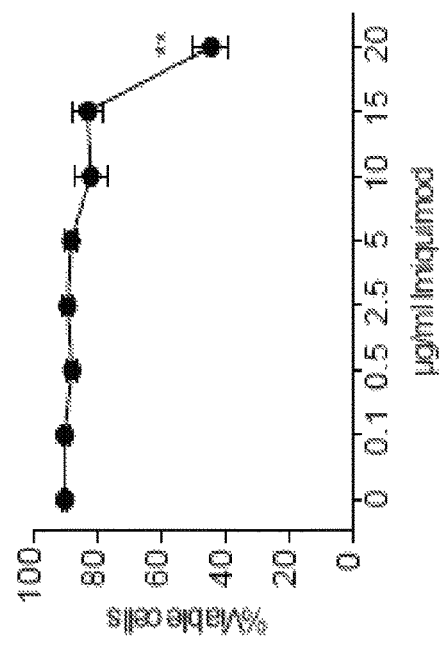
FIG. 7B shows the statistical analysis of four cell viability experiments performed ($**P<0.005$).

Imiquimod (IMQ) dramatically reduced the proliferation of CD4$^+$ cells (FIG. 2) as well as the secretion of IFNγ (FIG. 3A) and IL-17 (FIG. 3B) as compared to control cells in a dose-dependent fashion. TLR7 signaling inhibited proliferation (FIGS. 4 and 5) and cytokine secretion on CD4$^+$ T cells when stimulated for 4 days in the presence of different doses of Imiquimod. This inhibitory effect was observed as soon as 12 hours after activation, with a significant decrease in the induction of IL-2 (FIG. 6A), IFNγ (FIG. 6B) and IL-4 (FIG. 6C) gene expression with IMQ treatment (FIGS. 6A-6H). While a decrease in proliferation, concentrations up to 15 μg/ml IMQ had no effect on cell viability (FIGS. 7A-7B).

Figure 8:
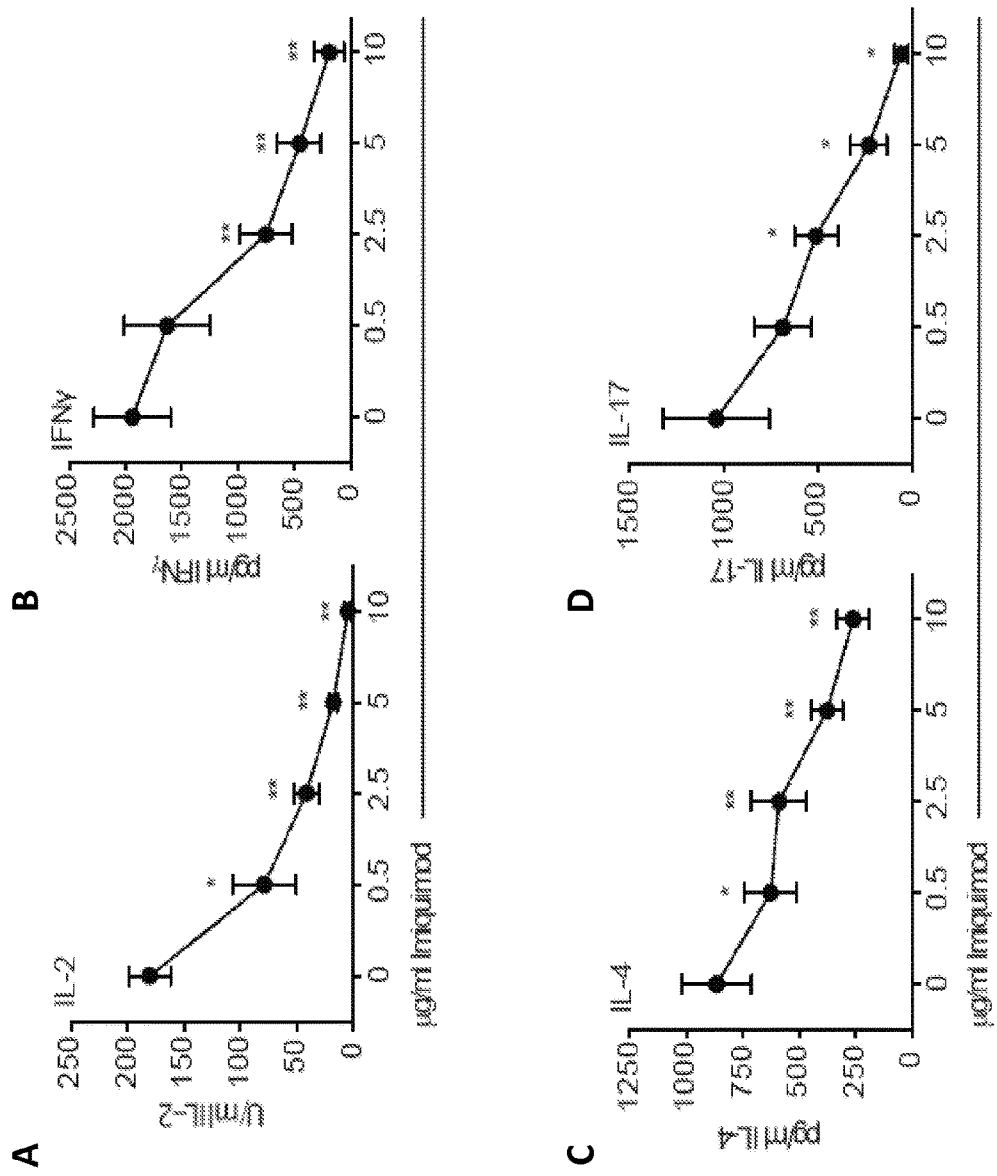
FIG. 8A shows IL-2 secretion measured by ELISA after 3 days.
FIG. 8B shows IFN' secretion measured by ELISA after 3 days.
FIG. 8C shows IL-4 secretion measured by ELISA after 3 days.
FIG. 8D shows IL-17 secretion measured by ELISA after 3 days.
Figure 9A:
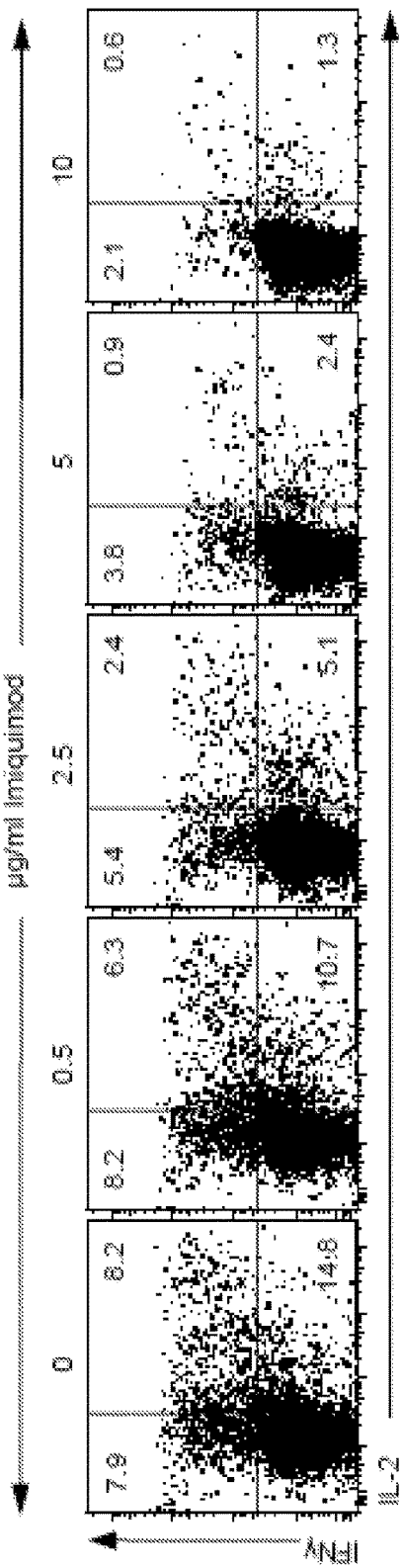
FIG. 9A is a panel of histograms showing intracellular staining of IL-2 and IFN' after a 4 hour PMA and ionomycin stimulation at day four. E. Frequency of cytokine-producing $CD4^+$ T cells. Statistical analyses represent mean±s.e.m. of five independent experiments performed. $*p<0.05$, $p<0.005$, $*p<0.0005$.
Figure 9B:
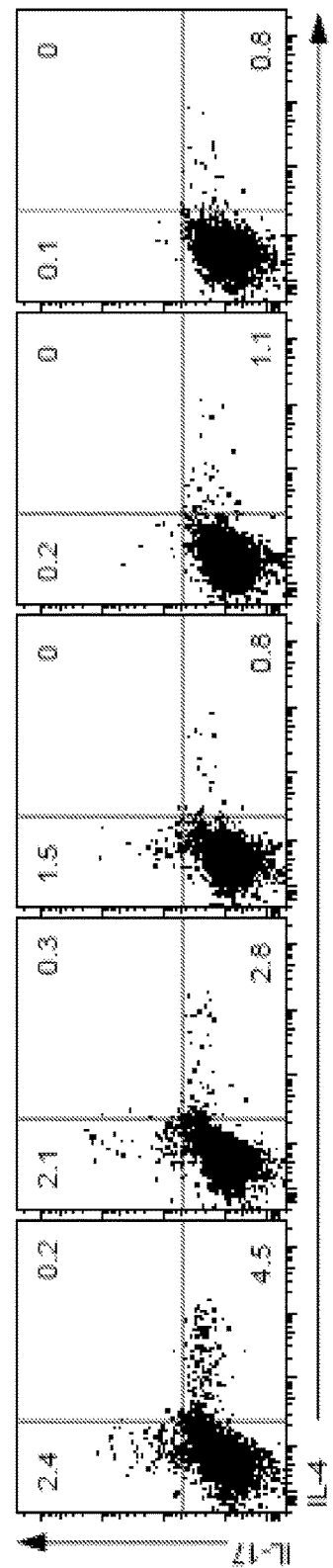
FIG. 9B is a panel of histograms showing intracellular staining of IL-4 and IL-17 after a 4 hour PMA and ionomycin stimulation at day 4.
Figures 10A, 10B:
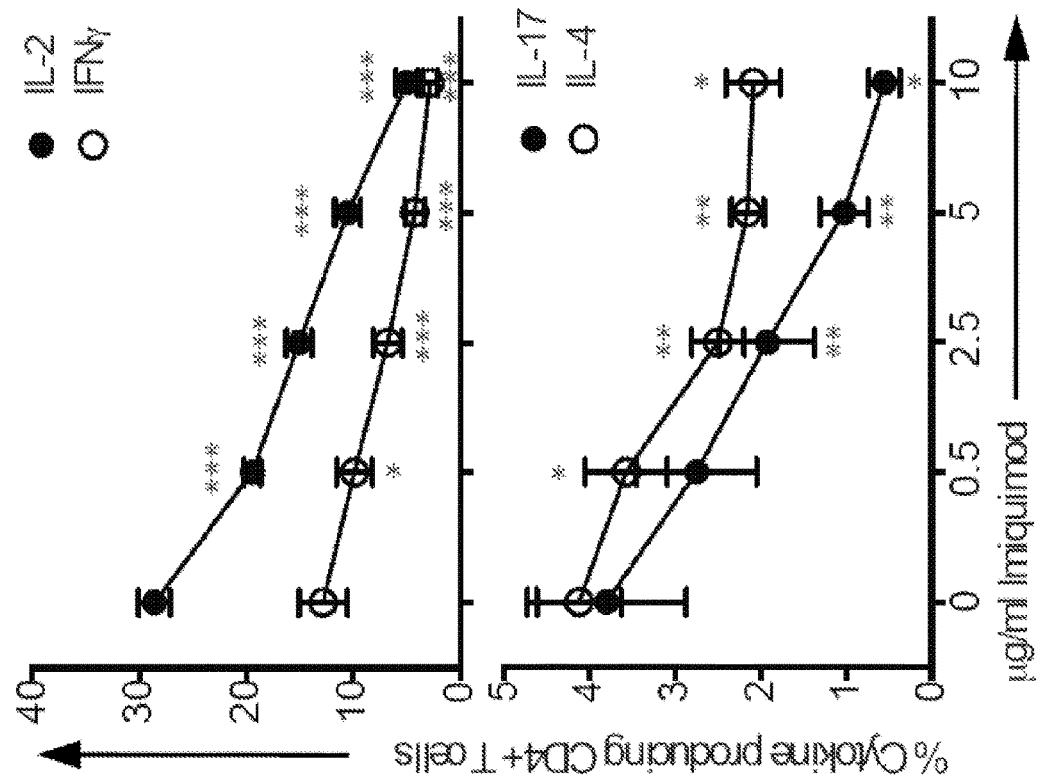
FIG. 10A is a line graph showing the frequency of IL-2- and IFNγ-producing $CD4^+$ T cells. Statistical analyses represent mean±s.e.m. of five independent experiments performed, $*p<0.05$, $p<0.005$, $*p<0.0005$.
FIG. 10B is a line graph showing the frequency of IL-17- and IL-4-producing $CD4^+$ T cells. Statistical analyses represent mean±s.e.m. of five independent experiments performed, $*p<0.05$, $p<0.005$, $*p<0.0005$.
Figure 10C:
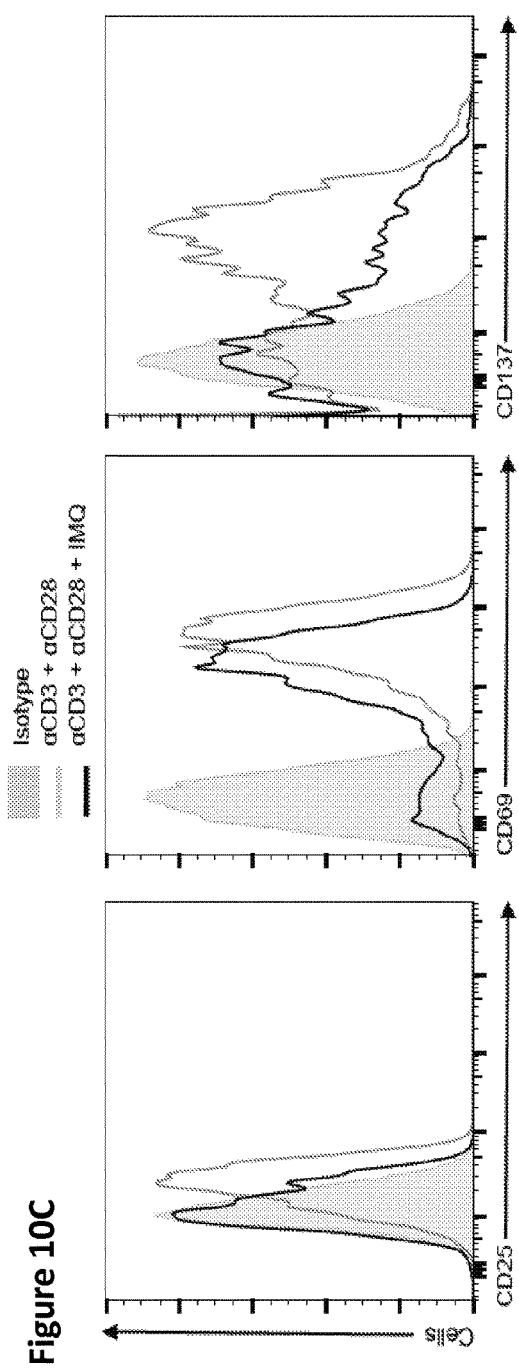
FIG. 10C is a panel of graphs showing $CD4^+$ T cell stimulation in the presence of IMQ inhibited the expression of activation markers such as CD25, CD69 and CD137, measured 48 hours after activation.
Figure 10D:
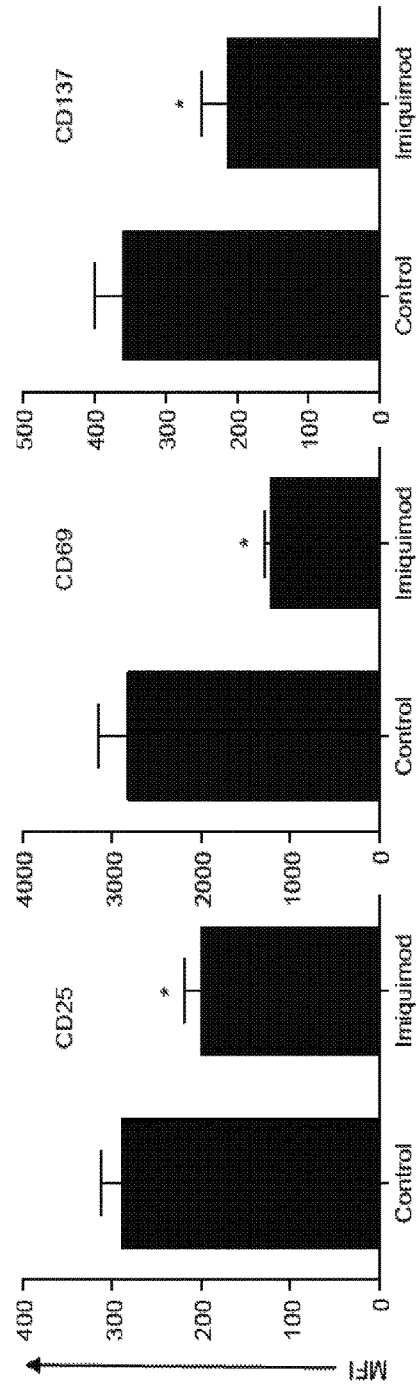
FIG. 10D is a panel of graphs showing $CD4^+$ T cell stimulation in the presence of IMQ inhibited the expression of activation markers such as CD25, CD69 and CD137, measured 48 hours after activation.

The decrease in proliferation also correlated with a decrease in the secretion of the inflammatory cytokines IFNγ (FIG. 8B), IL-17 (FIG. 8D), IL-2 (FIG. 8A) and IL-4 (FIG. 8C) as measured by ELISA at day 3 after stimulation. This reduction on cytokine secretion was confirmed at a single cell level (FIGS. 9A-9B), as the frequency of cytokine-producing cells was also diminished in a dose-dependent manner with increasing doses of IMQ in the cultures (FIGS. 10A-10B). Furthermore, CD4$^+$ T cell stimulation in the presence of IMQ inhibited the expression of activation markers such as CD25, CD69 and CD137, measured 48 hours after activation (FIGS. 10C-10D).

Figure 11A:
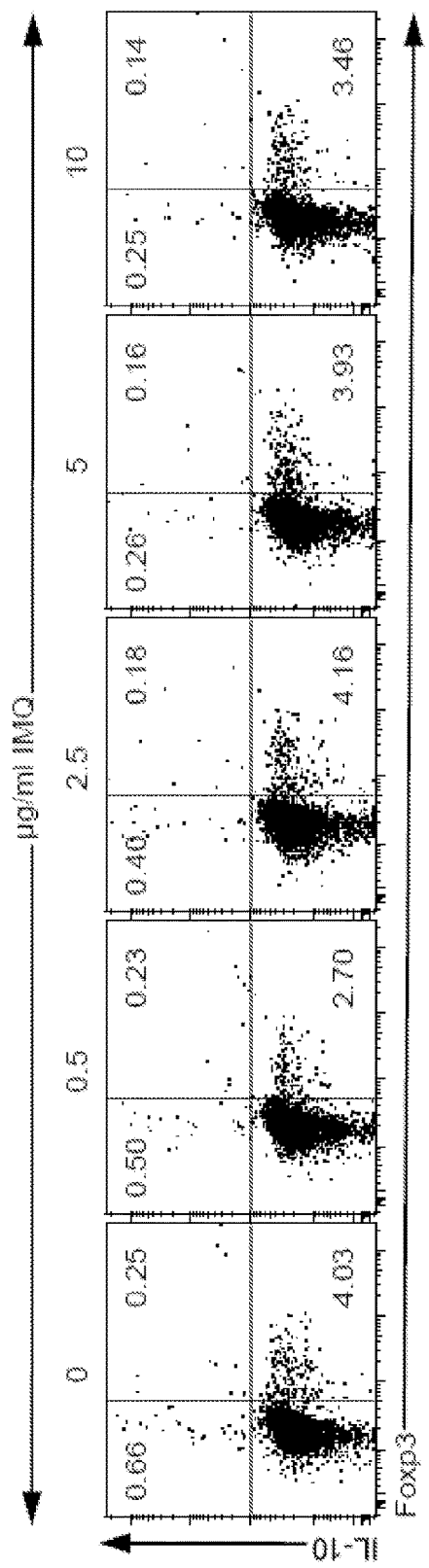
FIG. 11A is a panel of histograms showing the frequency of IL-10 producing cells versus Foxp3 expression at day 4 of $CD4^+$ T cells stimulated with different doses of IMQ and sorted after a 4-hour stimulation with PMA and ionomycin.
Figure 11:
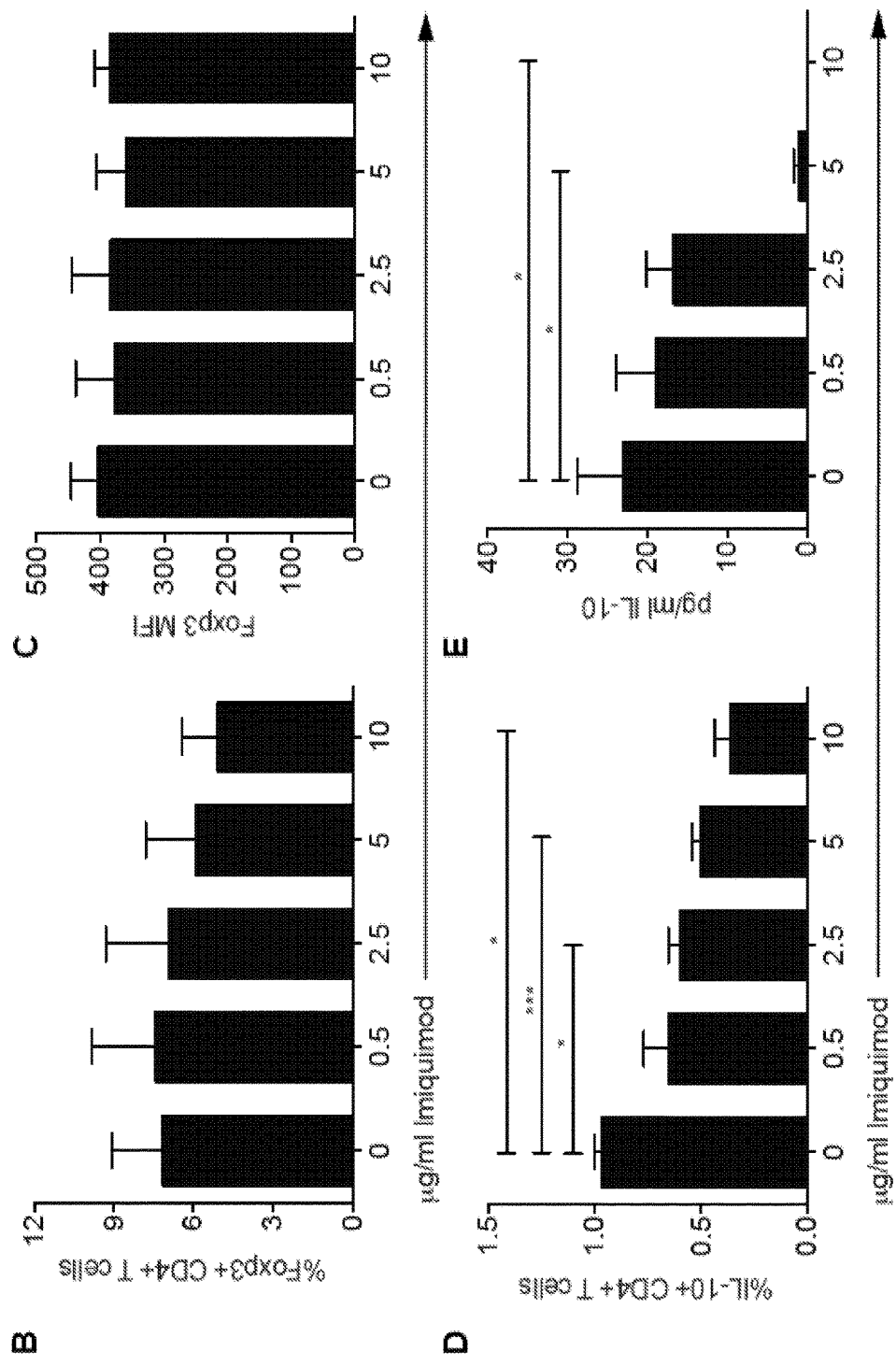
FIG. 11B shows the statistical analysis of the frequency of $Foxp3^+$ cells in three independent experiments performed.
FIG. 11C shows the statistical analysis of the frequency of Foxp3 MFI in three independent experiments performed.
FIG. 11D shows the statistical analysis of frequency of $IL-10^+$ cells (n=3).
FIG. 11E shows the statistical analysis of IL-10 secretion as measured by ELISA at day 3 after activation (n=3).

The effect of IMQ was not associated with the conversion of CD4$^+$ T cells into a regulatory T cell population (FIG. 11A), as neither Foxp3 expression (FIG. 11B-11C) or IL-10 secretion was increased in the presence of IMQ (FIG. 11E). The unresponsive phenotype observed was not due to an indirect effect of TLR7 on Tregs, as the same results were obtained with sorted Treg-depleted CD4$^+$ T cells. Only TLR9 stimulation with ODN2006 also decreased the frequency of proliferating CD4$^+$ T cells, but to a lesser extent (FIG. 1).

Figure 12A:
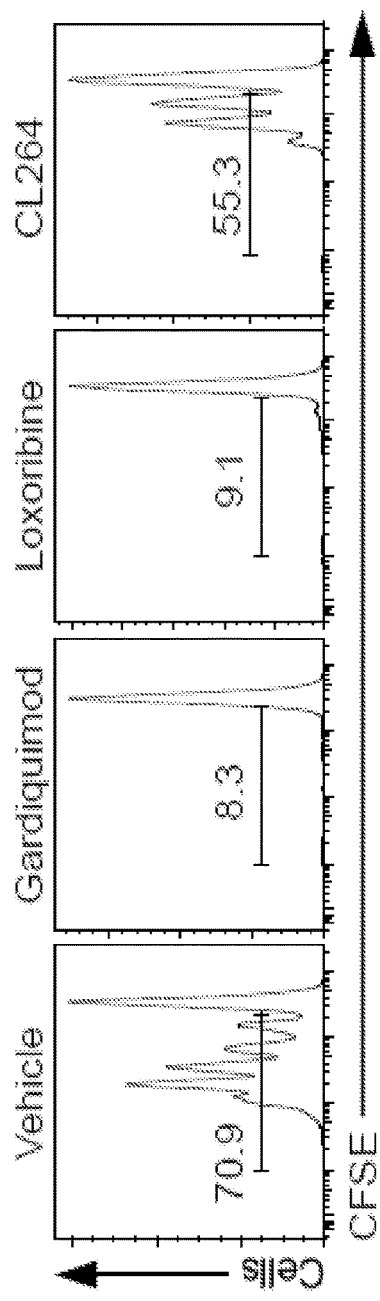
FIG. 12A is a panel of histograms showing CFSE-labeled $CD4^+$ T cell proliferation three days after stimulation with vehicle, GDQ, Loxoribine, or CL264. Numbers in histograms represent the frequency of viable proliferating $CD4^+$ T cells. Statistical analysis represents mean±s.e.m. of five independent experiments performed.
Figure 12B:
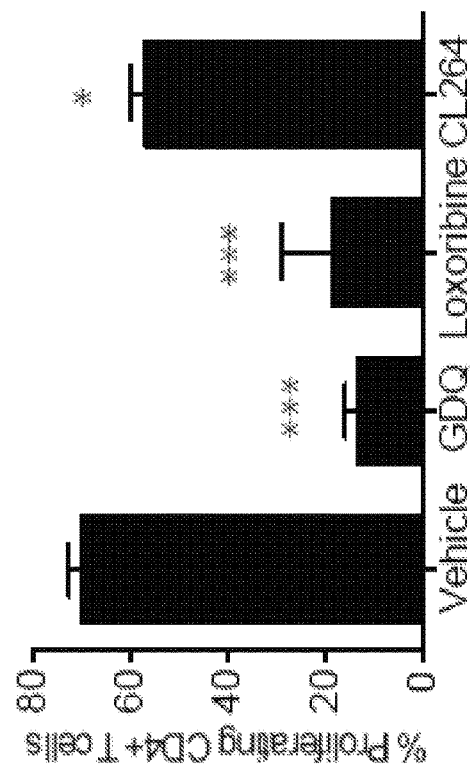
FIG. 12B is a bar graph showing the frequency of viable proliferating $CD4^+$ T cells. Statistical analysis represents mean±s.e.m. of five independent experiments performed, $*p<0.05$, $***p<0.0005$.

To confirm the specificity of the results, CD4$^+$ T cells were stimulated in the presence of other TLR7 ligands, such as Loxoribine (Loxo), CL264, or Gardiquimod (GDQ) (FIG. 12A). The three ligands tested induced a significant decrease in CD4$^+$ T cell proliferation as compared to the control (FIG.

Figure 13:
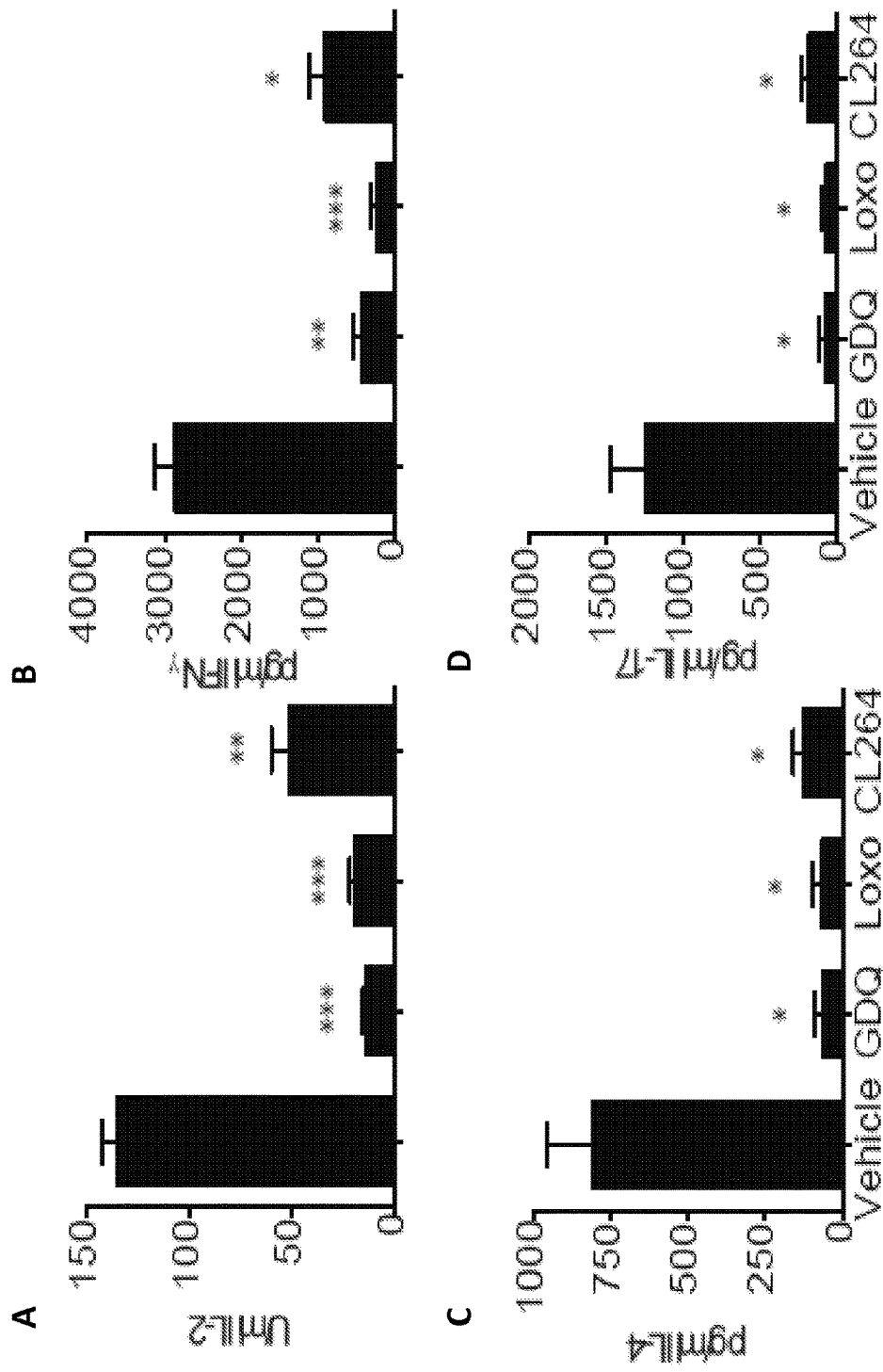
FIG. 13A shows IL-2 secretion measured by ELISA after 3 days. Statistical analysis represents mean±s.e.m. of five independent experiments performed, $*p<0.05$, $p<0.005$, $*p<0.0005$.
FIG. 13B shows IFNγ secretion measured by ELISA after 3 days. Statistical analysis represents mean±s.e.m. of five independent experiments performed, $*p<0.05$, $p<0.005$, $*p<0.0005$.
FIG. 13C shows IL-4 secretion measured by ELISA after 3 days. Statistical analysis represents mean±s.e.m. of five independent experiments performed, *p<0.05, p<0.005, *p<0.0005.
FIG. 13D shows IL-17 secretion measured by ELISA after 3 days. Statistical analysis represents mean±s.e.m. of five independent experiments performed, *p<0.05, p<0.005, *p<0.0005.
Figure 14:
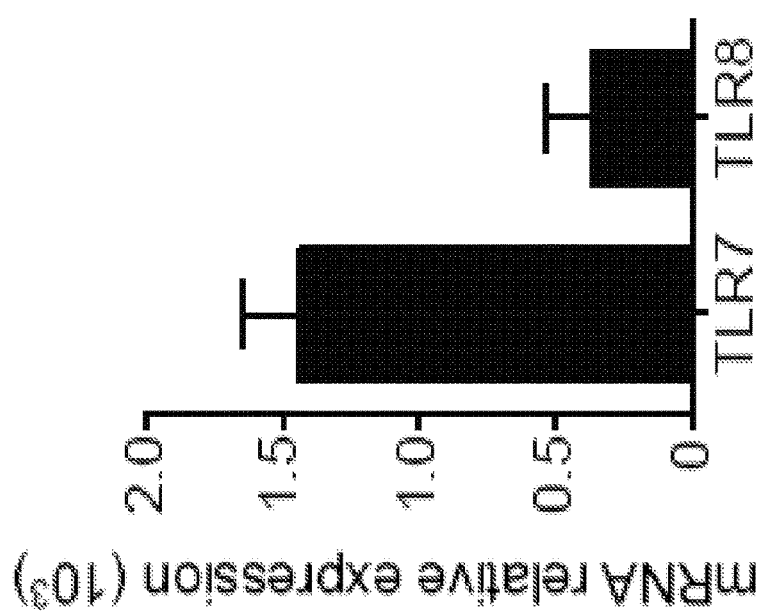
FIG. 14 shows the relative RNA gene expression of TLR7 and TLR8 in sorted CD4$^+$ T cells (n=3).
Figure 15:
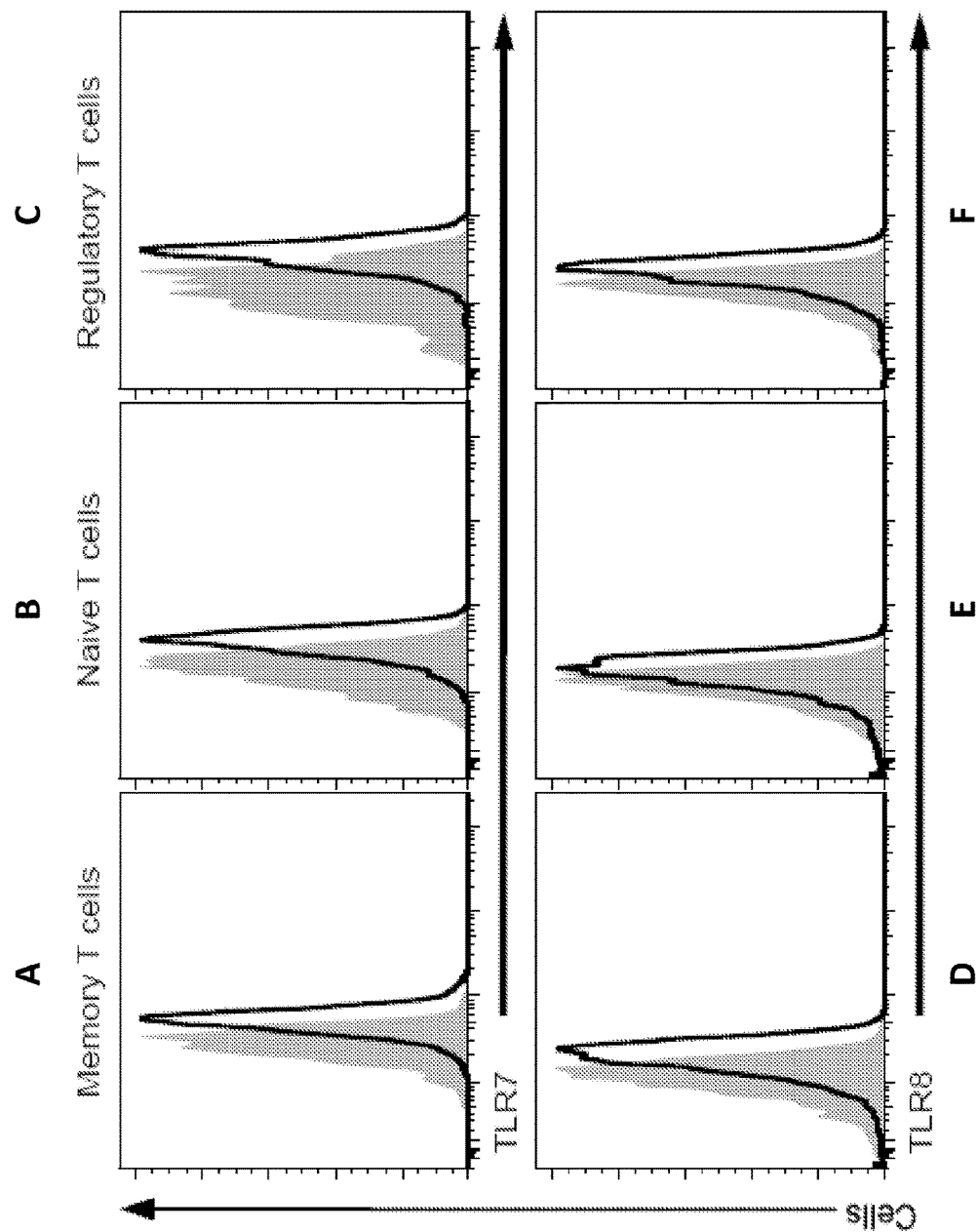
FIG. 15A shows a representative example of 4 independent experiments performed on CD4$^+$ T cell isotypes stained for TLR7 and TLR8.
FIG. 15B shows a representative example of 4 independent experiments performed on CD4$^+$ T cell isotypes stained for TLR7 and TLR8.
FIG. 15C shows a representative example of 4 independent experiments performed on CD4$^+$ T cell isotypes stained for TLR7 and TLR8.
FIG. 15D shows a representative example of 4 independent experiments performed on CD4$^+$ T cell isotypes stained for TLR7 and TLR8.
FIG. 15E shows a representative example of 4 independent experiments performed on CD4$^+$ T cell isotypes stained for TLR7 and TLR8.
FIG. 15F shows a representative example of 4 independent experiments performed on CD4$^+$ T cell isotypes stained for TLR7 and TLR8.

12B), with GDQ and Loxoribine inhibiting proliferation to levels comparable to IMQ treatment. IL-2 (FIG. 13A), IFNγ (FIG. 13B), IL-4 (FIG. 13C) and IL-17 (FIG. 13D) secretion was also inhibited after stimulation in the presence of each of the three ligands, as measured by ELISA after three days in culture.

Figure 16:
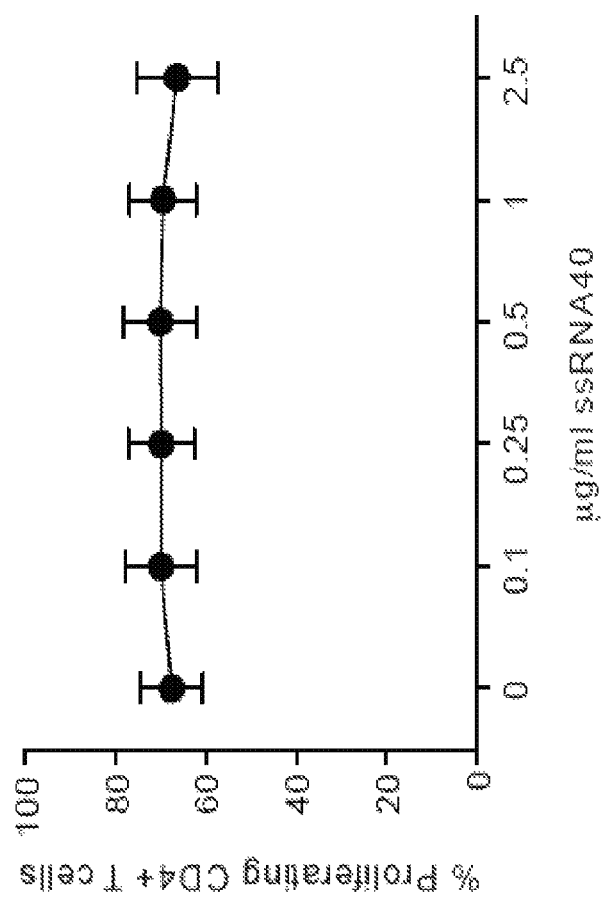
FIG. 16 shows the frequency of proliferating CD4$^+$ T cells with increasing concentrations of ssRNA40 (n=4). CFSE-labeled CD4$^+$ T cells were stimulated with anti-CD3 and anti-CD28 in the presence of different doses of ssRNA40.
Figure 17:
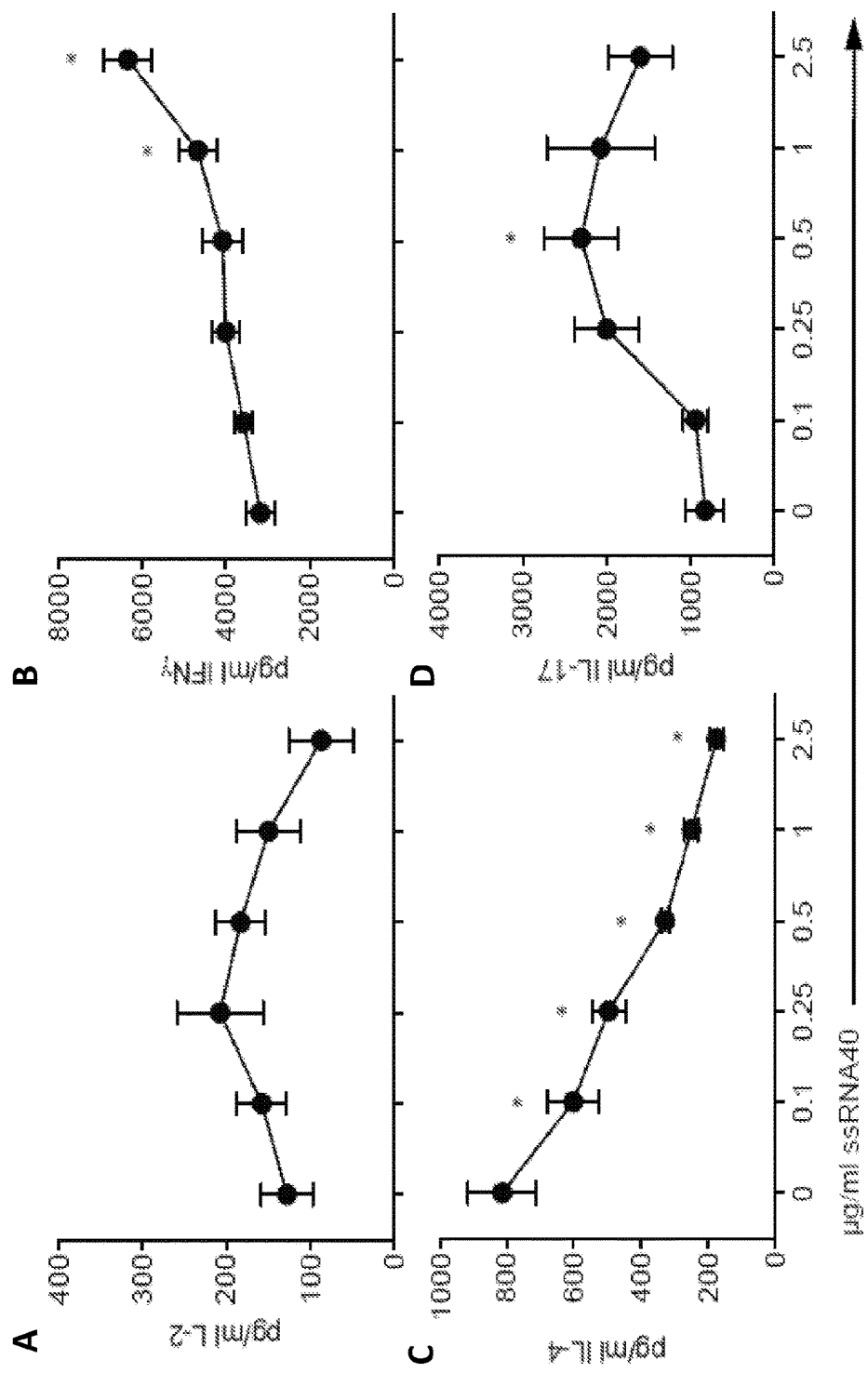
FIG. 17A is a graph showing TLR8 signaling does not inhibit IL-2 secretion of CD4+ T cells, secretion measured at day 3 after activation (n=4).
FIG. 17B is a graph showing TLR8 signaling does not inhibit IFNγ secretion of CD4+ T cells, secretion measured at day 3 after activation (n=4).
FIG. 17C is a graph showing TLR8 signaling does not inhibit IL-4 secretion of CD4+ T cells, secretion measured at day 3 after activation (n=4).
FIG. 17D is a graph showing TLR8 signaling does not inhibit IL-17 secretion of CD4+ T cells, secretion measured at day 3 after activation (n=4).

Both TLR7 and TLR8 are expressed in human CD4$^+$ T cell subpopulations (FIGS. 14 and 15A-F), but interestingly, although reports in the literature suggest that both TLR7 and TLR8 recognize single-stranded RNA as their natural ligand in APC, no such effect was observed when the TLR8 ligand (ssRNA40/LyoVec) was used in these experiments. Instead, T cell stimulation in the presence of ssRNA40 significantly increased the production of IFNγ and inhibited the secretion of IL-4 by CD4$^+$ T cells (FIGS. 17A-17D), showing no effect on proliferation (FIG. 16). These data are in agreement with a previous report and suggest that despite sharing ligands, the signaling pathways that TLR7 and TLR8 trigger on CD4$^+$ T cells lead to different phenotypic outcomes.

Figure 18:
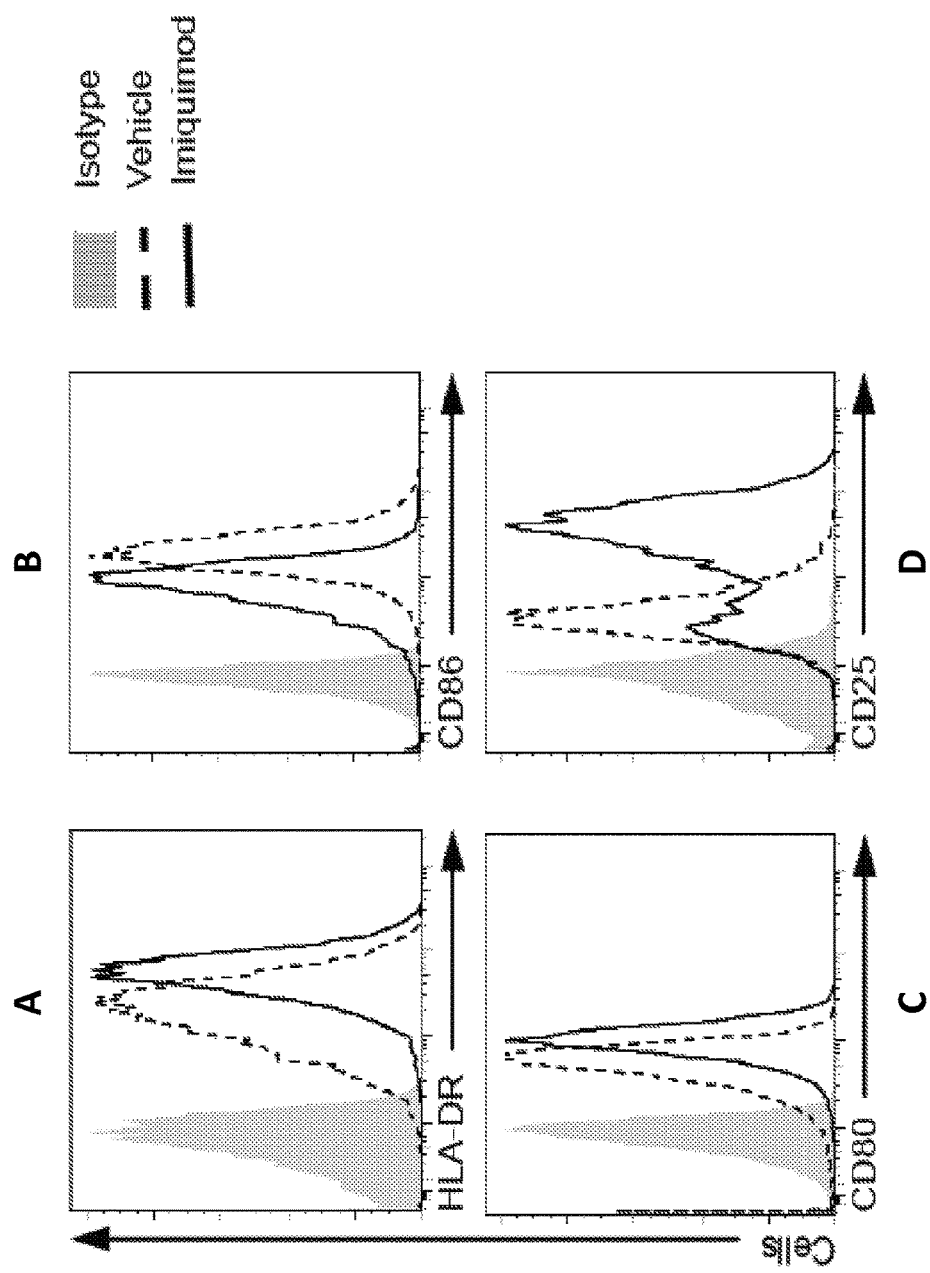
FIG. 18A shows surface staining of HLA-DR of CD14$^+$ monocytes were stimulated with 5 μg/ml IMQ or vehicle for 24 hours.
FIG. 18B shows surface staining of CD86 of CD14$^+$ monocytes were stimulated with 5 μg/ml IMQ or vehicle for 24 hours.
FIG. 18C shows surface staining of CD80 of CD14$^+$ monocytes were stimulated with 5 μg/ml IMQ or vehicle for 24 hours.
FIG. 18D shows surface staining of CD25 of CD14$^+$ monocytes were stimulated with 5 μg/ml IMQ or vehicle for 24 hours.
Figure 19:
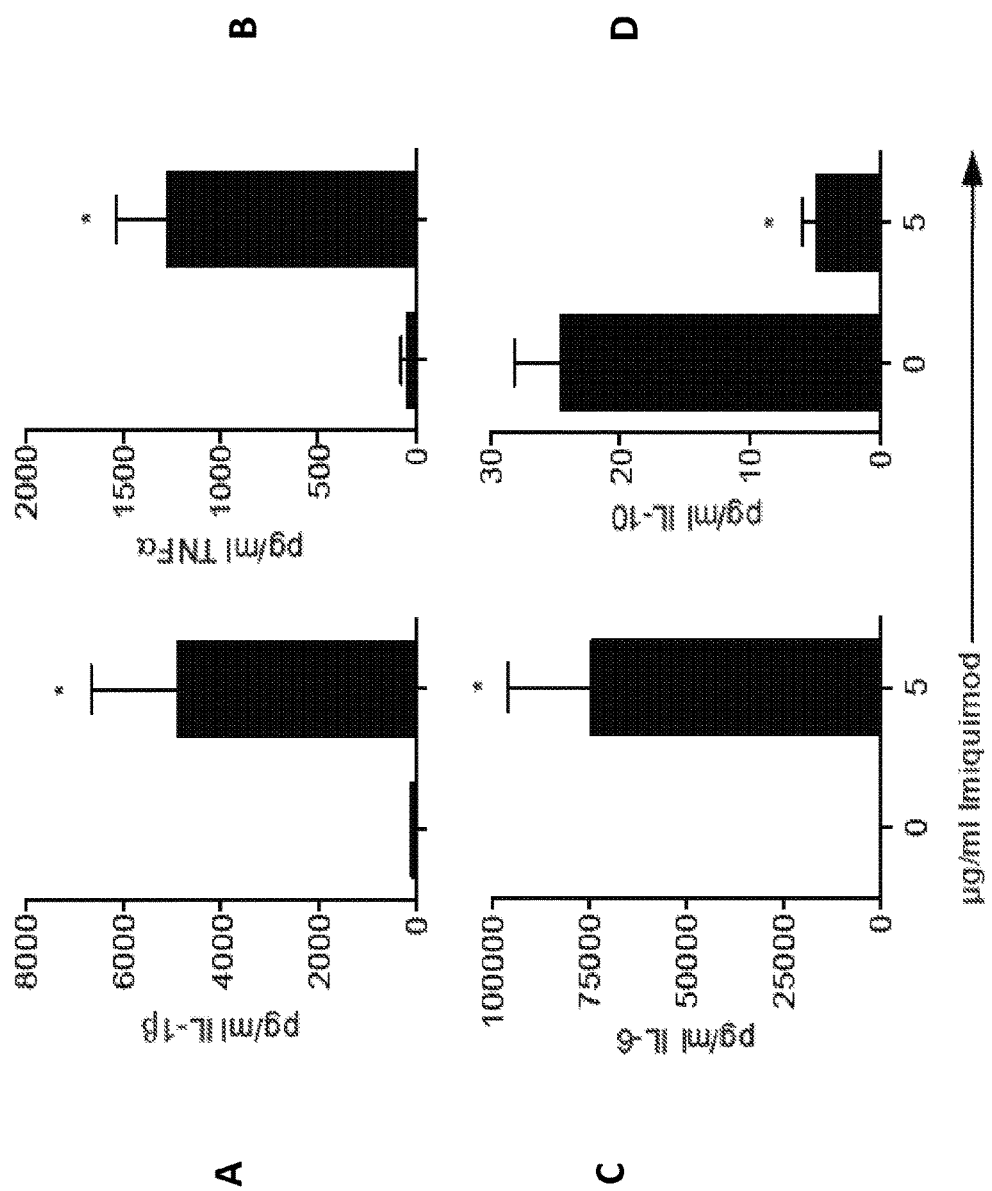
FIG. 19A shows IL-1β secretion as measured by ELISA (n=5).
FIG. 19B shows TNFα secretion as measured by ELISA (n=5).
FIG. 19C shows IL-6 secretion as measured by ELISA (n=5).
FIG. 19D shows IL-10 secretion as measured by ELISA (n=5).

TLR7 ligation has been shown to induce the activation/maturation of APC, with upregulation of activation markers and secretion of proinflammatory cytokines. In agreement with published data, CD14$^+$ monocytes isolated from the same donors stimulated in the presence or absence of IMQ showed an activated phenotype, with upregulation of HLA-DR (FIG. 18A), CD80 (FIG. 18C) and CD25 (FIG. 18D), and downregulation of CD86 (FIG. 18B) protein expression. Upon IMQ stimulation, CD14$^+$ monocytes also secreted significant levels of the pro-inflammatory cytokines IL-6 (FIG. 19C), TNFα (FIG. 19B) and IL-113 (FIG. 19A) and decreased IL-10 (FIG. 19D) secretion, suggesting that IMQ stimulation on CD4$^+$ T cells and CD14$^+$ monocytes leads to completely different outcomes.

Figure 20A:
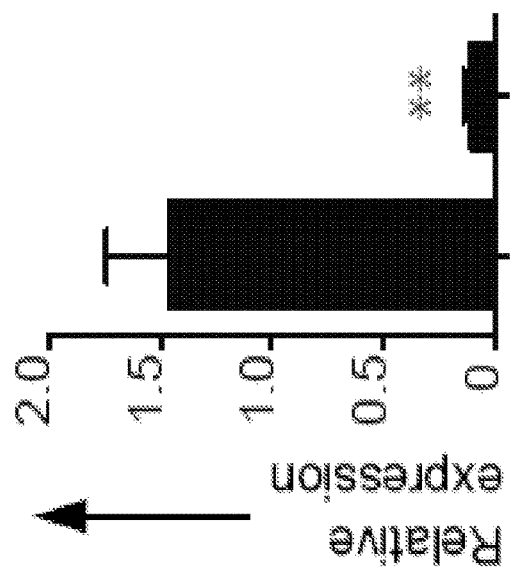
FIG. 20A is a bar graph showing TLR7 expression in CD4$^+$ T cells stimulated in the presence of a shRNA specific for TLR7 or a non-target control. Statistical analysis represents mean±s.e.m. of four independent experiments performed, **p<0.005.
Figure 20B:
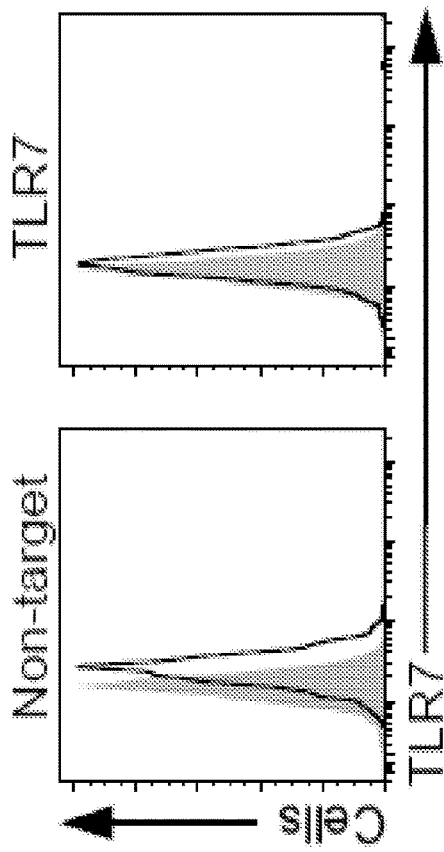
FIG. 20B are histograms of transduced cells sorted for GFP expression at day 5 and TLR7 protein expression. Histograms represent isotype control (grey histograms) and TLR7 (open histograms).
Figure 21A:
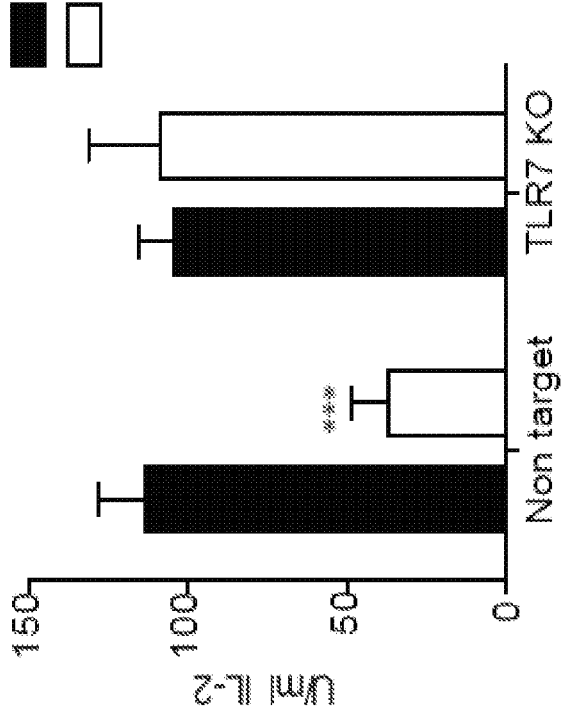
FIG. 21A is a bar graph showing non-target and TLR7 shRNA-transduced (KO) CD4$^+$ T cells stimulated in the presence (white bars) or absence (black bars) of IMQ for 3 days and IL-2 secretion measured by ELISA. Statistical analysis represents mean±s.e.m. of four independent experiments, **p<0.005.
Figure 21B:
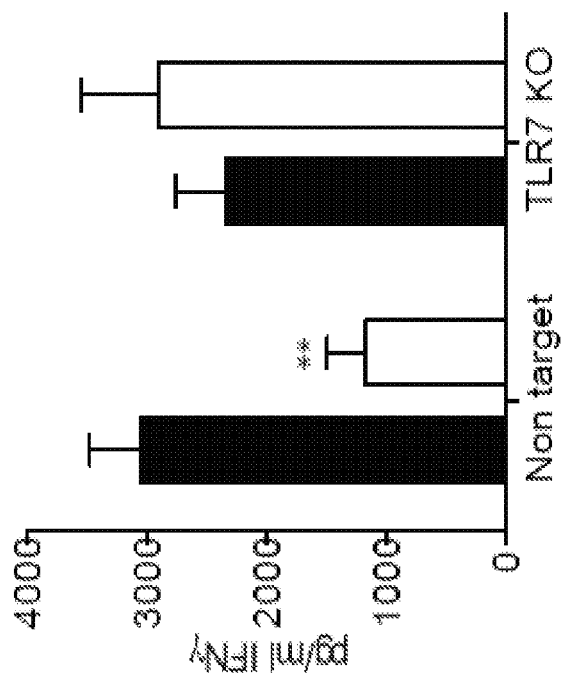
FIG. 21B is a bar graph showing non-target and TLR7 shRNA-transduced (KO) CD4$^+$ T cells stimulated in the presence (white bars) or absence (black bars) of IMQ for 3 days and IFNγ secretion measured by ELISA. Statistical analysis represents mean±s.e.m. of four independent experiments, ***p<0.0005.

To confirm the specificity of the unresponsive phenotype driven by TLR7 signaling, CD4$^+$ T cells were stimulated in the presence of a shRNA specific for TLR7 or a non-target shRNA as control. After 5 days of culture, we confirmed that protein and RNA silencing efficiency was >80% (FIGS. 20A-20B). Resting TLR7-silenced CD4$^+$ T cells were stimulated with anti-CD3 and anti-CD28 in the presence or absence of IMQ and IL-2 and IFNγ secretion was measured. While CD4$^+$ T cells transduced with a non-target shRNA showed a decrease in the production of IL-2 (FIG. 21A) and IFNγ (FIG. 21B) secretion with IMQ, this effect was abolished when the cells expressed a shRNA specific for TLR7, confirming that the unresponsive state observed in T cells in the presence of IMQ is TLR7-specific.

The inhibition of proliferation and cytokine secretion and activation by CD4$^+$ T cells upon stimulation in the presence of TLR7 ligands resembled the unresponsive phenotype that characterizes clonal anergy. T cell anergy, along with regulatory T cells, are the major mechanisms of peripheral T cell tolerance. Different model systems have been used to induce clonal anergy, including treatment with the calcium ionophore ionomycin. The activation of calcium signaling in the absence of activating signals in costimulatory signaling pathways is common in all these models. Thus, the main characteristic of an anergizing stimulus is its ability to induce an increase in intracellular calcium concentrations.

Figure 22:
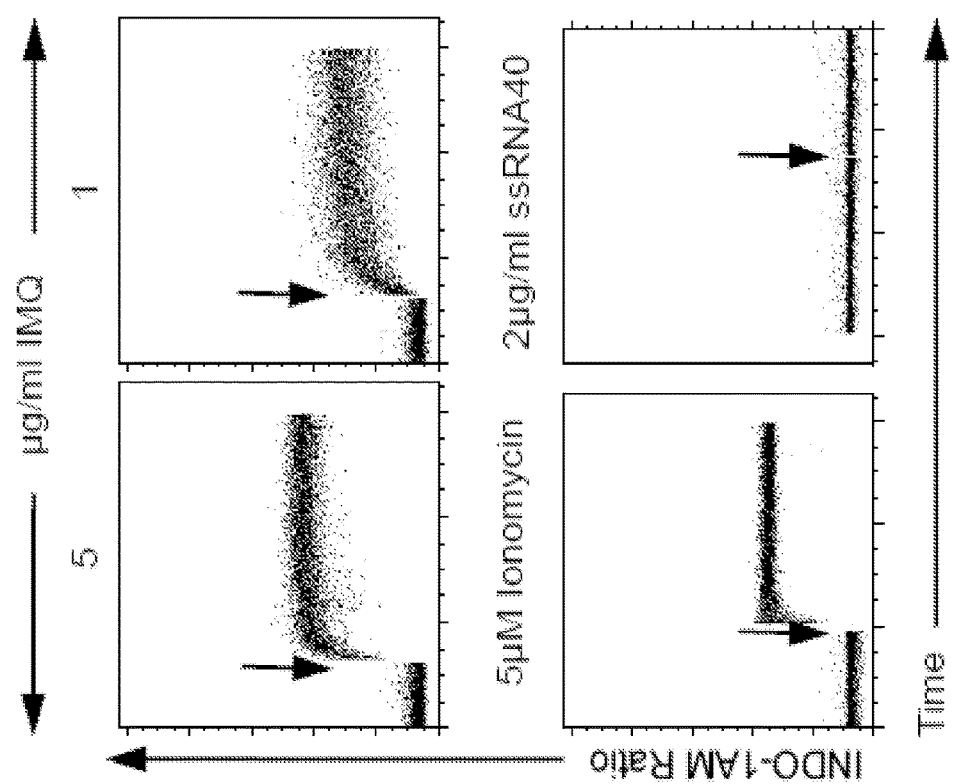
FIG. 22 is a panel of histograms showing calcium fluxes as measured by INDO-1AM ratio over time on CD4$^+$ T cells stimulated with two doses of IMQ (upper), ionomycin (lower left) or ssRNA40/LyoVec (lower right). Arrows indicate the addition of IMQ.
Figure 23B:
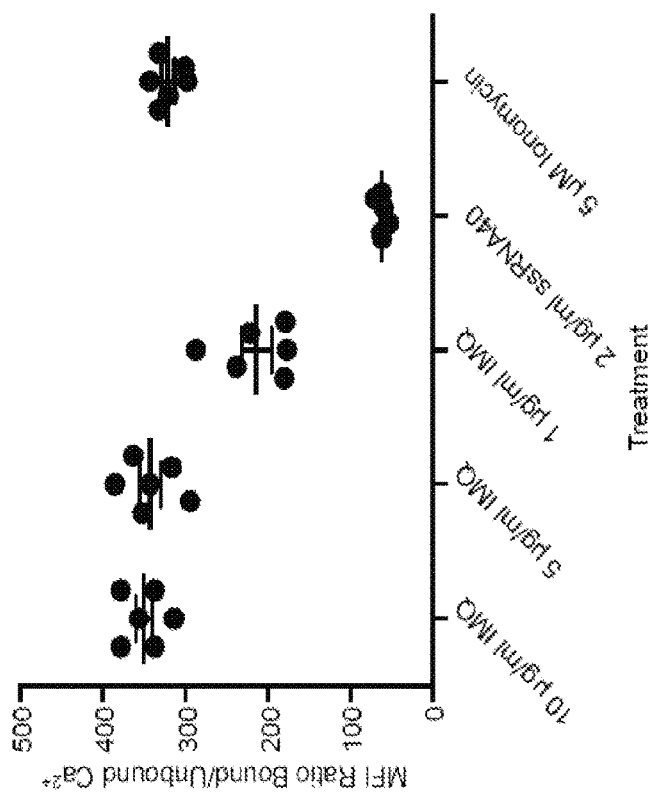
FIG. 23B is a graph showing the increase in intracellular calcium concentration in a dose-dependent manner that was TLR7-specific, the increase in calcium concentration upon IMQ stimulation.
Figure 23A:
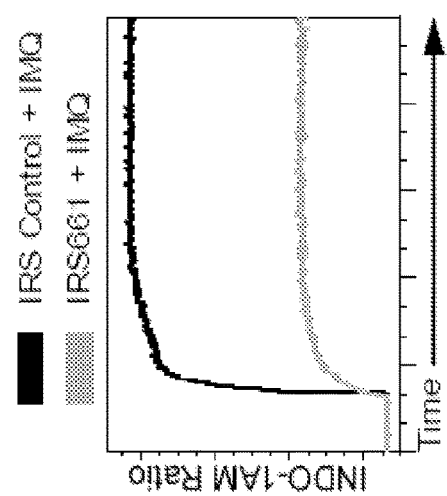
FIG. 23A shows the calcium flux in CD4$^+$ T cells pre-incubated with a control sequence (black) or a specific TLR7 inhibitory sequence (IRS661, grey) and stimulated with IMQ.

To test the hypothesis that TLR7 signaling on CD4$^+$ T cells was inducing clonal anergy, sorted CD4$^+$ T cells were stained with INDO-1AM and treated with different doses of IMQ (FIG. 22). IMQ induced a significant and sustained (maintained for at least 20 minutes, FIGS. 23A and 23B) increase in intracellular calcium concentration in a dose-dependent manner that was TLR7-specific, as preventing TLR7 signaling with the specific inhibitory sequence IRS661 impaired the increase in calcium concentration upon IMQ stimulation (FIGS. 23A and 23B). The increase in intracellular calcium concentration was not observed when the cells were stimulated with a TLR8 agonist (FIG. 22) or other ligands for intracellular TLR (Poly(I:C) for TLR3 (FIG. 24A) and ODN2006 for TLR9 (FIG. 24B). As a positive control, cells were treated with ionomycin, which has been used as an anergy-inducing agent in in vitro experiments (FIG. 22).

An immediate consequence of increased concentration of intracellular calcium is the activation of the nuclear factor of activated T-cells (NFAT1), a transcription factor that is highly phosphorylated in resting cells and becomes dephosphorylated by the calcium/calmodulin-dependent phosphatase calcineurin when the concentration of intracellular calcium is increased. To examine whether IMQ stimulation induced the dephosphorylation of NFAT1, we stimulated CD4$^+$ T cells with IMQ and purified total protein extracts at 0, 45 and 90 minutes (FIG. 25A). Western blot analysis with an anti-NFAT1 antibody showed that IMQ dephosphorylated NFAT1, and these results were confirmed using a phospho-specific anti-NFAT antibody with total extracts from CD4$^+$ T cells stimulated with IMQ for 40 minutes (FIG. 25B).

NFAT translocates to the nucleus with dephosphorylation where it becomes transcriptionally active. This NFAT translocation to the nucleus in the absence of concomitant costimulation signal leads to the transcription of a set of NFAT-dependent, anergy-related genes that are different from those upregulated with full activation in the presence of a costimulatory signal.

Figure 26A:
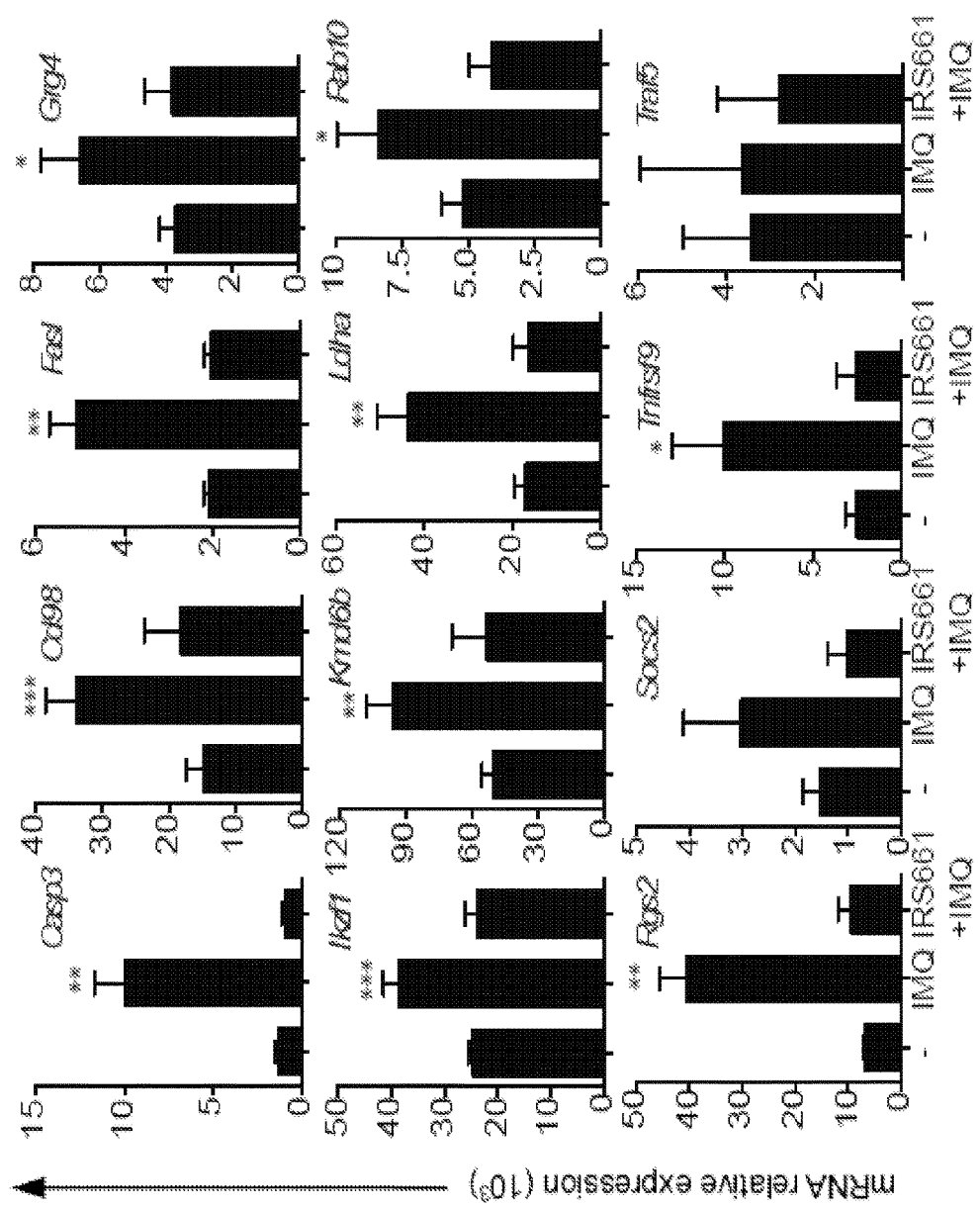
FIG. 26A shows mRNA expression of anergy-related genes expression in CD4$^+$ T cells stimulated with vehicle, IMQ or IRS661+IMQ for 2 hours.
Figure 26B:
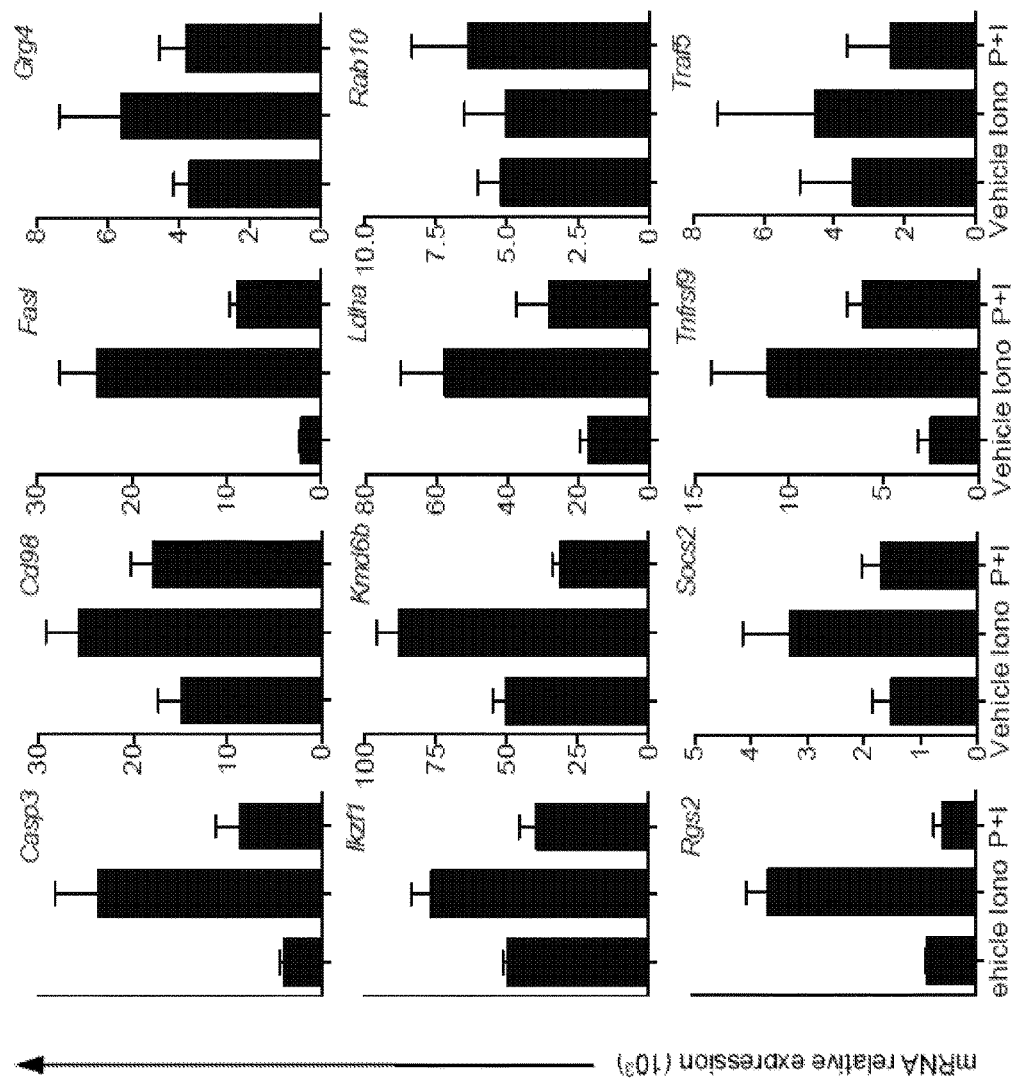
FIG. 26B shows mRNA expression of anergy-related genes expression in Ionomycin and PMA+Ionomycin-treated CD4$^+$ T cells. Gene expression was measured by TaqMan real-time PCR of anergy-related genes on CD4$^+$ T cells treated for 16 hours with Ionomycin (Iono), PMA and ionomycin (P+I) or vehicle. N=6.
Figure 27:
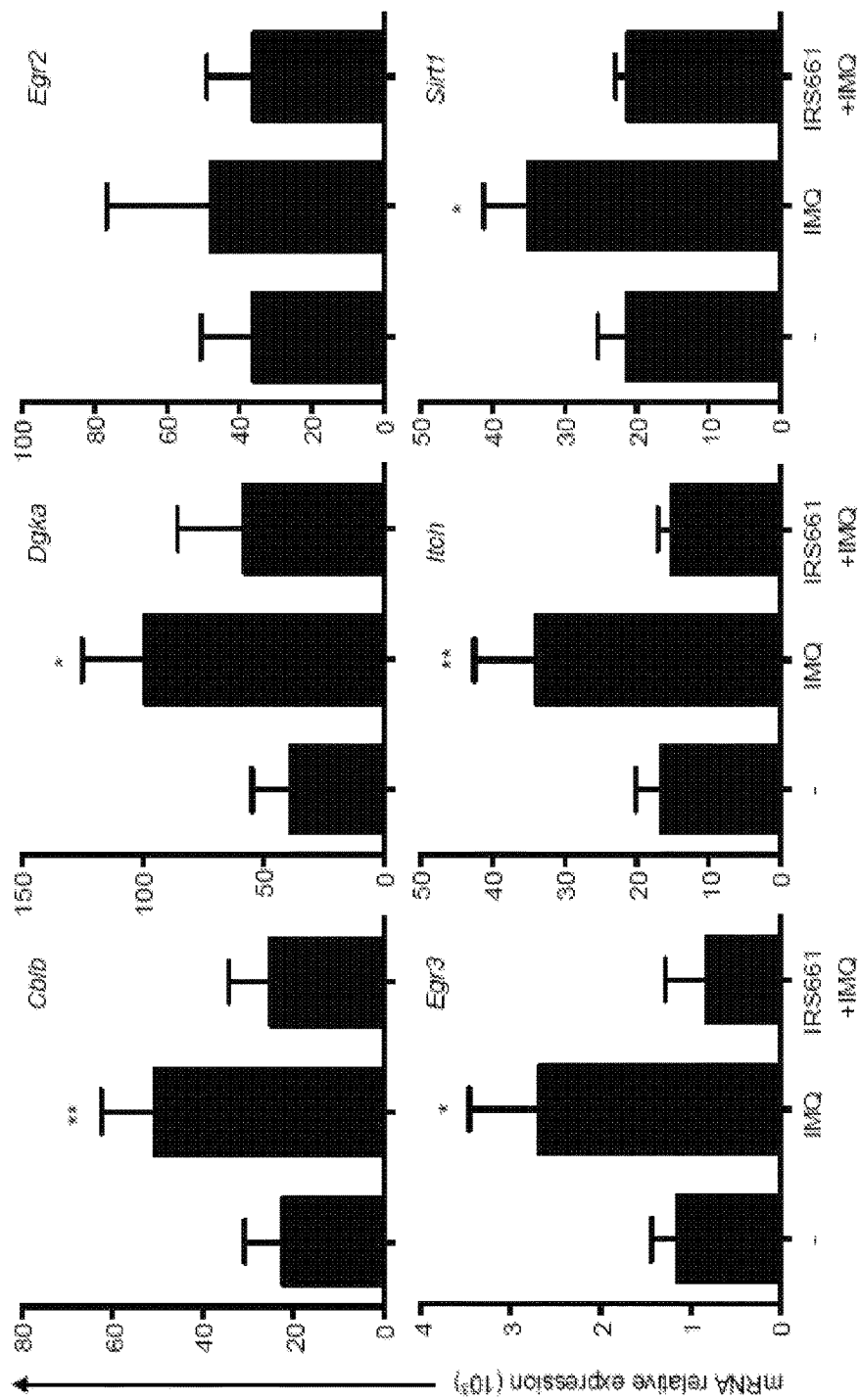
FIG. 27 is a panel of graphs showing the expression of Sirt1, Itch, Cblb, Dgka, Egr2 and Egr3 genes in Ionomycin and PMA+Ionomycin-treated CD4$^+$ T cells stimulated with vehicle, IMQ or IRS661+IMQ for 2 hours. *p<0.05, **p<0.005, with all of them but Egr2 showed a significant upregulation upon IMQ treatment.

To examine whether TLR7 stimulation and subsequent NFAT dephosphorylation induces the expression of anergy-related genes, CD4$^+$ T cells were incubated for 2-16 hours with IMQ in the presence or absence of the TLR7 inhibitory sequence IRS661 and RNA was isolated to examine the hypothesis that TLR7 engagement induced expression of anergy-related genes previously described. As a control for anergy-related gene expression, CD4$^+$ T cells were incubated with either ionomycin and PMA or ionomycin alone. Ten of the 12 anergy-related genes examined were significantly upregulated in IMQ-stimulated cells as compared to the control and PMA and ionomycin stimulation (FIGS. 26A and 26B). The effect observed in the regulation of these genes was TLR7-specific, as preincubation of CD4$^+$ T cells with IRS661 before IMQ treatment abrogated the increase in anergy-related gene expression. Furthermore, the expression of other genes that have been functionally related to the establishment and maintenance of the anergic phenotype and are NFAT targets, such as Sirt1, Itch, Cblb, Dgka, Egr2 and Egr3 was also examined, and all of them but Egr2 showed a significant upregulation upon IMQ treatment (FIG. 27).

Figure 28A:
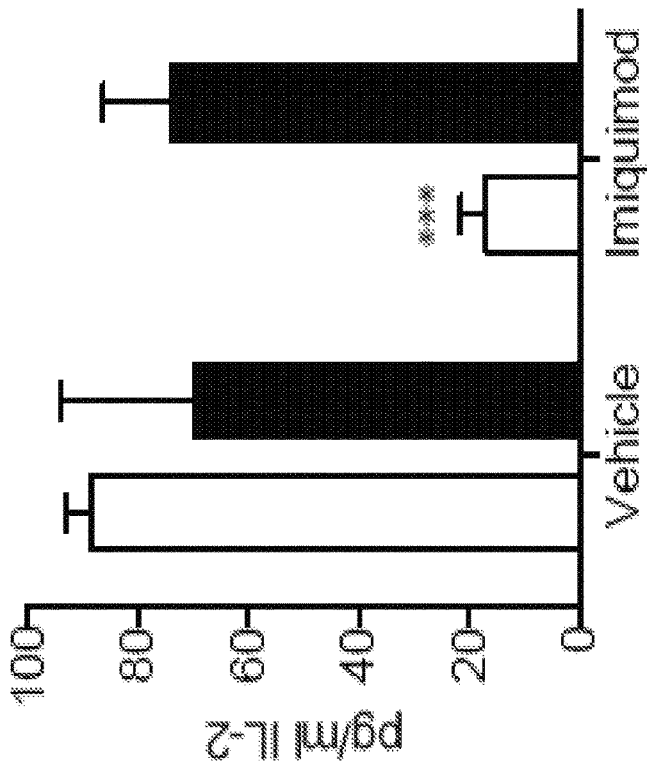
FIG. 28A shows IL-2 secretion measured by ELISA in non-target (white bars) and NFAT1 (black bars) shRNA-transduced CD4$^+$ T cells stimulated in the presence or absence of IMQ for 3 days.
Figure 28B:
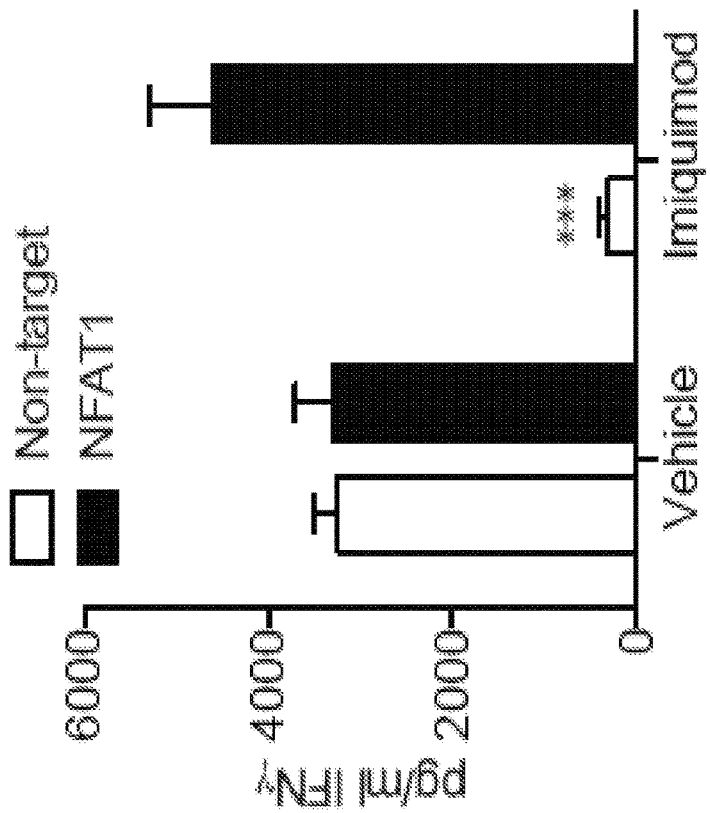
FIG. 28B shows IFNγ secretion measured by ELISA in non-target (white bars) and NFAT1 (black bars) shRNA-transduced CD4+ T cells stimulated in the presence or absence of IMQ for 3 days.
Figures 29, 30:
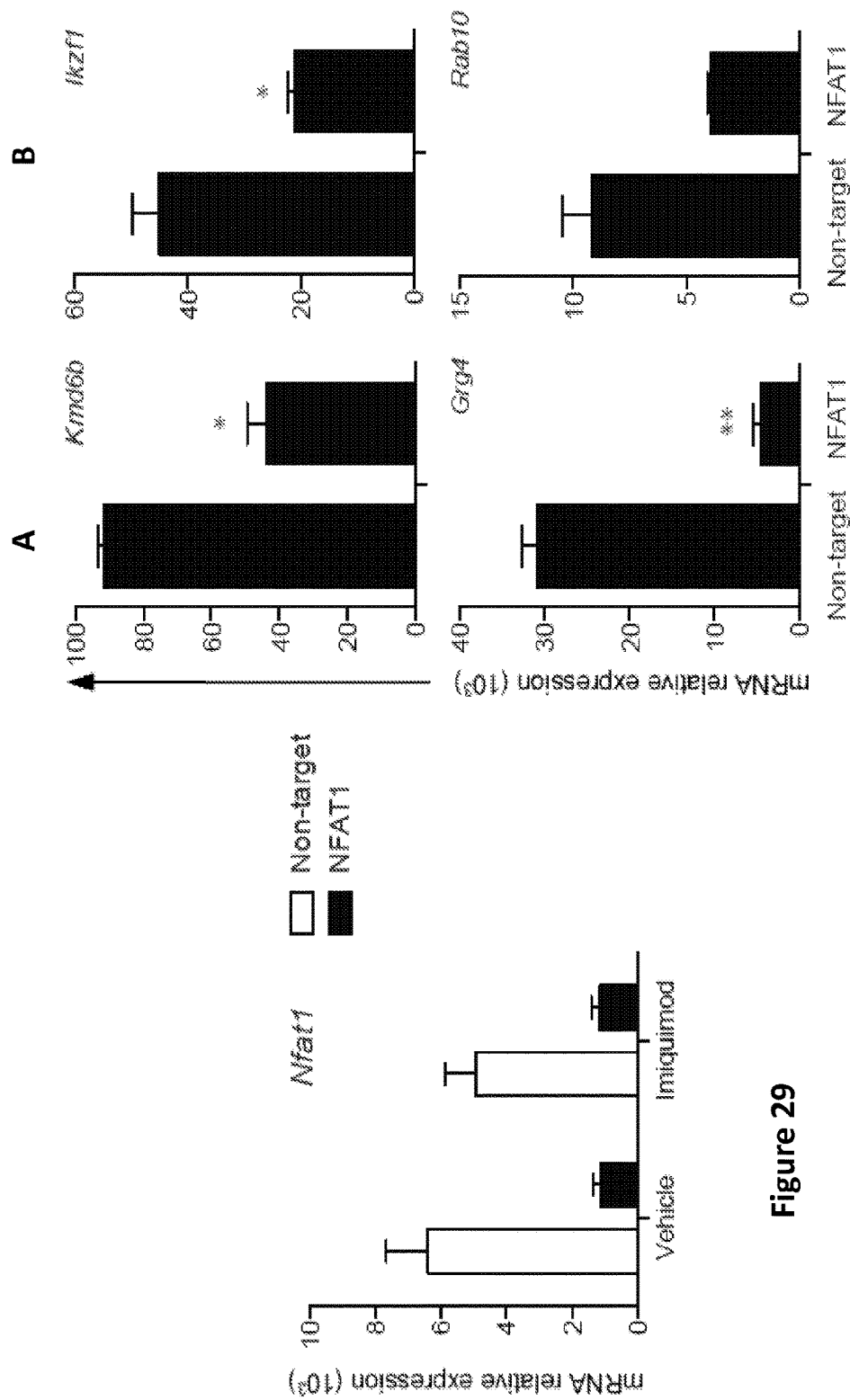
FIG. 29 shows NFAT1 gene expression by TaqMan real-time PCR 24 hours after stimulation. CD4+ T cells were transduced with shRNA specific for NFAT1 or a non-target control and stimulated with anti-CD3 and anti-CD28 in the presence or absence of IMQ. Bars diagram shows.

The data suggest that IMQ induces clonal anergy in CD4$^+$ T cells by the increase in intracellular calcium concentration and activation of NFAT-dependent anergic gene expression program. To further examine the role of NFAT1 on TLR7-induced T cell anergy, shRNA were used to silence NFAT1 (FIGS. 28A-28B and 29), and IMQ was used to induce anergy on resting CD4$^+$ T cells after NFAT1 knockdown. After 3 days in culture, cells transduced with a non-target shRNA and stimulated with IMQ significantly reduced the production of IL-2 (FIG. 28A) and IFNγ (FIG. 28B) while cells transduced with NFAT shRNA were not affected by IMQ treatment, suggesting that NFAT is necessary for the anergic phenotype driven by TLR7 signaling in CD4$^+$ T cells. IMQ treatment did not have an effect on NFAT1 gene expression (FIG. 29). In agreement with these data, IMQ treatment failed to upregulate the expression of anergy-related genes in NFAT1-deficient cells as compared to non-target transduced CD4+ T cells (FIGS. 30A-30D), confirming that this gene expression program driven by IMQ treatment on CD4+ T cells is largely NFAT1-dependent.

Figure 30F:
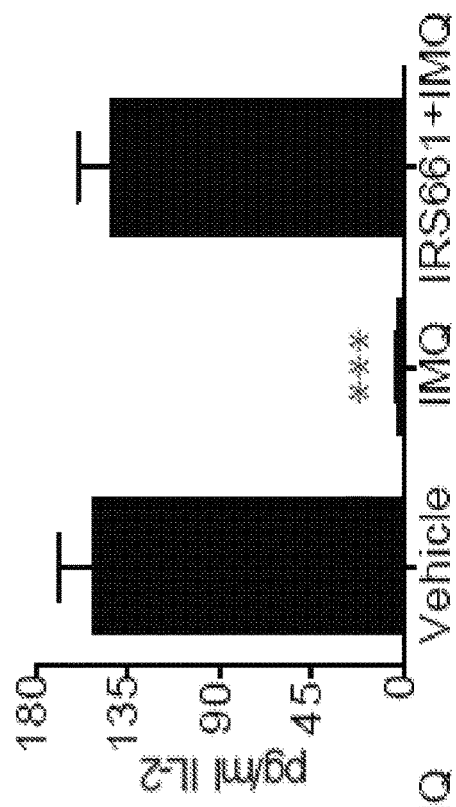
FIG. 30F shows IL-2 levels as measured by ELISA in CD4+ T cells that were incubated with vehicle and IMQ in the presence or absence or IRS661 for two hours, washed and stimulated with anti-CD3 and anti-CD28 for 2 days after a 12 hour resting period. Statistical analysis represents mean±s.e.m. of four independent experiments, *p<0.05, p<0.005, *p<0.0005*.
Figure 30E:
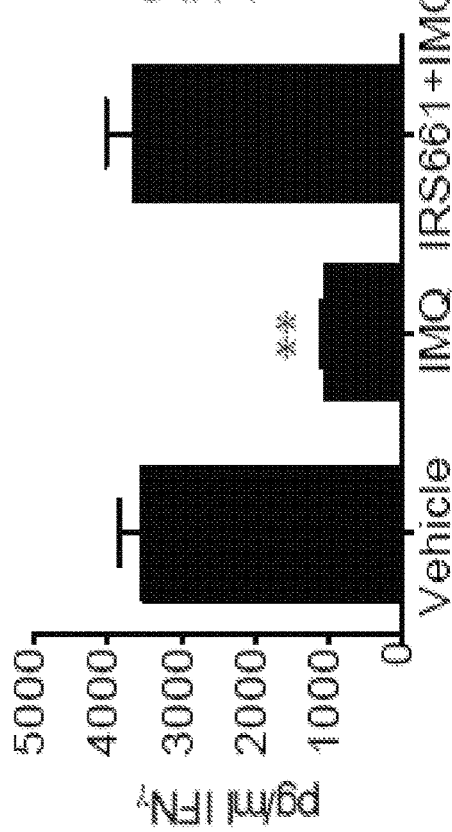
FIG. 30E shows IFNγ levels as measured by ELISA in CD4+ T cells that were incubated with vehicle and IMQ in the presence or absence or IRS661 for two hours, washed and stimulated with anti-CD3 and anti-CD28 for 2 days after a 12 hour resting period. Statistical analysis represents mean±s.e.m. of four independent experiments, *p<0.05, p<0.005, *p<0.0005*.

To determine if pretreatment of CD4+ T cells with IMQ would be sufficient to diminish their subsequent cytokine secretion and proliferative response to a full stimulation, memory T cells were pre-treated with IMQ for 2 hours and rested for 12 hours after washout to remove traces of IMQ and then stimulated with anti-CD3 and anti-CD28 for 3 days. IMQ-pretreated cells showed a significantly decreased production of both IL-2 (FIG. 30E) and IFNγ (FIG. 30F) that was not observed on IRS661 pretreated cells. No significant changes in cell viability were observed upon IMQ pretreatment.

Figure 31A:
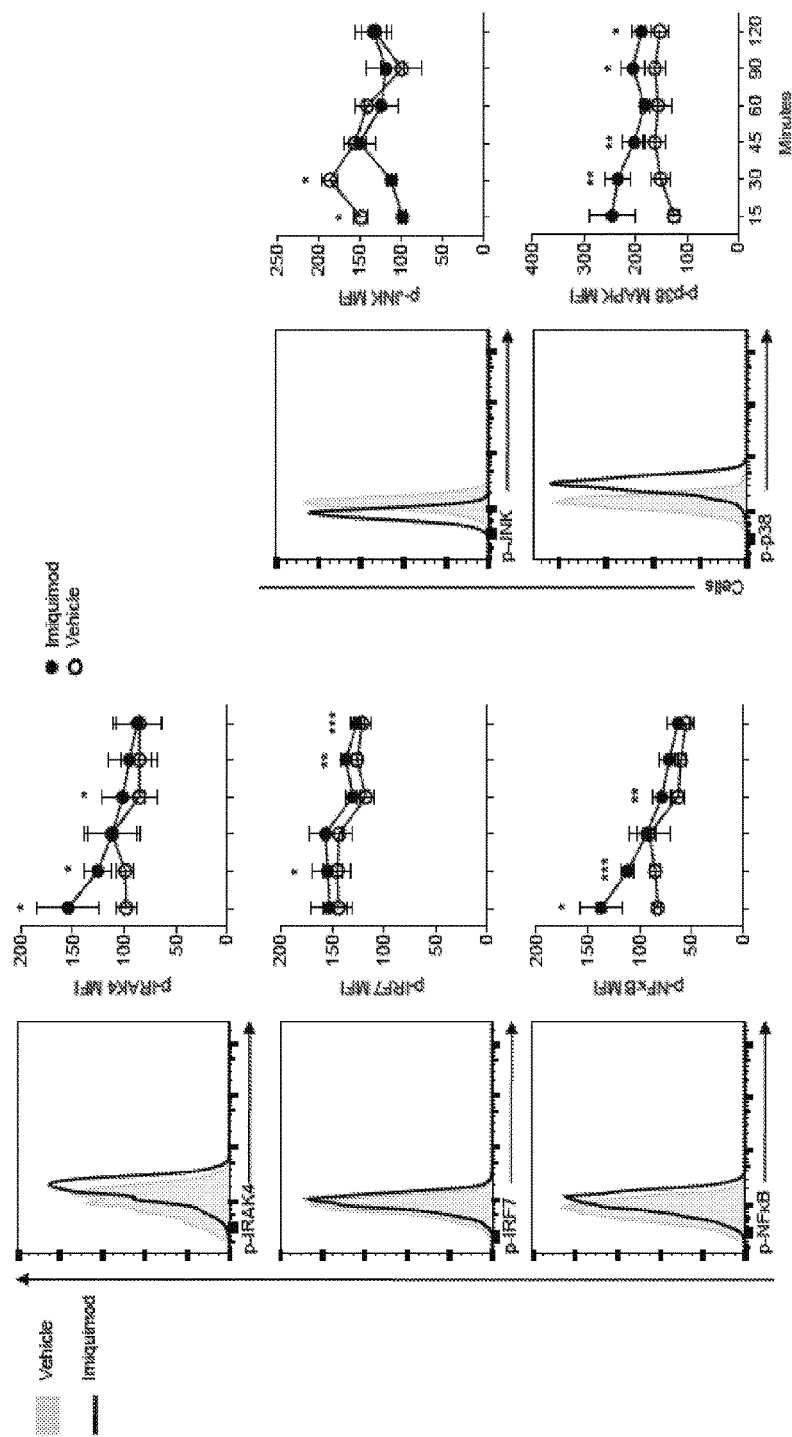
FIG. 31A is a panel of graphs showing phosphorylation status of IRAK4, JNK, NFkB (p65), p38 MAPK and IRF7 after vehicle or IMQ stimulation.

TLR7 signaling has predominantly been studied in APC where it is linked to IRF7, NFκB and JNK activation through either MyD88/IRAK4-dependent or -independent pathways. In order to examine the consequences of TLR7 signaling on CD4+ T cells in relation to 'conventional' TLR signaling, ex vivo isolated CD4+ T cells from healthy individuals were stimulated with IMQ and the phosphorylation status of IRAK4, JNK, NFkB (p65), p38 MAPK and IRF7 was examined by flow cytometry (FIG. 31A). TLR7 stimulation with IMQ induced the phosphorylation of IRAK4, IRF7, NFκB and p38 at different time points as compared to vehicle, but, interestingly, TLR7 engagement decreased the basal levels of phosphorylated JNK.

Figure 31B:
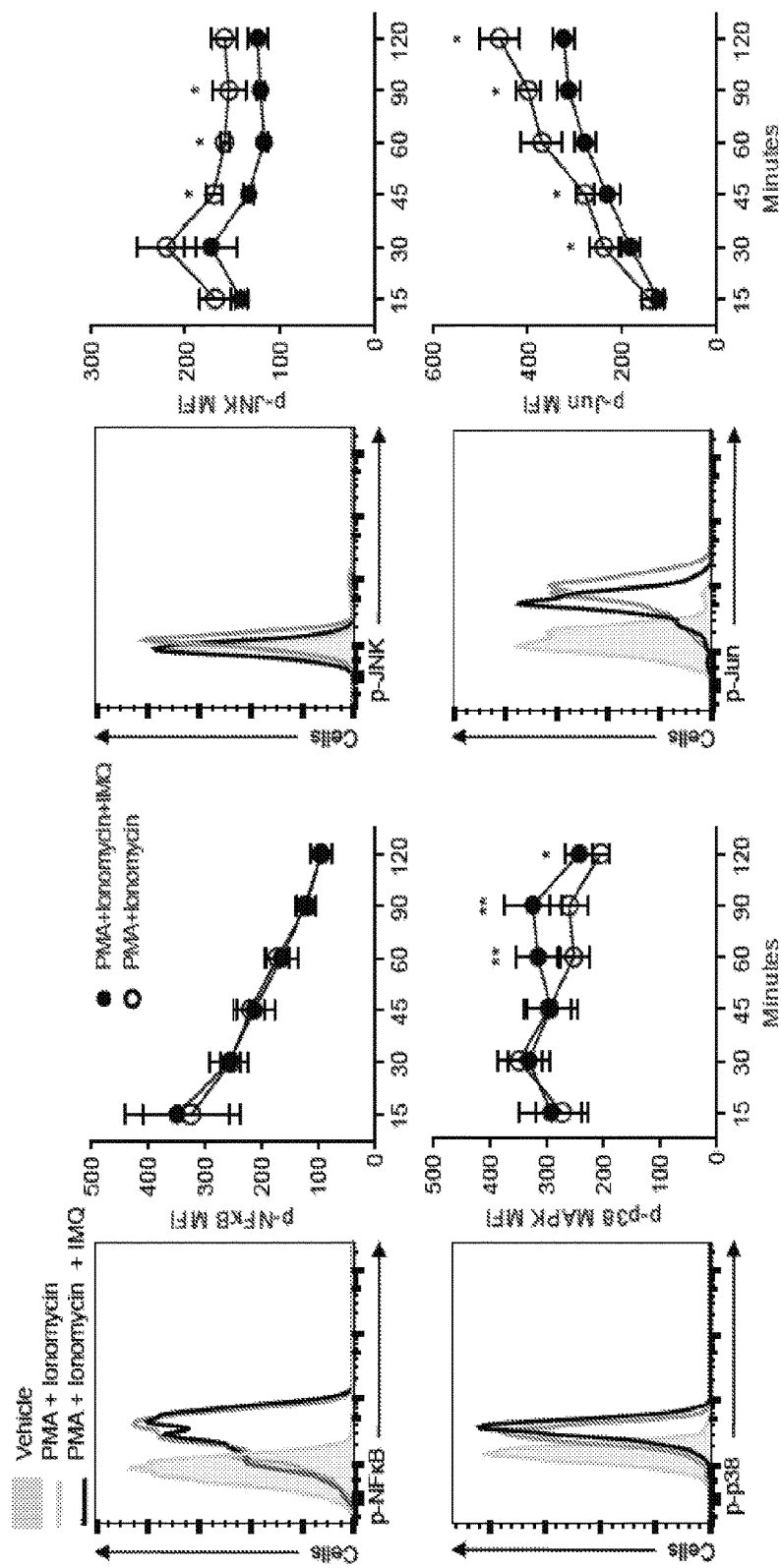
FIG. 31B is a panel of graphs showing the statistical analysis of 8 independent experiments performed to measure the expression of phosphorylated molecules at 60 minutes after activation in PMA+Ionomycin- or PMA+Ionomycin+IMQ-treated CD4+ T cells as compared to vehicle. *p <0.05, p<0.005, *p<0.0005.
Figure 31C:
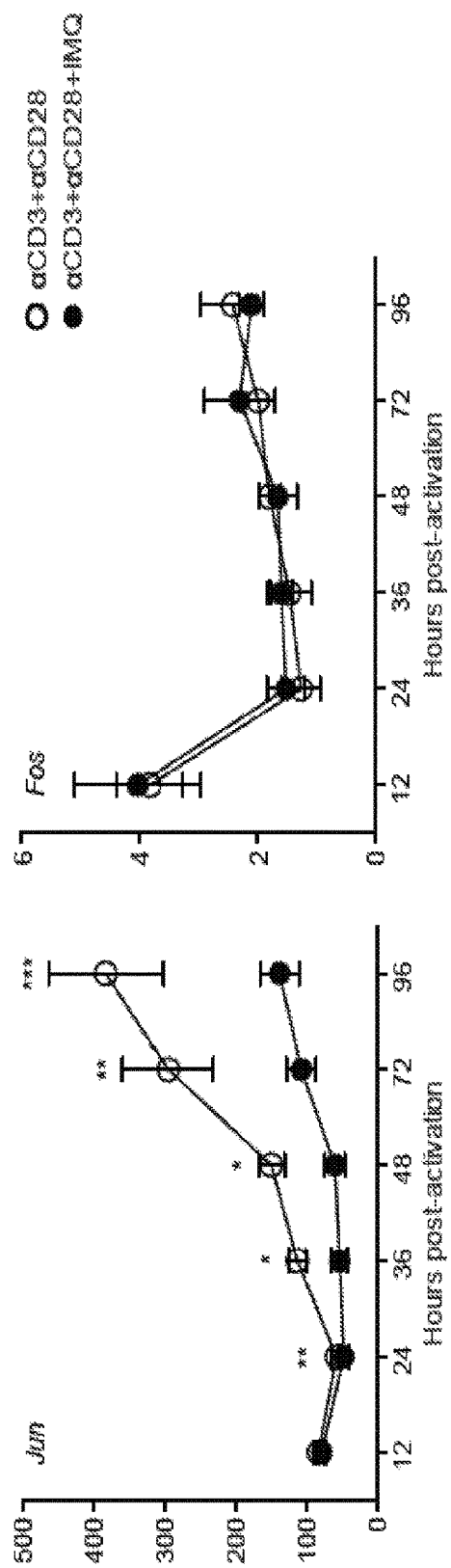
FIG. 31C is a panel of histograms showing the kinetics of Fos and Jun mRNA gene expression after stimulation of CD4+ T cells in the presence (black) or absence (white) of IMQ *p<0.05, p<0.005, *p<0.0005.

One of the targets that are phosphorylated by activated JNK is Jun, a component of AP-1, which is an essential transcription factor involved in costimulatory signal transduction. It was determined if inhibition of JNK activity by IMQ could explain, at least in part, the anergic phenotype observed in CD4+ T cells after IMQ stimulation in the presence of full stimulation with TCR and costimulatory signals. To test this hypothesis, CD4+ T cells were stimulated with PMA and Ionomycin in the presence or absence of IMQ, and the phosphorylation status of JNK and Jun was examined at different time points. NFκB and p38 were used as positive controls (FIGS. 31B and 31C). While IMQ treatment did not show an additive effect on NFκB phosphorylation with stimulation, IMQ further increased p38 phosphorylation levels. Of note, upon stimulation, JNK phosphorylation was inhibited by IMQ and this decrease in JNK activity was accompanied by a decrease in Jun phosphorylation.

Moreover, IMQ both decreased JNK and Jun activity measured by phosphorylation after activation, and decreased Jun gene expression (FIG. 31C). These data support the hypothesis that IMQ treatment both induces anergy on CD4+ T cells and interferes with costimulatory signals during T cell stimulation. The decrease in CD69 and CD137 expression (both AP-1 transcriptional targets) observed after stimulation in the presence of IMQ further supports this hypothesis.

CD4+ T cell responses from chronically HIV-1-infected patients are impaired and insufficient to clear the virus while displaying features of anergy. Several viral proteins have been shown to induce a state of T cell non-responsiveness that precedes CD4 T cell loss in HIV-1 patients. To determine if virus-CD4+ T cell interaction through TLR7 was responsible, at least in part, for the anergic phenotype observed in HIV-1-infected CD4+ T cells from patients, CD4+ T cells from four healthy individuals were isolated and examined their ability to produce IL-2 and IFNγ seven days after in vitro infection with physiological concentrations of the replication-competent DsRed-tagged HIV-1$_{NL-D}$, derived from the prototype HIV-1$_{NL432}$ virus (MOI 0.001).

Figure 32:
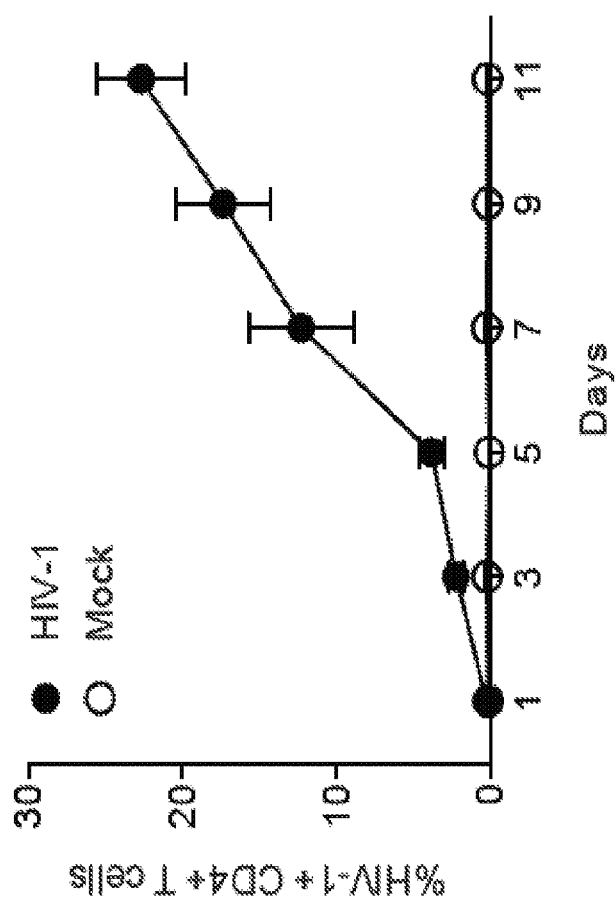
FIG. 32 shows the frequency of viable HIV-1$_{NL-D}$+CD4+ T cells measured every 48 hours for a total of 11 days (n=3) of CD4+ T cells stimulated with anti-CD3 and anti-CD28 for two days and subsequently infected with HIV-1$_{NL-D}$.
Figure 33:
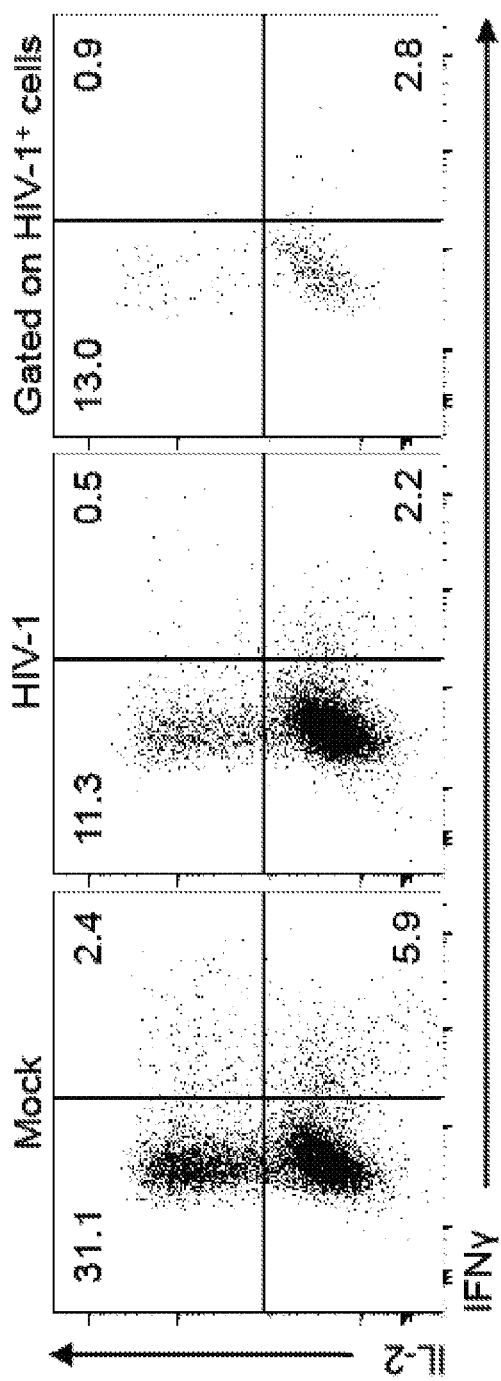
FIG. 33 shows a representative example of IL-2 and IFNγ secretion as measured by intracellular staining after a 4 hour PMA/Ionomycin stimulation at day 7 after infection on mock infected cells (left panel), total CD4+ T cells infected with HIV-1$_{NL-D}$ (middle panel) or HIV-1$_{NL-D}$+ cells. C. Statistical analysis of IL-2 and IFNγ (n=3). (*P< 0.05, **P<0.005).

In agreement with published reports, HIV-1 infection rendered CD4+ T cells unresponsive (FIG. 32). HIV-1 infection markedly decreased the ability of viable CD4+ T cells to produce IL-2 (FIG. 34B) and IFNγ (FIG. 34A) after stimulation (FIG. 33). This decrease in cytokine secretion was observed in HIV-1-infected DsRed-tagged cells, suggesting that the direct interaction of the virus with the infected CD4+ T cells rendered CD4+ T cells unresponsive.

Figure 35A:
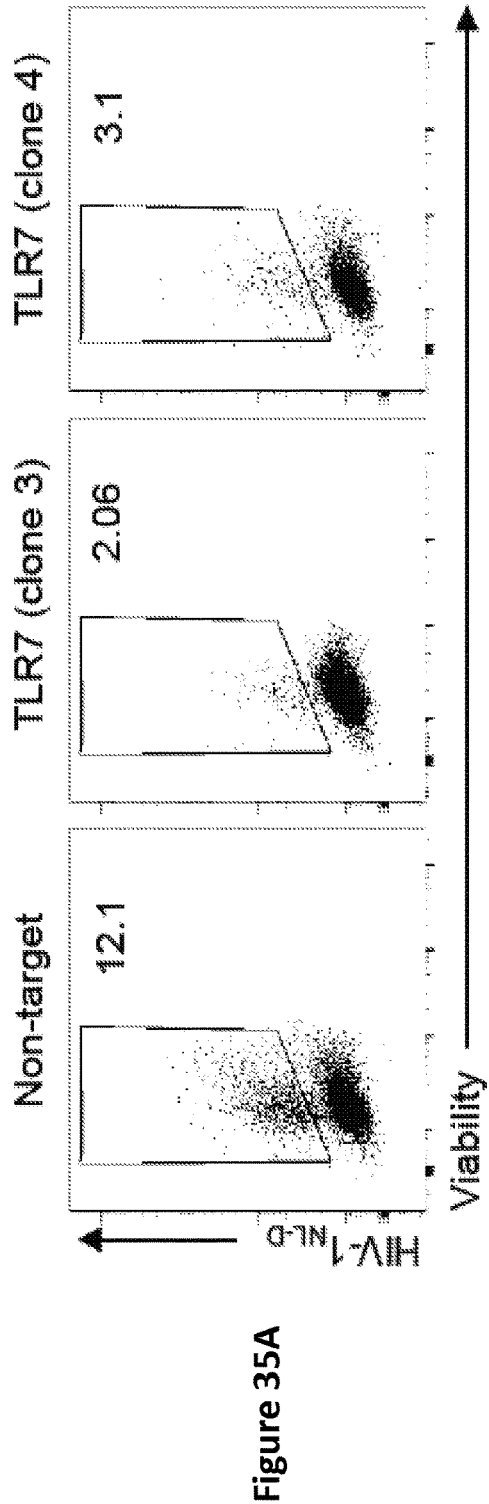
FIG. 35A is a panel of dot plots showing a representative example of the frequency of viable HIV-1$_{NL-D}$+CD4+ T cells on non-target (left dot plot) or TLR7 shRNA-transduced CD4+ T cells (middle and right dot plots) at day 7 after infection.
Figure 35B:
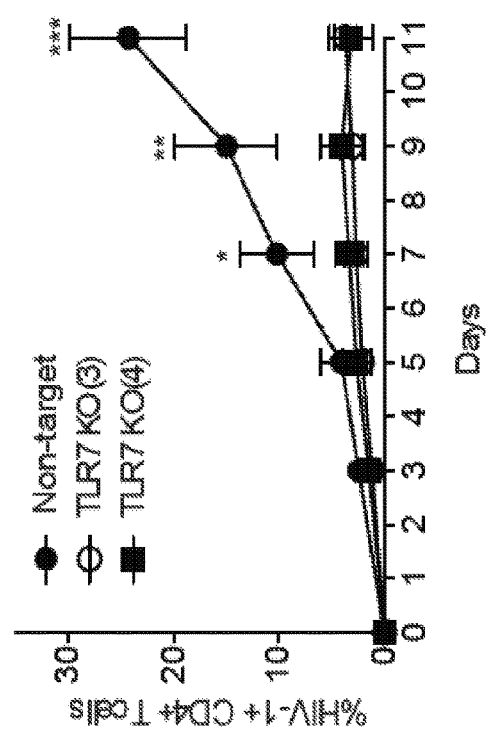
FIG. 35B shows the kinetics of HIV-1$_{NL-D}$ infection on non-target or TLR7 shRNA-transduced CD4+ T cells (n=4).

To test the hypothesis that TLR7 signaling in CD4+ T cells accounts, in part, for the anergic phenotype after HIV-1 infection, two shRNA specific for TLR7 (clones 3 and 4) or a non-target shRNA as control were used to silence TLR7 on ex vivo isolated CD4+ T cells from healthy donors. After two days, TLR7-deficient CD4+ T cells were infected with concentrations of HIV-1 within the physiological range (MOI 0.001) and the frequency of infected cells as well as their ability to produce proinflammatory cytokines was measured every 48 hours for a total of 11 days. Surprisingly, while non-target transduced CD4+ T cells were infected with HIV-1 at a similar extent to non-transduced cells, TLR7-deficient cells showed a marked decrease in the frequency of HIV-1-infected CD4+ T cells at all time points examined (FIG. 35A-35B).

Figure 36A:
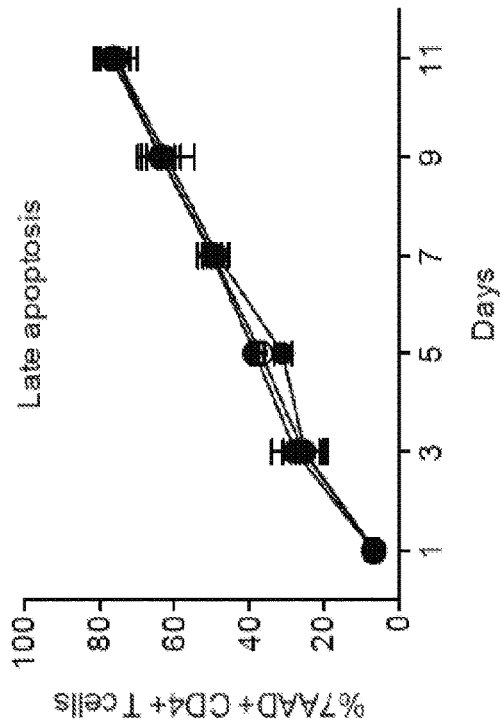
FIG. 36A shows early apoptosis after HIV-1 infection in TLR7 and non-target-transduced CD4+ T cells stained with Annexin V and 7-AAD every 24 hours for 11 days after stimulation with anti-CD3 and anti-CD28 in the presence of two TLR7 shRNA (clones 3 and 4) or non-target control shRNA.
Figure 36B:
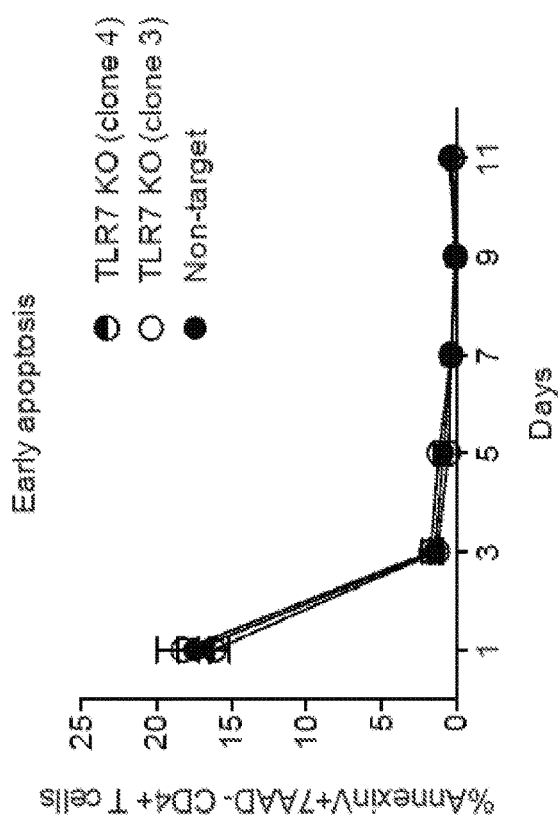
FIG. 36B shows late apoptosis after HIV-1 infection in TLR7 and non-target-transduced CD4+ T cells stained with Annexin V and 7-AAD every 24 hours for 11 days after stimulation with anti-CD3 and anti-CD28 in the presence of two TLR7 shRNA (clones 3 and 4) or non-target control shRNA.

This decrease in the frequency of HIV-1+ cells was not due to a specific increase in cell death on TLR7-silenced cells, as there were no differences in the frequency of early (FIG. 36A) and late (FIG. 36B) apoptotic CD4+ T cells after infection as compared to the control (non-target-transduced CD4+ T cells). The critical role of TLR7 in HIV-1 infectivity was further confirmed by TLR7 blockade on CD4+ T cells from healthy donors with different doses of IRS661 prior in vitro infection (FIG. 37A-37B).

Figure 38A:
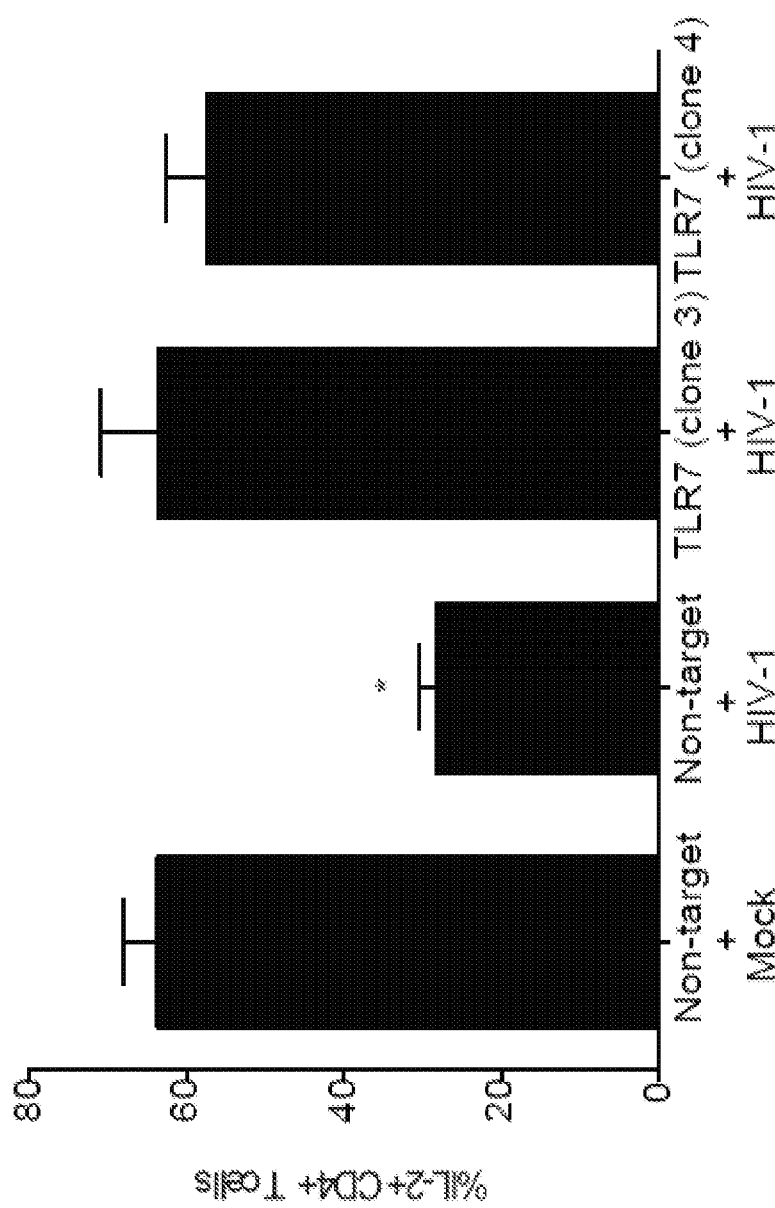
FIG. 38A shows statistical analysis of IL-2 secretion as measured by intracellular staining after a 4-hour PMA/Ionomycin stimulation at day 7 after infection of non-target-transduced cells (mock and HIV-1-infected) and two TLR7 shRNA (clones 3 and 4) transduced with HIV-1$_{NL-D}$ (n=3). (*P<0.05).
Figure 38B:
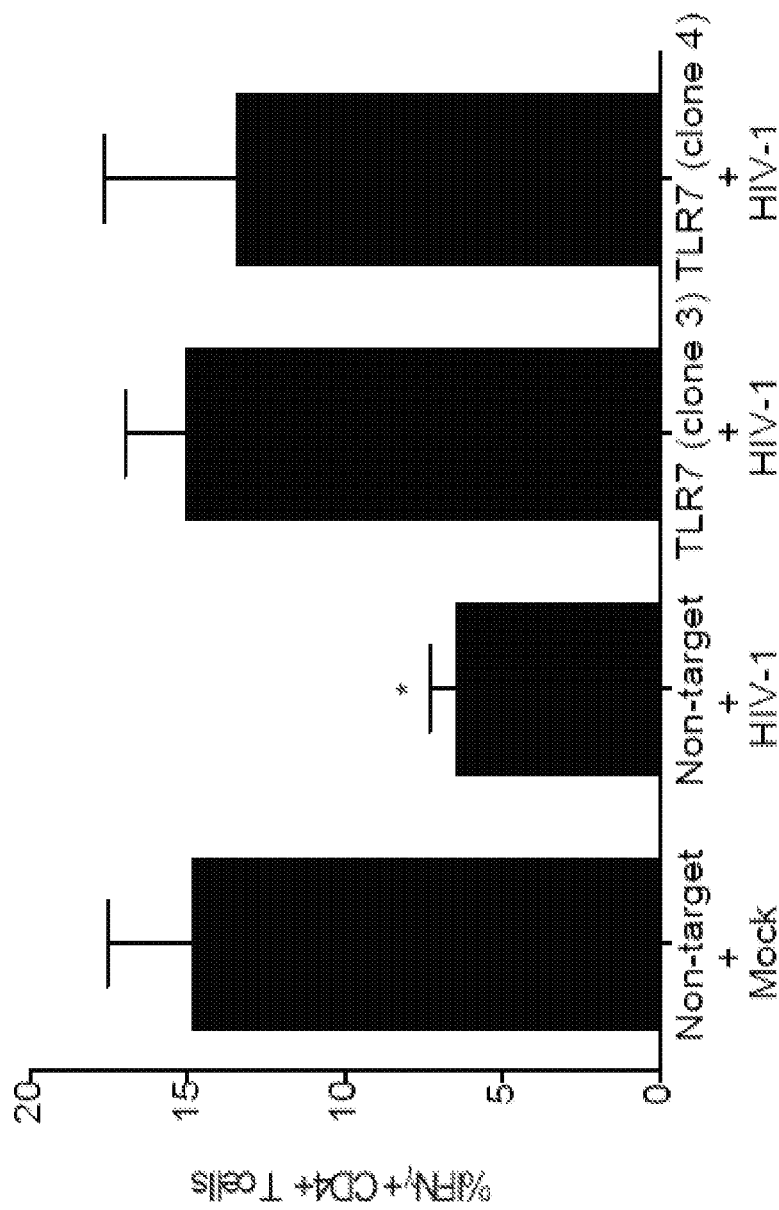
FIG. 38B shows statistical analysis of IFNγ secretion as measured by intracellular staining after a 4-hour PMA/Ionomycin stimulation at day 7 after infection of non-target-transduced cells (mock and HIV-1-infected) and two TLR7 shRNA (clones 3 and 4) transduced with HIV-1$_{NL-D}$ (n=3). (*P<0.05).
Figure 39:
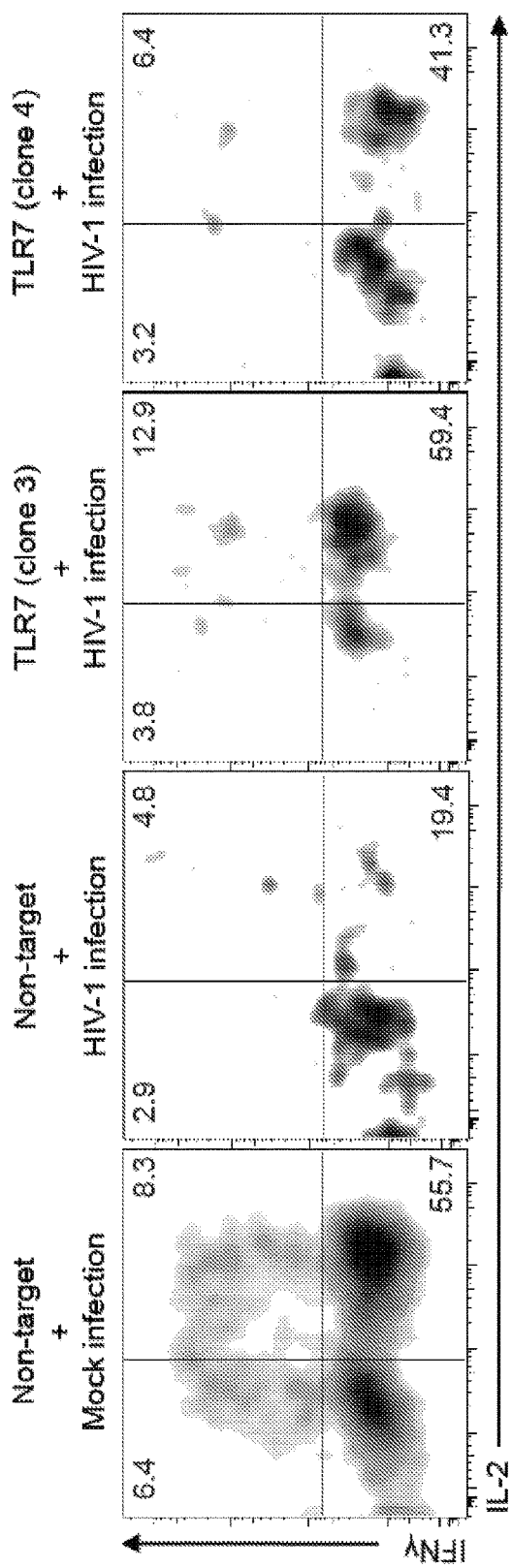
FIG. 39 is a panel of dot plots showing a representative example at day 7 of IFNγ and IL-2 secretion of CD4+ T cells stimulated with anti-CD3 and anti-CD28 in the presence of two TLR7 shRNA or non-target control and two days after infection with HIV-1$_{NL-D}$ or mock infection (left plot).

Moreover, cytokine secretion of HIV-1-infected cells was significantly different in non-target transduced cells as compared to TLR7-deficient cells. While HIV-1-infected cells in non-target-transduced CD4+ T cell culture displayed decreased levels of IL-2 (FIG. 38A) and IFNγ, (FIG. 38B) the small frequency of CD4+ T cells infected with HIV-1 in TLR7-deficient cells secreted significantly more IL-2 and IFNγ than non-target-transduced cells, suggesting that the anergic phenotype is not observed in TLR7-deficient cells after infection (FIGS. 38A and 38B). HIV-1 infection does not induce anergy on TLR7-deficient cells.

Figure 40:
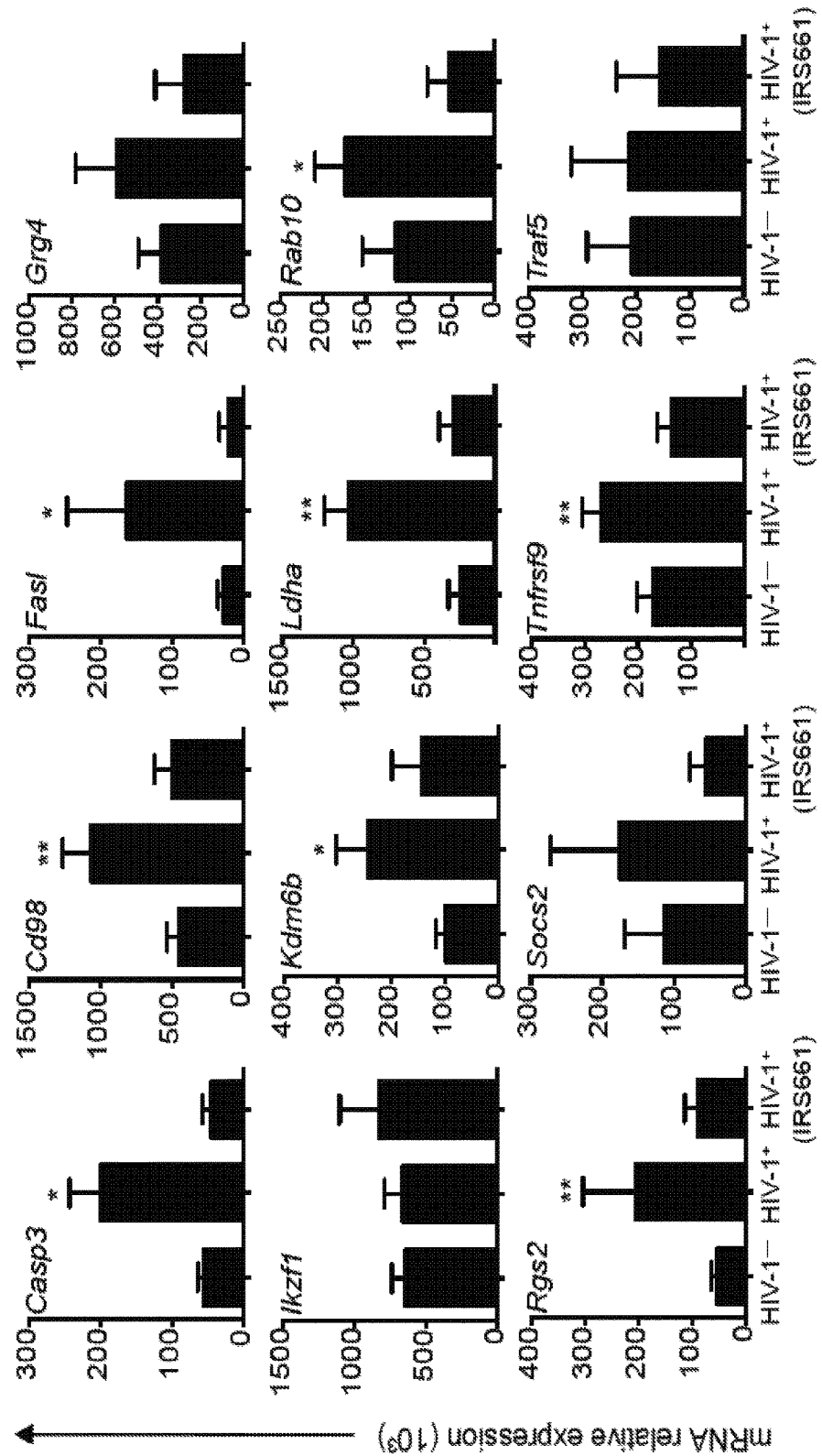
FIG. 40 is a panel of graphs showing the expression of anergy-related genes in in vitro HIV-1-infected CD4+ T cells in the presence of IRS661 or a control sequence at day seven after infection. *p<0.05, p<0.005, *p<0.0005.
Figure 41:
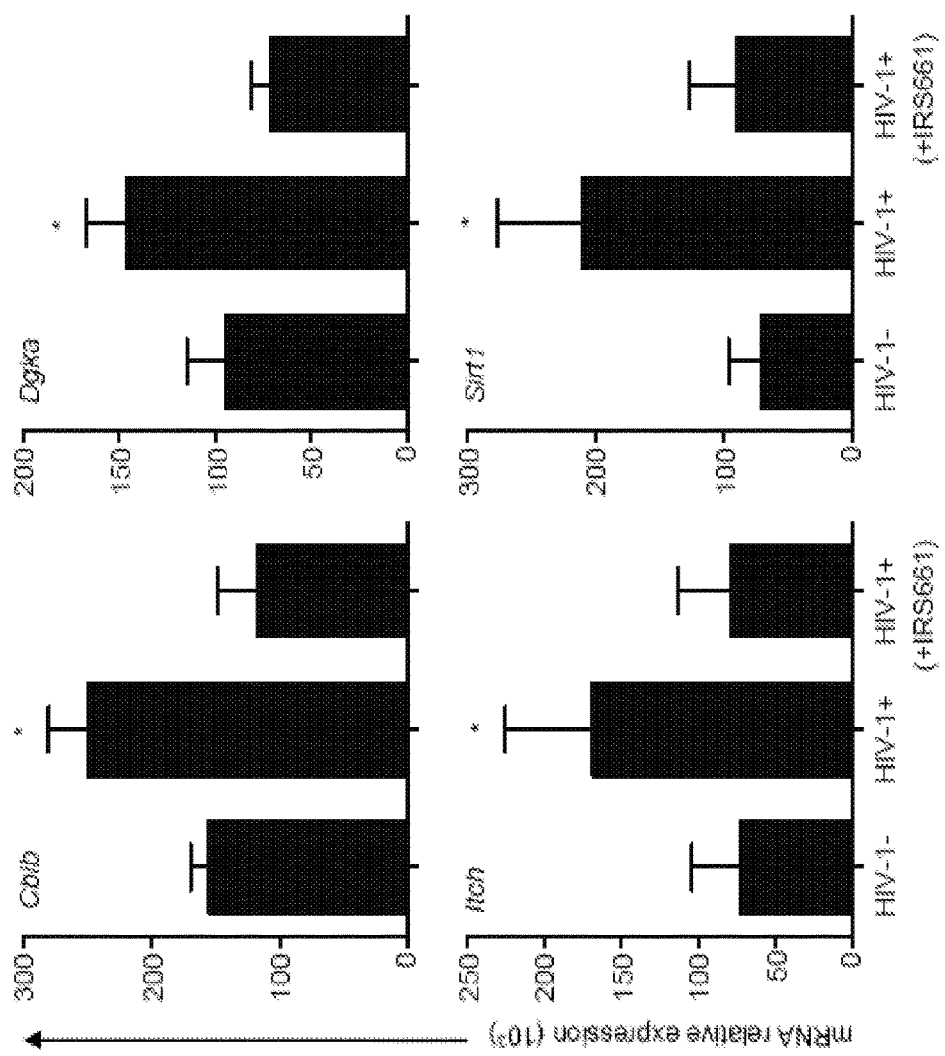
FIG. 41 is a panel of graphs showing expression of other genes also upregulated in HIV-1+CD4+ T cells, but not in IRS661-treated HIV-1+ T cells. *p<0.05.

To confirm this observation, the expression of anergy-related genes in in vitro HIV-1-infected CD4+ T cells from five healthy donors in the presence of IRS661 (to inhibit TLR7) or a control sequence at day seven after infection was examined (FIG. 40). Sorted HW-1+CD4+ T cells showed an increased expression of 8 out of the 12 anergy-related genes examined, while HW-1+CD4+ T cells sorted from IRS661-treated cultures did not upregulate any of these genes at the time point analyzed. The expression of other genes that have been functionally implicated in anergy were also upregulated in HIV-1+CD4+ T cells, but not in IRS661-treated HIV-1+ T cells (FIG. 41). These data suggest that HIV-1 interaction with TLR7 is responsible for the anergic phenotype observed in infected HW-1+CD4+ T cells.

Figure 42B:
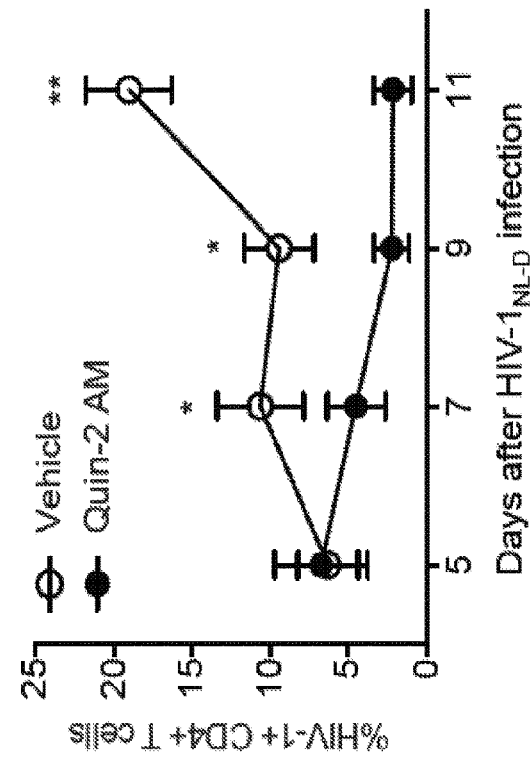
FIG. 42B is a graph showing the statistical analysis of 6 independent experiments performed measuring the percentage of HIV+CD4+ T cells present after HIV-1 infection of cells incubated with vehicle or the chelation agent Quin-2 AM[57]. *p<0.05, p<0.005, *p<0.0005.
Figure 42A:
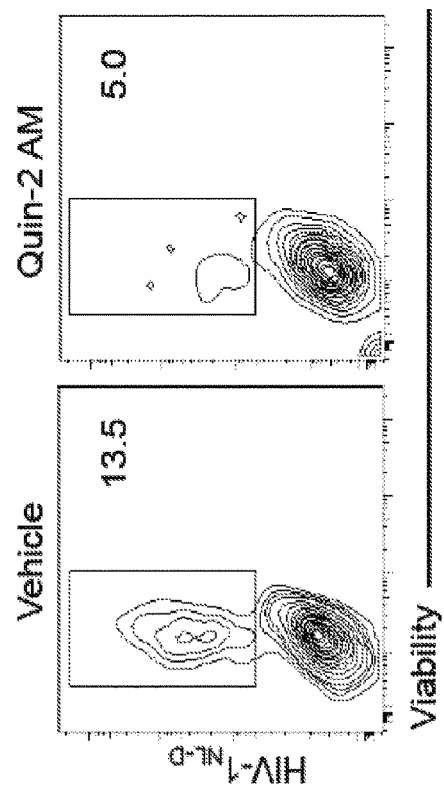
FIG. 42A is a panel of plots showing CD4+ T cells pre-incubated with vehicle (left plot) or the chelation agent Quin-2 AM[57] (right plot) before HIV-1 infection to induce a calcium blockade.
Figure 43A:
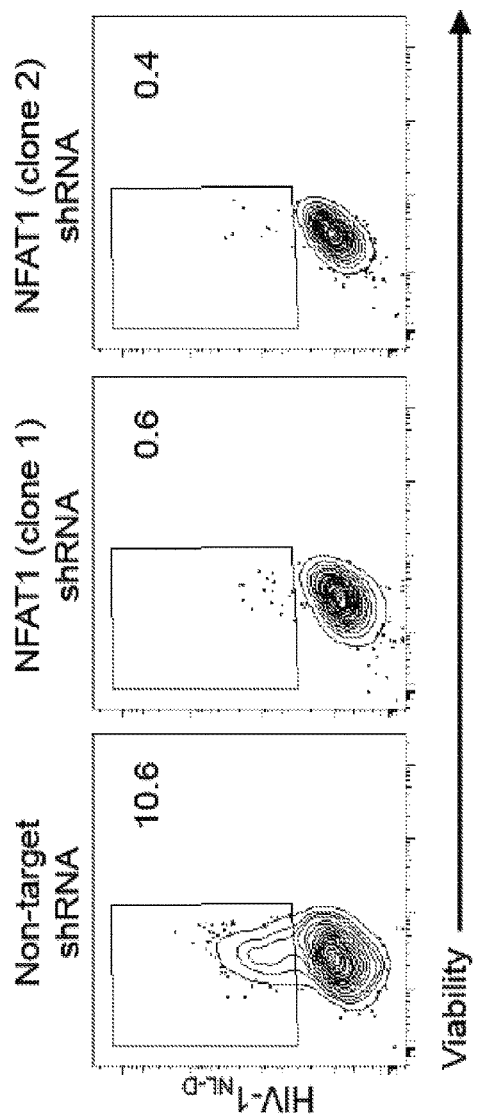
FIG. 43A is a panel of plots showing the frequency of viable CD4+ T cells pre-incubated with non-target shRNA (left plot) or two different NFAT1 shRNAs before HIV-1 infection two days later.
Figure 43B:
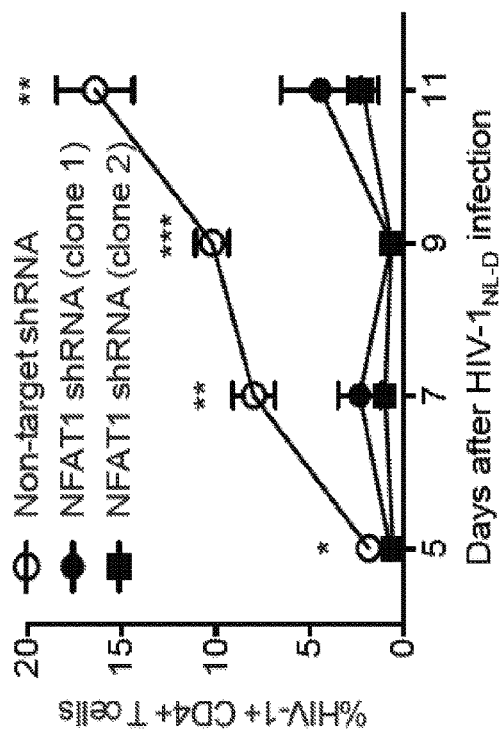
FIG. 43B is a graph showing the statistical analysis of 6 independent experiments performed to measure the percentage of viable HIV+CD4+ T cells present after HIV-1 infection of cells incubated with non-target shRNA or two different NFAT1 shRNAs. *p<0.05, p<0.005, *p<0.0005.
Figure 44A:
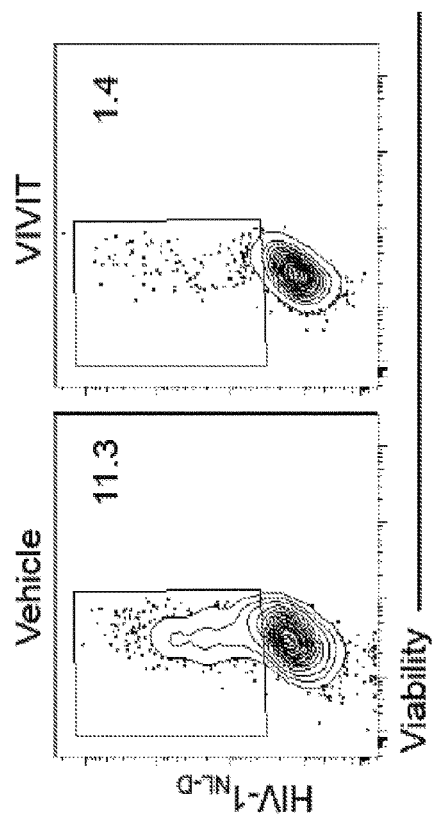
FIG. 44A is a panel of plots showing CD4+ T cells pre-incubated with vehicle or VIVIT peptide, which interferes with calcineurin-NFAT interaction before HIV-1 infection, to inhibit NFAT dephosphorylation.
Figure 44B:
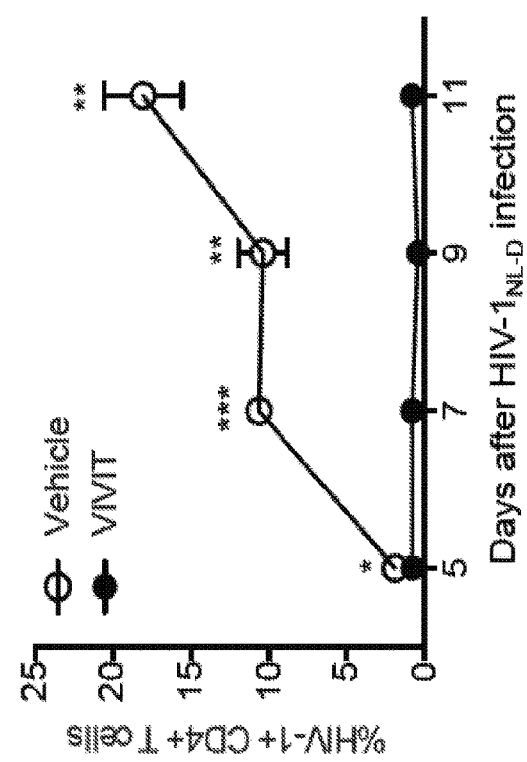
FIG. 44B is a graph showing the statistical analysis of 6 independent experiments performed to measure the percentage of HIV+CD4+ T cells present after HIV-1 infection of cells incubated with vehicle or VIVIT peptide. *p<0.05, p<0.005, *p<0.0005.

The role of intracellular calcium and NFAT-1-activated gene expression signaling events observed by TLR7 engagement with IMQ, after in vitro HIV-1 infection was examined. To determine if intracellular calcium blockade and NFAT-1 silencing would lead to a decrease in the frequency of HIV-1+ T cells even in the presence of a functional TLR7, CD4+ T cells were pre-incubated with the chelation agent Quin-2 AM or vehicle before HIV-1 infection to induce a calcium blockade (FIGS. 42A and 42B). Calcium chelation significantly decreased the frequency of viable cells even at the lowest chelating agent concentration, perhaps due to the essential role of calcium in many cellular processes. Nevertheless, the remaining viable CD4 cells in culture showed a marked decrease in the frequency of HIV-1$^+$ T cells, in agreement with previous investigations indicating a role for calcium in HIV-1 life cycle. NFAT1 was then silenced with either two different shRNA (FIGS. 43A and 43B) or blocked with VIVIT peptide, which interferes with calcineurin-NFAT interaction (FIGS. 44A and 44B), inhibiting NFAT dephosphorylation. In both cases, the absence of functional NFAT1 led to a significant decrease in the frequency of HIV-1-infected T cells, suggesting a role for NFAT-1 in HIV-1 infection.

Figure 45A:
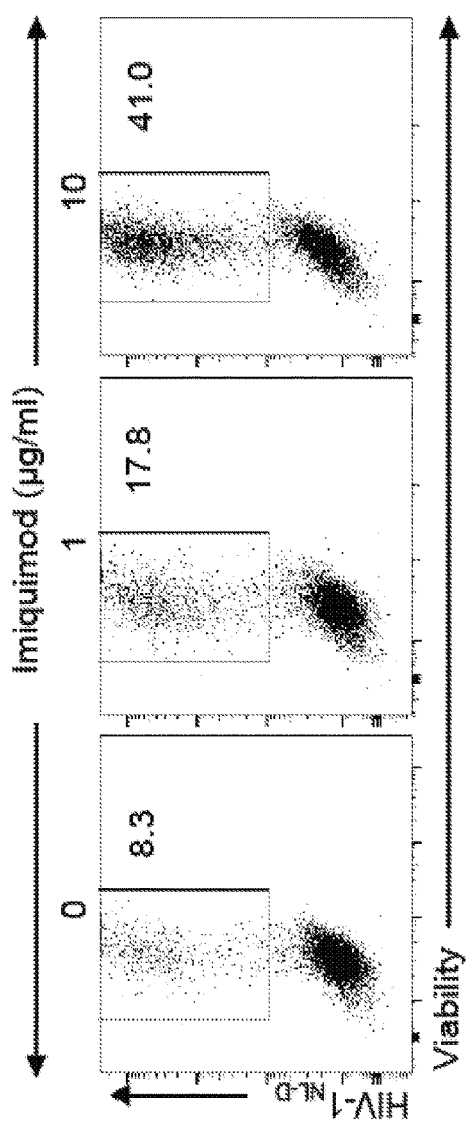
FIG. 45A is a panel of dot plots showing a representative example of frequency of viable HIV-1$_{NL-D}$+CD4+ T cells at day 7 after infection.
Figure 45B:
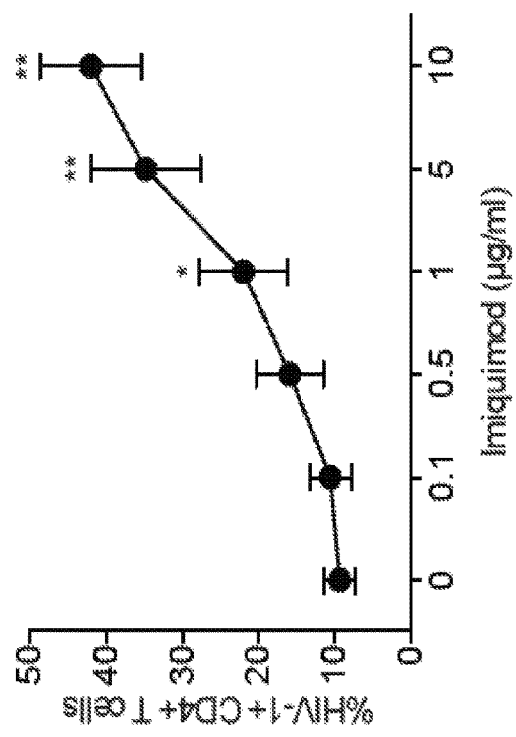
FIG. 45B is a statistical analysis of the frequency of HIV-1$_{NL-D}$+CD4+ T cells incubated with different doses of Imiquimod (n=3). *p<0.05, p<0.005, *p<0.0005.
Figure 46A:
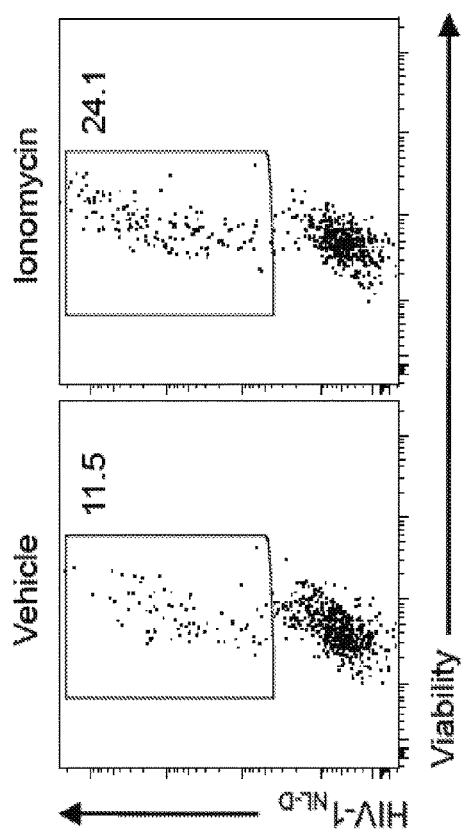
FIG. 46A is a panel of plots showing viability of HIV+ cells pre-incubated with vehicle or ionomycin, which induces anergy.
Figure 46B:
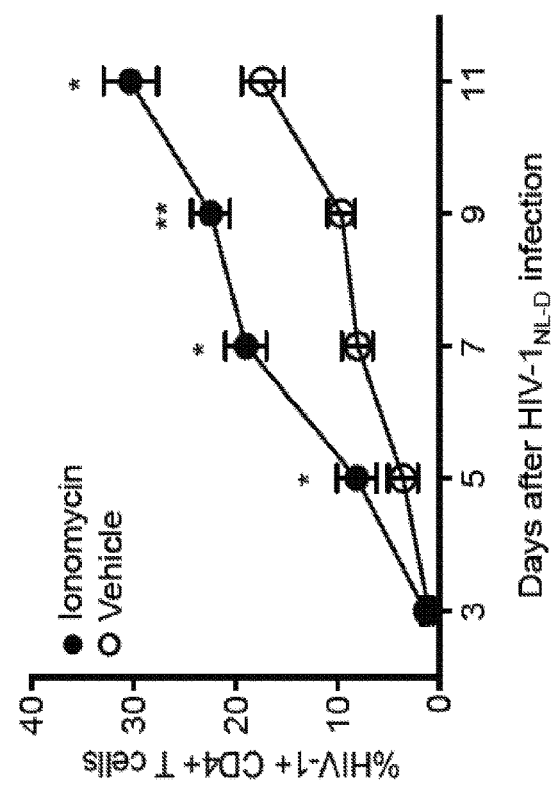
FIG. 46B is a graph showing the statistical analysis of 6 independent experiments performed to measure the percentage of HIV+CD4+ T cells present after HIV-1 infection of cells incubated with vehicle or ionomycin. *p0.05, **p<0.005.
Figure 47A:
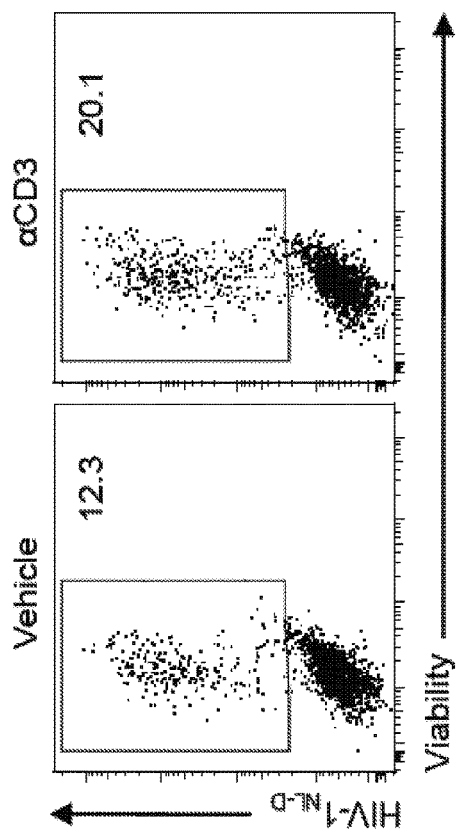
FIG. 47A is a panel of plots showing viability of HIV+ cells pre-incubated with vehicle or anti-CD3 stimulation without costimulatory signals, which induces anergy at day 9 after infection.
Figure 47B:
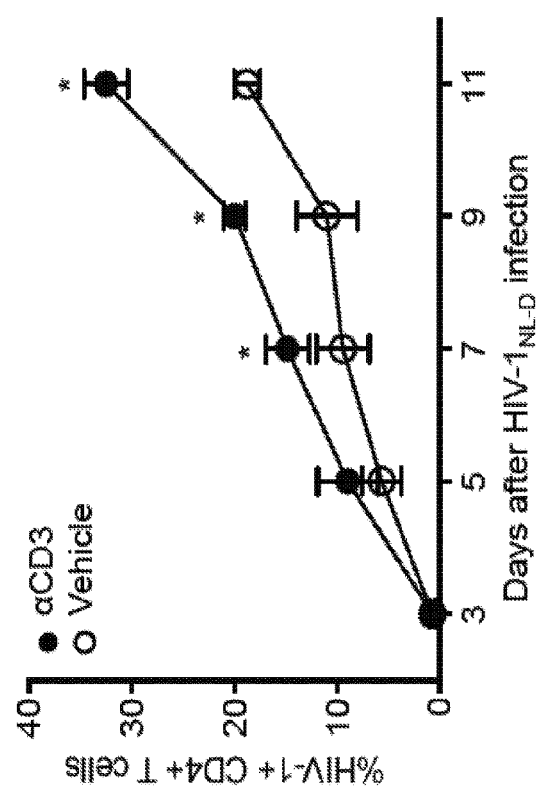
FIG. 47B is a graph showing the statistical analysis of 6 independent experiments performed to measure the percentage of HIV+CD4+ T cells present after HIV-1 infection of cells incubated with vehicle or anti-CD3 stimulation without costimulatory signals. *p<0.05, **p<0.005.

Based on the decrease infection rate on TLR7-silenced cells and the non-anergic phenotype of the infected CD4$^+$ TLR7-deficient T cells, it was hypothesized that the anergic state induced by TLR7 stimulation during HIV-1 infection would be a necessary step for HIV-1 to persist in the host. In the absence of TLR7, the virus would not be able to render the cells anergic and long-term infection would not occur. To examine this hypothesis, a state of anergy was induced in CD4$^+$ T cells from healthy donors with different doses of IMQ and subsequently infected them with HIV-1 for 7 days (FIGS. 45A-45B). Of note, the frequency of HIV-1 infected CD4$^+$ T cells directly correlated with the concentration of IMQ used, suggesting that anergy favours HIV-1 infection. Moreover, anergy induction through other well established in vitro methods, such as ionomycin treatment (FIGS. 46A and 46B) or anti-CD3 stimulation without costimulatory signals (FIGS. 47A and 47B) prior to HIV-1 infection increased the frequency of HIV-1$^+$ infected cells. These data support the hypothesis of HIV-1-induced anergy by TLR7 ligation being a prerequisite for productive HIV-1 infection.

Figures 48, 49:
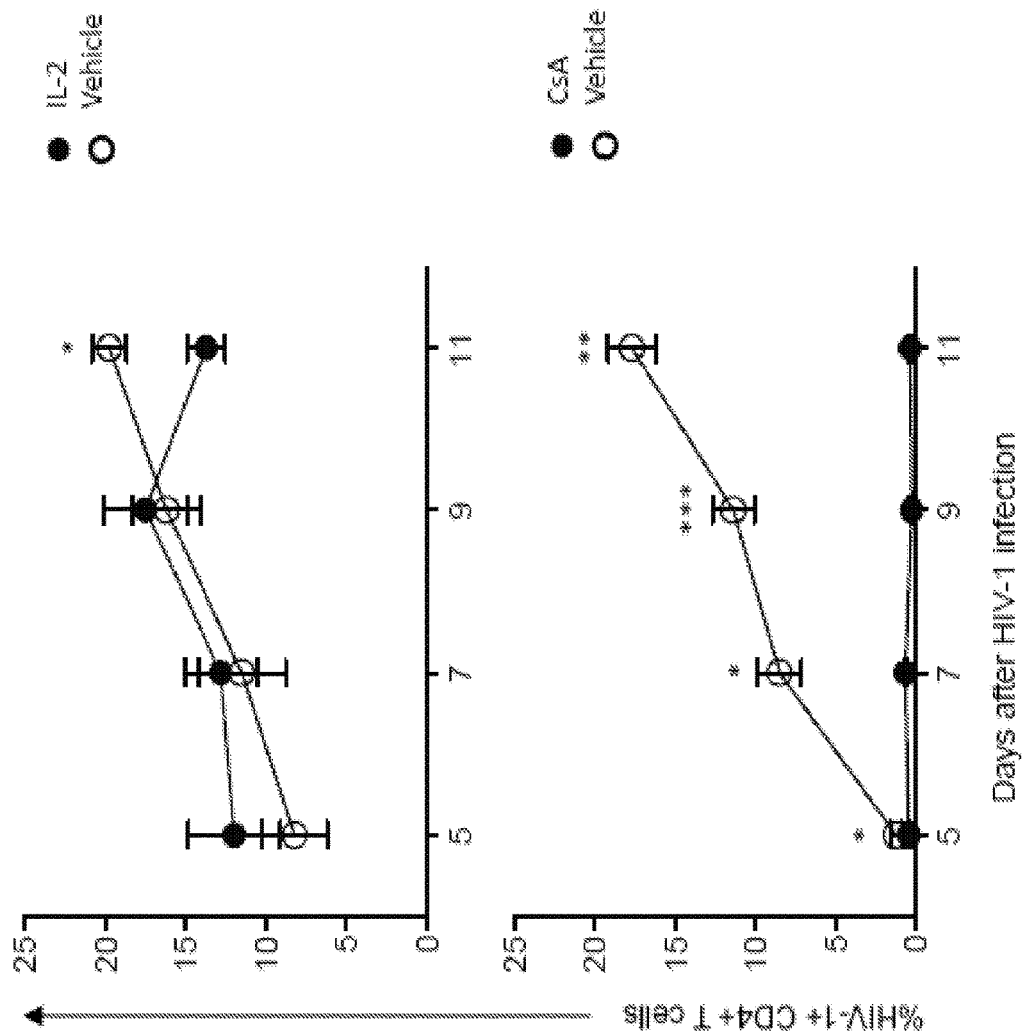
FIG. 48 is a panel of graphs showing the percentage of HIV+CD4+ T cells were stimulated with anti-CD3 and anti-CD28 for two days and pre-incubated with IL-2 six hours before HIV-1 infection. *p<0.05, p<0.005, *p<0.0005.
FIG. 49 is a graph showing the percentage of HIV+CD4+ T cells were stimulated with anti-CD3 and anti-CD28 for two days and pre-incubated with vehicle or cyclosporine A before HIV-1 infection. *p<0.05, p<0.005, *p<0.0005.

To further examine whether inhibiting TLR7-induced anergy would affect the frequency of HIV-1-infected cells, either Cyclosporine A or concentrations of IL-2 that have been shown to reverse anergy in several in vitro settings were added prior to in vitro HIV-1 infection. Although the addition of IL-2 six hours before HIV-1 infection did not affect the frequency of HIV-1-infected cells, perhaps due to response kinetics or the broad spectrum of IL-2 functions, (FIG. 48), blocking anergy with cyclosporine A significantly decreased the frequency of HIV-1$^+$ T cells (FIG. 49), further supporting the hypothesis that HIV-1-induced anergy is necessary for productive HIV-1 infection.

Figure 50:
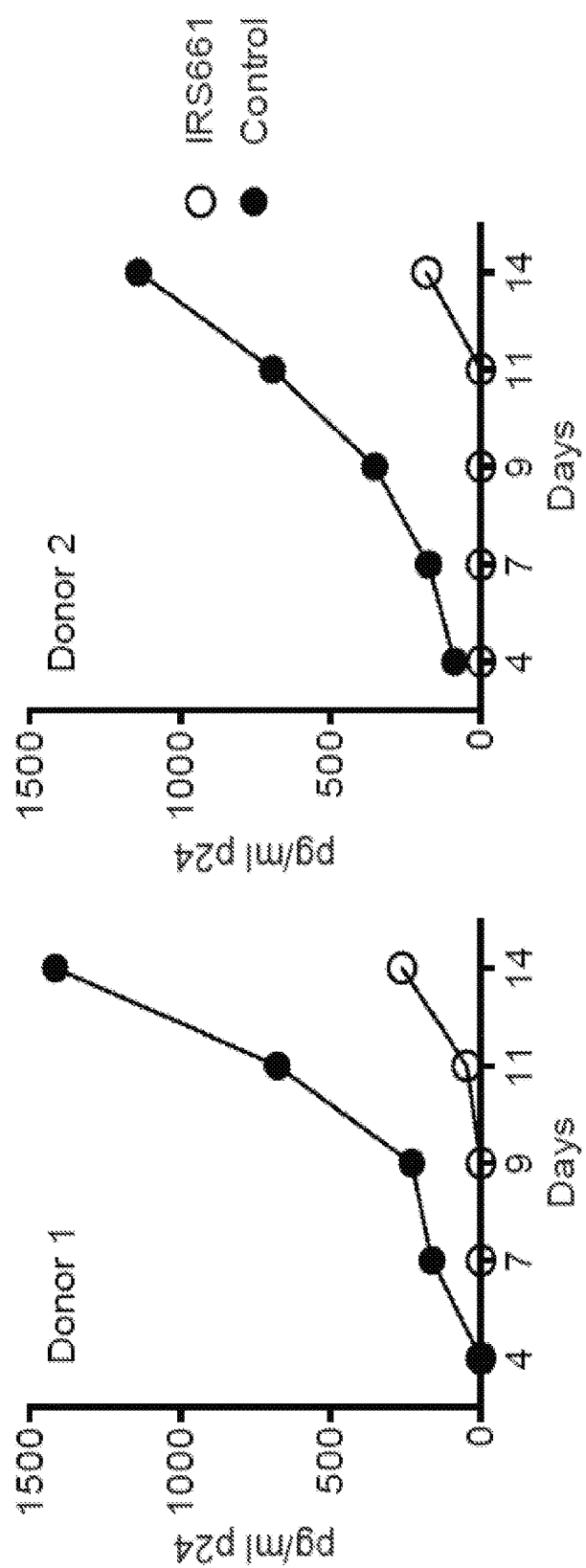
FIG. 50 is a panel of graphs showing the virus concentration (p24) measured in CD4+ T cells isolated from HIV-1 infected patients (Donor 1, left and Donor 2, right) after stimulation for 14 days in the presence of IRS661.
Figure 51:
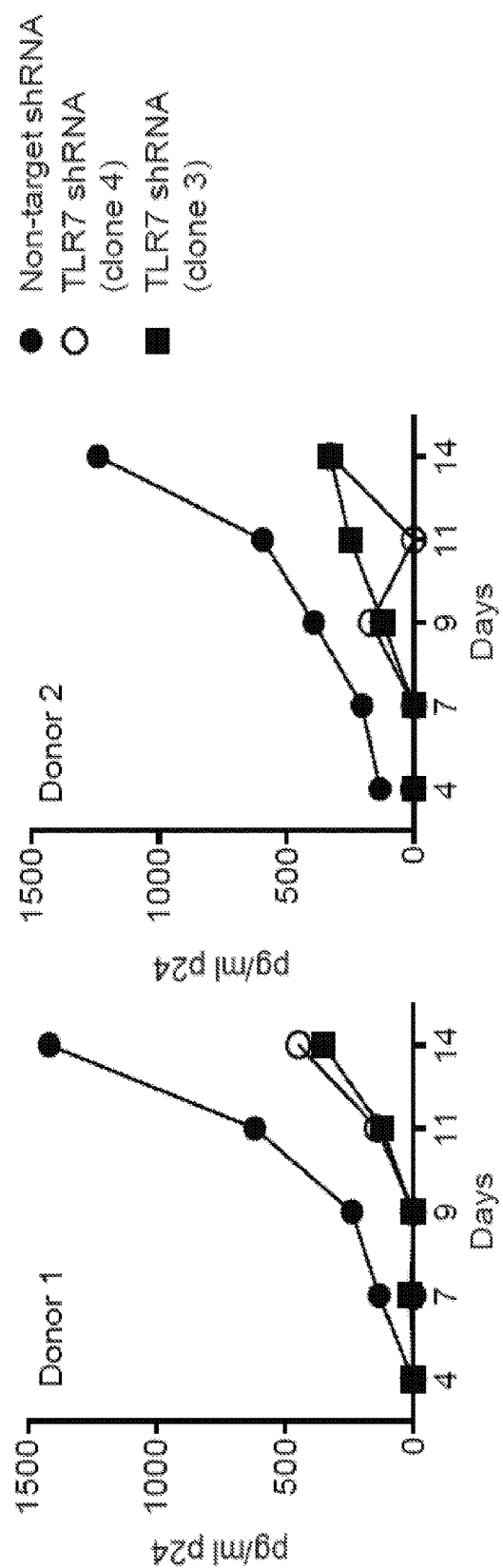
FIG. 51 is a panel of graphs showing the virus concentration (p24) measured in CD4+ T cells isolated from HIV-1 infected patients (Donor 1, left and Donor 2, right) after transduction for 14 days with two TLR7-specific shRNA.

The role of TLR7 in CD4$^+$ T cells from HIV-1-infected patients was directly examined. Specifically, based on the in vitro model system with DsRed-tagged HIV-1$_{NL-D}$, inhibition of the TLR7 pathway in CD4$^+$ T cells from HIV-1-infected patients could decrease the infection rate. CD4$^+$ T cells isolated from HIV-1 infected patients (Table 3) were stimulated in the presence of IRS661 (FIG. 50) or were transduced with two TLR7-specific shRNA (FIG. 51) with supernatant collections every three days for a total of 14 days to measure virus concentration by p24 ELISA. TLR7 inhibition by IRS661 strongly decreased the concentration of p24 in culture and similar results were obtained when the cells were transduced with two TLR7-specific shRNA (FIG. 51). Healthy donor CD4$^+$ T cells were assayed in parallel as a negative control, with no detectable p24 levels at any time point.

TABLE 3

| TaqMan probes | |
|---|---|
| Probe | Catalog number |
| Cblb | Hs00180288_m1 |
| Dgka | Hs00176278_m1 |
| Egr2 | Hs00166165_m1 |
| Egr3 | Hs00231780_m1 |
| Nfat1 | Hs00234855_m1 |
| Sirt1 | Hs01009003_m1 |
| Itch | Hs00395201_m1 |
| Il17a | Hs00936345_m1 |
| Il4 | Hs00929862_m1 |
| Ifng | Hs00989291_m1 |
| Il10 | Hs00961622_m1 |
| Foxp3 | Hs01085834_m1 |
| Tbx21 | Hs00203436_m1 |
| Rorc2 | Hs01076112_m1 |
| Gata3 | Hs00231122_m1 |
| Il2 | Hs00914135_m1 |
| Tlr7 | Hs00152971_m1 |
| Tlr8 | Hs00152972_m1 |
| Casp3 | Hs00991554_m1 |
| Cd98 | Hs00374243_m1 |
| Fasl | Hs00181225_m1 |
| Grg4 | Hs00419101_m1 |
| Ikzf1 | Hs00958474_m1 |
| Kmd6b | Hs00996325_g1 |
| Ldha | Hs00855332_g1 |
| Rab10 | Hs00211643_m1 |
| Rgs2 | Hs01009070_g1 |
| Socs2 | Hs00919620_m1 |
| Tnfrsf9 | Hs00155512_m1 |
| Traf5 | Hs00182979_m1 |
| β2m | 4326319E |

Figure 52:
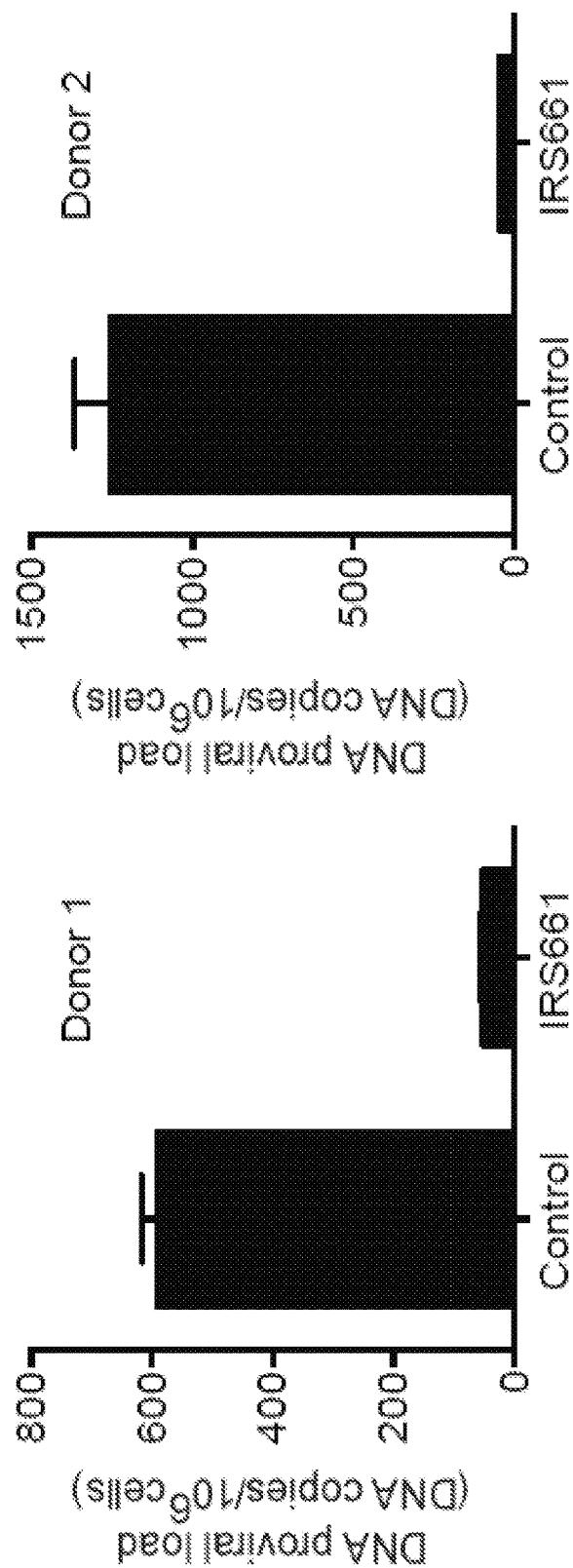
FIG. 52 is a panel of graphs showing proviral integrated DNA load measured at day seven after stimulation for 7 days in the presence of IRS661 or a control sequence in CD4+ T cells from HIV-1 infected patients (Donor 1, left and Donor 2, right).
Figure 53:
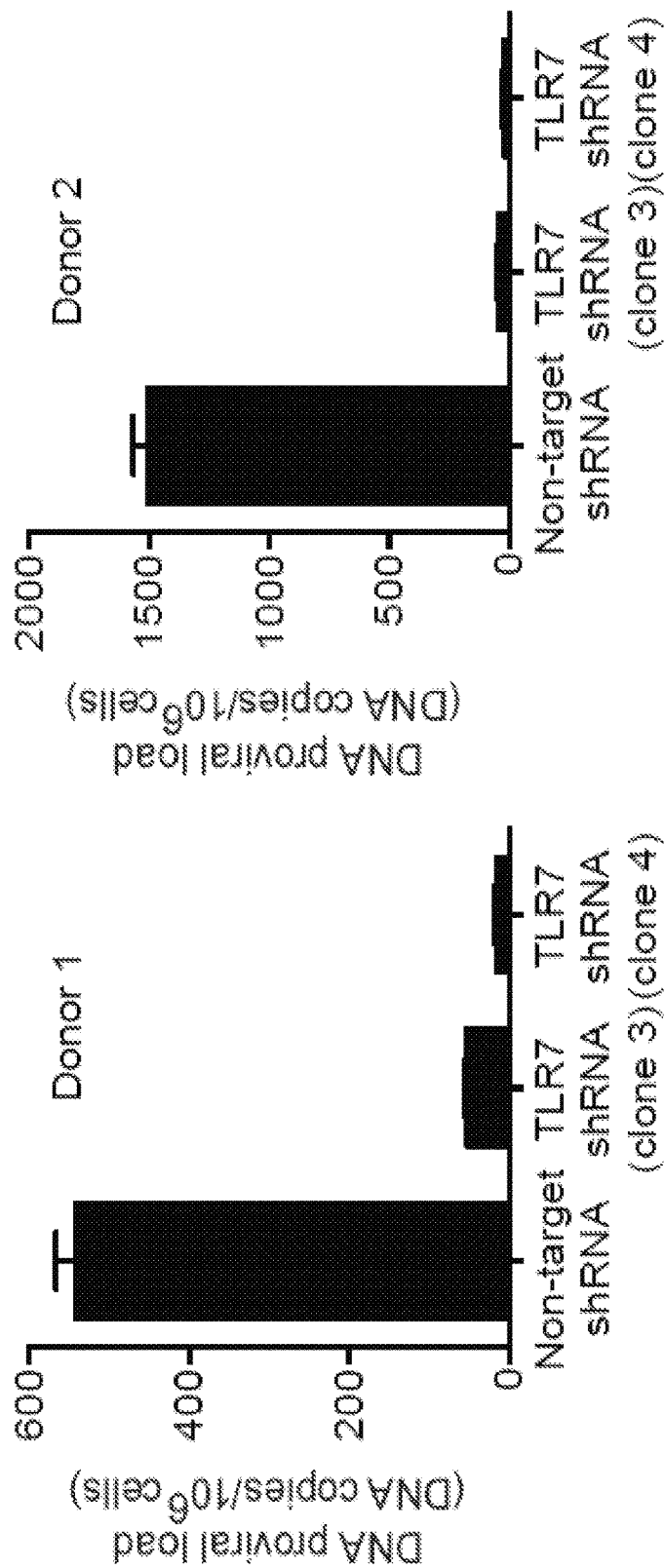
FIG. 53 is a panel of graphs showing proviral integrated DNA load measured at day seven after transduction for 7 days with TLR7-specific shRNA or a control sequence in CD4+ T cells from HIV-1 infected patients (Donor 1, left and Donor 2, right).

Furthermore, proviral integrated DNA load was measured at day seven after stimulation in the presence of IRS661 or a control sequence (FIG. 52) and after transduction with TLR7-specific shRNA (FIG. 53) to monitor the cellular viral reservoir. Inhibition of TLR7 by either IRS661 or protein knockdown resulted in a dramatic decrease in proviral DNA load as compared to control cells (FIGS. 52 and 53).

Figure 54:
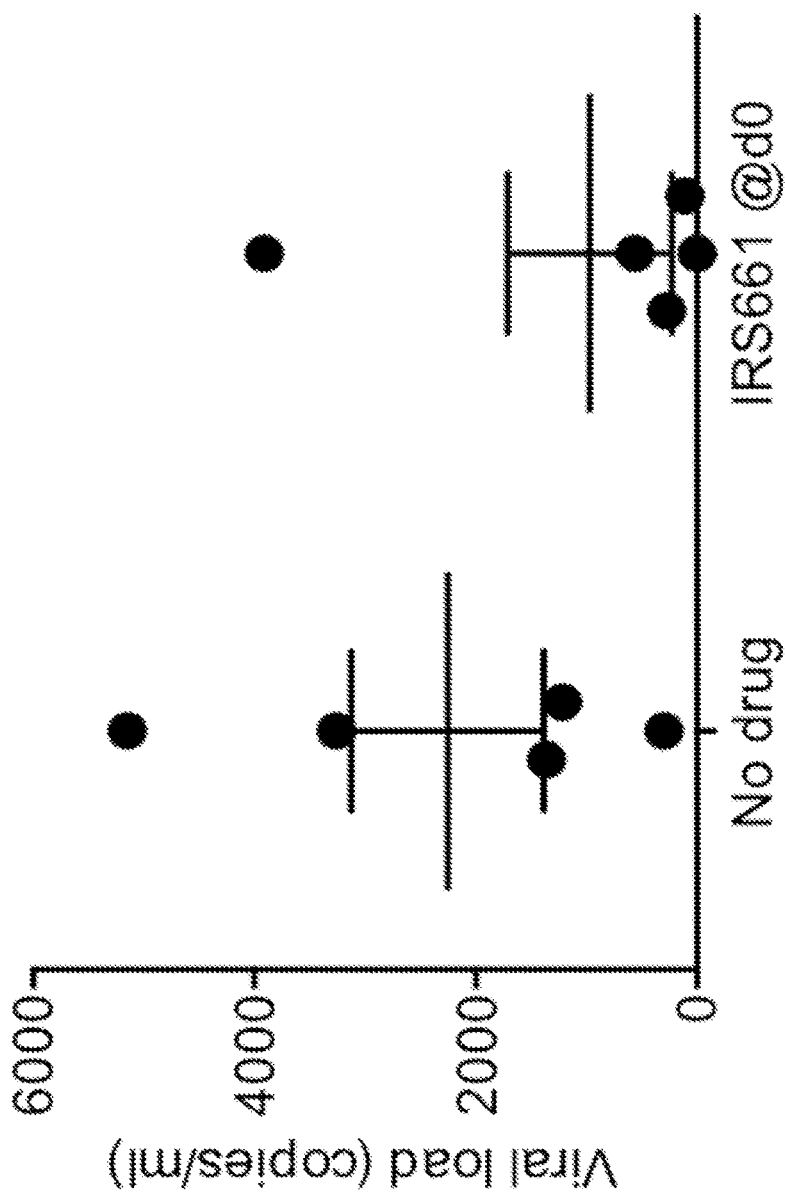
FIG. 54 is a graph showing viral load measured in mice infected with HIV-1 in the presence (right) or absence (left) of the TLR7 inhibitor IRS661 after 7 days of infection.
Figure 55:
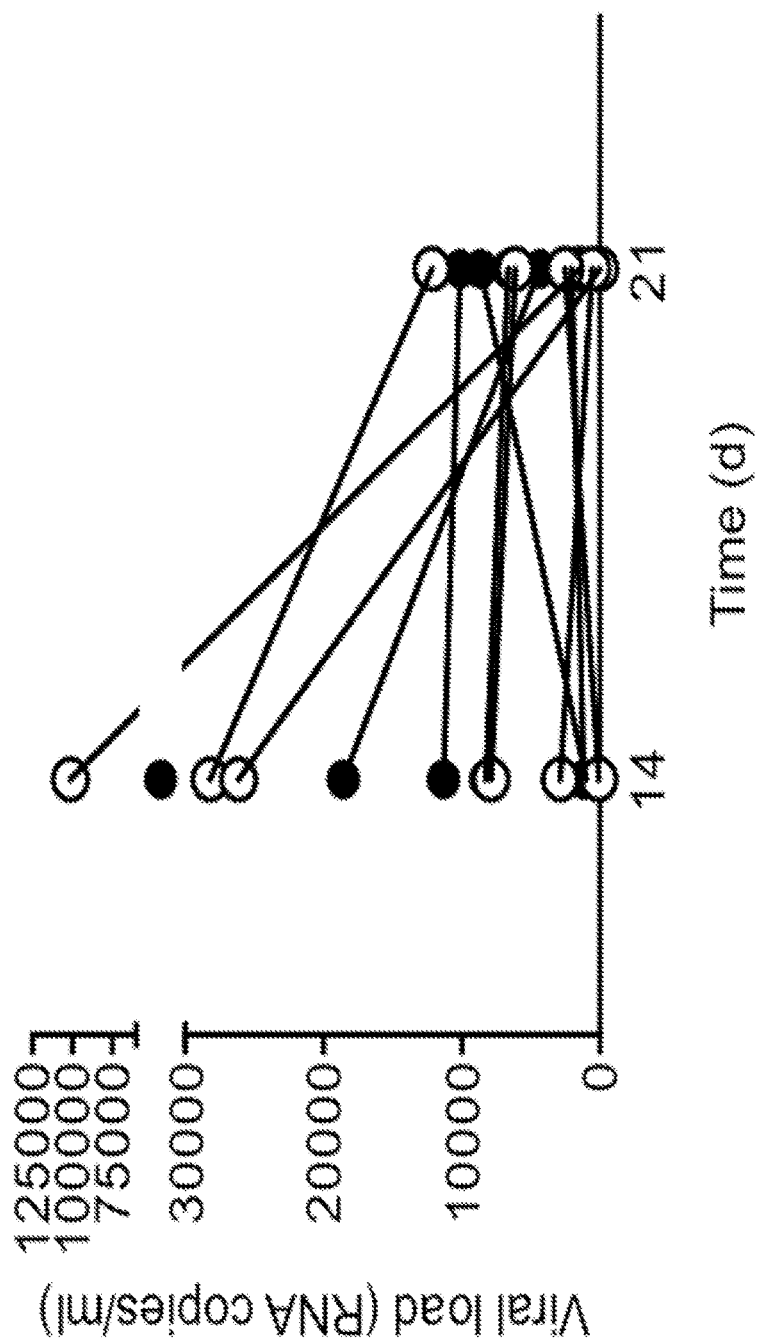
FIG. 55 is a graph showing viral load measured at day 21 after infection on control mice (black dots) or mice where IRS661 was injected at day 14 after infection (white dots). Dots at each time point represent an individual mouse.

In order to test the role of TLR7 inhibition in HIV-1 infection in vivo, a humanized mouse model (Rongvaux et al., Nat. Biotech., 32:364-372 (2014)) was used. Three groups of mice were infected with HIV-1 (NL-432): one control group, another group that was injected with IRS661 at the same time of HIV-1 infection (day 0), and a third group where IRS661 was injected at the peak of infection (day 14 after HIV-1 infection). FIG. 54 shows the viral load measured in the group that was injected with IRS661 at the same time of infection as compared to the infected control. For those mice that were injected with IRS661 at day 14 after infection (FIG. 55, white dots), viral load was measured at day 21 after infection. One mouse from the control group (black dots) died at day 17. The data suggest that in vivo TLR7 blockade in humanized mice decreases HIV-1 viral load, in agreement with the in vitro data.

While infections are generally regarded as illness, humans are colonized with bacteria and viruses. The prime example is that of prokaryotic bacteria adopted for digestion, though humans are commonly colonized with DNA and RNA viruses including endogenous retrovirus. Whether these endogenous retroviruses provide an adoptive advantage, they have co-evolved with the immune system raising the possibility that TLR7 was co-opted in human CD4$^+$ T cells in response to human endogenous retroviruses. While it will be of interest in future investigations to precisely understand when TLR7 is engaged in the HIV-1 infection life-cycle, these data demonstrate a novel mechanism by which HIV-1 may avoid elimination by co-opting NFAT-dependent TLR7-induced T cell anergy.

In summary, TLR7 has been co-opted by CD4+ T cells to induce immune tolerance, in direct opposition to its role in dendritic cells and macrophages. While it is tempting to speculate that this mechanism evolved to prevent activation of CD4+ T cells by endogenous retroviruses, further investigation will be required to determine the role of TLR7 in regulating NFAT-dependent immune responses. In this regard, TLR7 expressed in CD4+ T cells appears to be involved in tolerance induction. Finally, infections with RNA viruses are a major cause of human morbidity. In particular, HIV-1 infection can induce profound dysfunction of immune function, though the mechanisms are surprisingly not well understood. Direct evidence is described herein that single stranded RNA viruses induced non-responsiveness in CD4+ cells by TLR7-induced intracellular calcium signaling with activation of NFAT-dependent anergic gene expression program. RNAi knockdown of the TLR7 gene greatly decreased HIV-1 CD4+ T cell infection while avoiding HIV-1-induced anergy. These data add a new layer of complexity to our understanding of the HIV viral life cycle that needs further investigation and are in contrast with recent published data that describes the cytoplasmic sensors of viral DNA that trigger cell death by pyropoptosis of non-productively infected CD4+ T cells. These discoveries are important for viral disease therapies where down-regulation of TLR7 anergy pathway may restore the immune anergic state associated with HIV-1 or other RNA viral infections. Moreover, TLR7 ligands may be used as a means of inducing "tolerance" on CD4+ T cells in human autoimmune diseases.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of preventing a viral infection of a T cell in a subject in need thereof comprising administering a composition comprising an inhibitor of TLR7 signaling selected from the group consisting of dual-iODN, IMO-3100, DV056, DV1179, chloroquine, hydroxychloroquine, quinacrine, and any combination thereof and further comprising administering a CD3 antibody, an ICOS antibody, or a CD28 antibody to the subject, wherein viral infection of the T cell is prevented following administration of the composition.

2. A method of treating a viral infection in a subject in need thereof comprising administering a composition comprising an inhibitor of TLR7 signaling to the subject, wherein the viral infection is reduced in the subject following administration of the TLR7 inhibitor.

3. The method of claim 1, wherein the inhibitor of TLR7 signaling is capable of decreasing expression of TLR7.

4. The method of claim 1, wherein administering the composition increases secretion of at least one selected from the group consisting of IL-2, IFNγ and IL-17.

5. The method of claim 1, wherein the composition is capable of preventing viral infection of a CD4+ T cell.

6. The method of claim 1, wherein the subject is exposed to a virus prior to or after administration of the composition.

7. The method of claim 1, wherein the viral infection is selected from the group consisting of a hepatitis B virus (HBV), a hepatitis C virus (HCV), human T-lymphotropic virus (HTLV) and a human immunodeficiency virus (HIV) infection.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence

<400> SEQUENCE: 1
tgcttgcaag cttgcaagca                                              20

<210> SEQ ID NO 2
<211> LENGTH: 18
<212> TYPE: DNA
<213> ORGANISM: Artificial Sequence
<220> FEATURE:
<223> OTHER INFORMATION: Synthetic sequence

<400> SEQUENCE: 2
tgctcctgga ggggttgt                                                18

<210> SEQ ID NO 3
<211> LENGTH: 24
<212> TYPE: DNA
<213> ORGANISM: Artificial Sequence
<220> FEATURE:
<223> OTHER INFORMATION: Synthetic sequence

<400> SEQUENCE: 3
tgcttgacat cctggagggg ttgt                                         24

<210> SEQ ID NO 4
<211> LENGTH: 35
<212> TYPE: DNA
<213> ORGANISM: Artificial Sequence
<220> FEATURE:
<223> OTHER INFORMATION: Synthetic sequence

<400> SEQUENCE: 4
```

```
tgcttgacag cttgacagca tcctggaggg gttgt                                   35

<210> SEQ ID NO 5
<211> LENGTH: 17
<212> TYPE: DNA
<213> ORGANISM: Artificial Sequence
<220> FEATURE:
<223> OTHER INFORMATION: Synthetic sequence

<400> SEQUENCE: 5
gctcctggag gggttgt                                                       17

<210> SEQ ID NO 6
<211> LENGTH: 16
<212> TYPE: DNA
<213> ORGANISM: Artificial Sequence
<220> FEATURE:
<223> OTHER INFORMATION: Synthetic sequence

<400> SEQUENCE: 6
ctcctggagg ggttgt                                                        16

<210> SEQ ID NO 7
<211> LENGTH: 18
<212> TYPE: DNA
<213> ORGANISM: Artificial Sequence
<220> FEATURE:
<223> OTHER INFORMATION: Synthetic sequence

<400> SEQUENCE: 7
aaatcctgga ggggttgt                                                      18
```